(12) United States Patent
Krishnan

(10) Patent No.: US 10,474,916 B2
(45) Date of Patent: Nov. 12, 2019

(54) TRAINING OF VEHICLES TO IMPROVE AUTONOMOUS CAPABILITIES

(71) Applicant: Ashok Krishnan, Flynn (AU)

(72) Inventor: Ashok Krishnan, Flynn (AU)

( * ) Notice: Subject to any disclaimer, the term of this patent is extended or adjusted under 35 U.S.C. 154(b) by 0 days.

(21) Appl. No.: 16/194,404

(22) Filed: Nov. 19, 2018

(65) Prior Publication Data

US 2019/0156150 A1 May 23, 2019

Related U.S. Application Data

(60) Provisional application No. 62/588,444, filed on Nov. 20, 2017, provisional application No. 62/760,073, filed on Nov. 13, 2018.

(51) Int. Cl.
| | | |
|---|---|---|
| *G06K 9/00* | (2006.01) | |
| *G06N 20/00* | (2019.01) | |
| *A61B 5/22* | (2006.01) | |
| *A61B 5/00* | (2006.01) | |
| *A61B 3/113* | (2006.01) | |

(Continued)

(52) U.S. Cl.
CPC .......... *G06K 9/00892* (2013.01); *A61B 3/113* (2013.01); *A61B 5/225* (2013.01); *A61B 5/6893* (2013.01); *G06K 9/00832* (2013.01); *G06K 9/00845* (2013.01); *G06K 9/6256* (2013.01); *G06N 20/00* (2019.01); *G05D 1/0088* (2013.01); *G05D 2201/0213* (2013.01)

(58) Field of Classification Search
CPC ....... A61B 3/113; A61B 5/225; A61B 5/6893; G05D 1/0088; G05D 2201/0213; G06K 9/00597; G06K 9/00744; G06K 9/00832; G06K 9/00845; G06K 9/00892; G06K 9/6256; G06N 20/00
See application file for complete search history.

(56) References Cited

U.S. PATENT DOCUMENTS

| | | |
|---|---|---|
| 5,835,008 A | 11/1998 | Colemere, Jr. |
| 2014/0148988 A1 | 5/2014 | Lathrop et al. |
| 2015/0175168 A1 | 6/2015 | Hoye et al. |

(Continued)

FOREIGN PATENT DOCUMENTS

| | | |
|---|---|---|
| WO | 2016/077779 A1 | 5/2016 |
| WO | 2016/0777779 A1 | 5/2016 |
| WO | 2016/169582 A1 | 10/2016 |

OTHER PUBLICATIONS

Third Written Opinion of the International Preliminary Examination Authority (IPEA) dated May 17, 2019 of Application No. PCT-AU2018-051223.

(Continued)

*Primary Examiner* — Manuchehr Rahmjoo

(57) ABSTRACT

Systems and methods to improve performance, reliability, learning and safety and thereby enhance autonomy of vehicles. Human sensors are used to capture human eye movement, hearing, hand grip and contact area, and foot positions. Event signatures corresponding to human actions, reactions and responses are extracted form these sensor values and correlated to events, status and situations acquired using vehicle and outside environment sensors. These event signatures are then used to train vehicles to improve their autonomous capabilities. Human sensors are vehicle mounted or frame mounted. Signatures obtained from events are classified and stored.

4 Claims, 31 Drawing Sheets

(51) Int. Cl.
  *G06K 9/62* (2006.01)
  *G05D 1/00* (2006.01)

(56) References Cited

U.S. PATENT DOCUMENTS

| | | | |
|---|---|---|---|
| 2015/0339589 A1* | 11/2015 | Fisher | B25J 9/16 |
| | | | 706/12 |
| 2016/0001781 A1* | 1/2016 | Fung | B60W 40/08 |
| | | | 701/36 |
| 2016/0173864 A1 | 6/2016 | Yu et al. | |
| 2016/0210382 A1 | 7/2016 | Alaniz et al. | |
| 2016/0249803 A1 | 9/2016 | Saito | |
| 2016/0303972 A1 | 10/2016 | Kuhne | |
| 2017/0197618 A1 | 7/2017 | Ali et al. | |

OTHER PUBLICATIONS

The KITTI Vision Benchmark Suite, KIT and TTI at Chicago, [retrieved from Internet on Mar. 25, 2019] <URL: https://web.archive.org/web/20171117005347/http://www.cvlibs.net/datasets/kitti/> published on Nov. 17, 2017 as per Wayback Machine.

ImageNet, Stanford University [retrieved from internet on Mar. 25, 2019] <URL: https://web.archive.org/web/20171119121100/http://image-net.org/> published on Nov. 19, 2017 as per Wayback Machine.

Wang Y. et al., "Joint Deep Neural network modelling and statistical Analysis in Characterizing Driving Behaviors", IEEE Intelligent Vehicles Symposium (IV) Changshu, Suzhou, China, Jun. 26-30, 2018, pp. 2060-2065.

Dong W. et al., "Characterizing Driving Styles With Deep Learning", arXiv:1607.03611 [cs.AI], Oct. 8, 2016, https://arxiv.org/pdf/1607.03611.pdf.

* cited by examiner

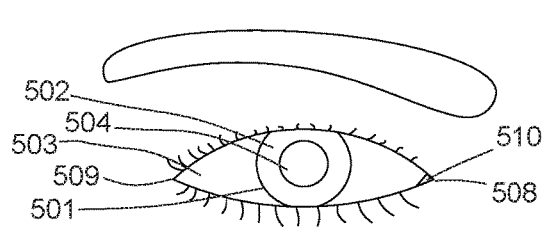
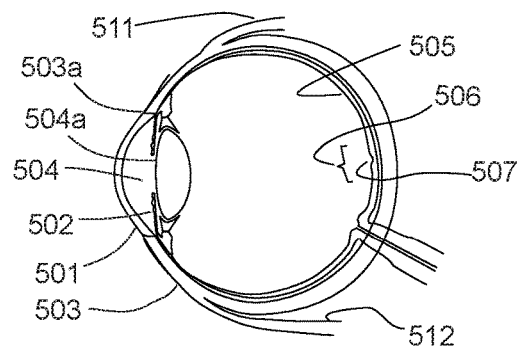
fig 5a
fig 5a1
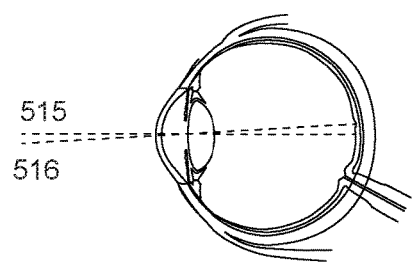
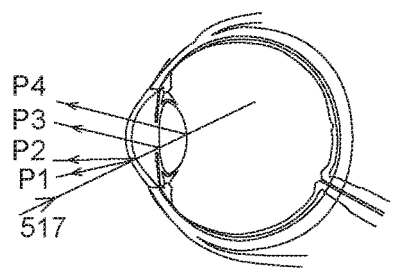
fig 5b
fig 5c
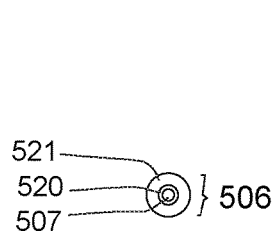
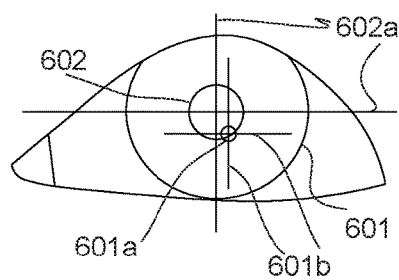
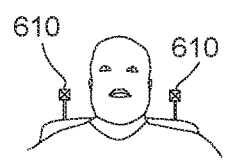
fig 5d
fig 6a
fig 6b
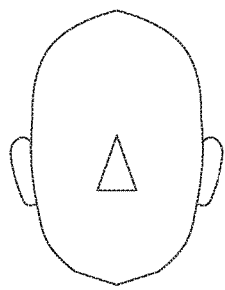
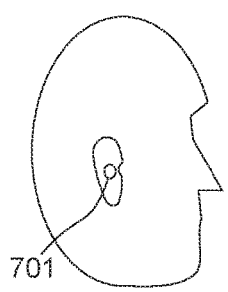
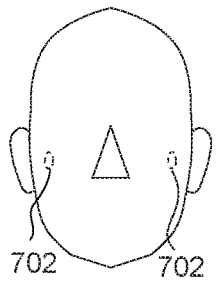
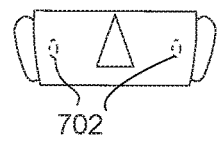
fig 7a
fig 7b
fig 7c
fig 7d

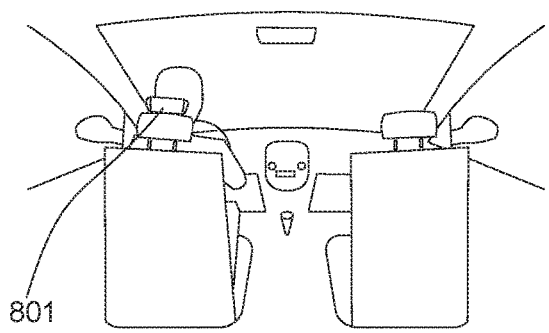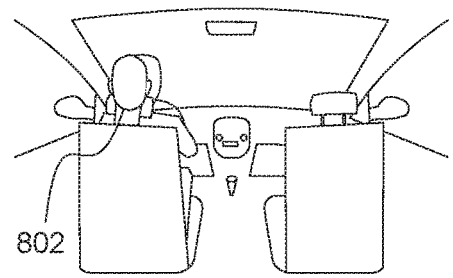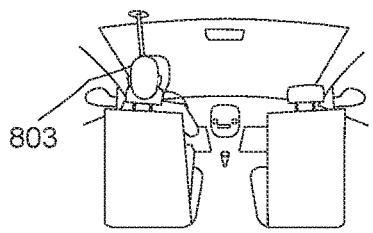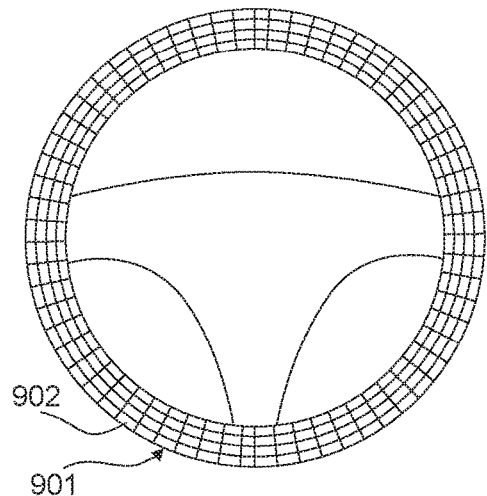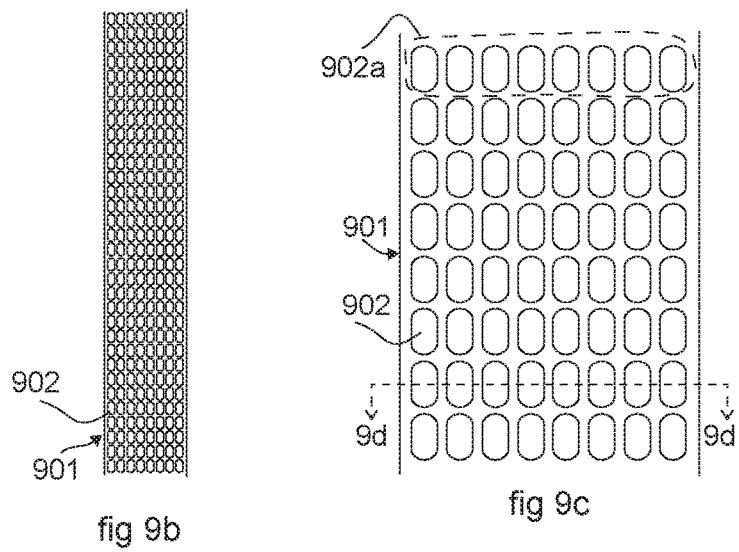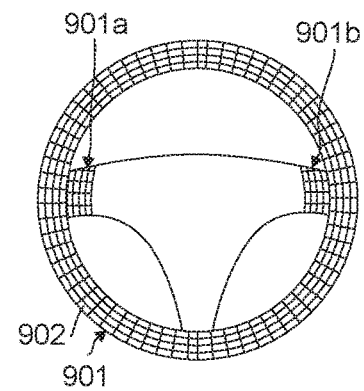

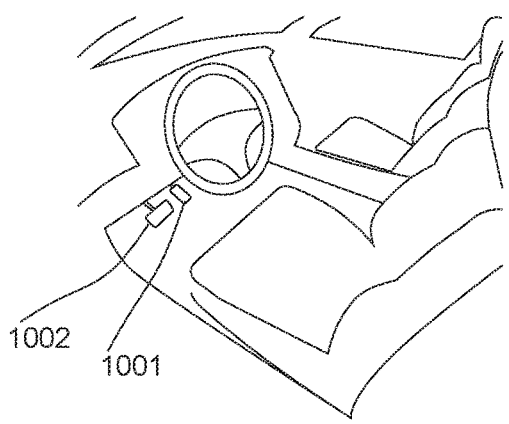
fig 10a
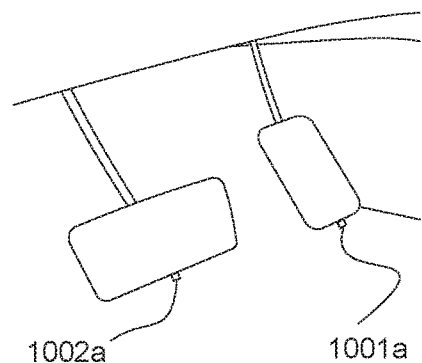
fig 10b
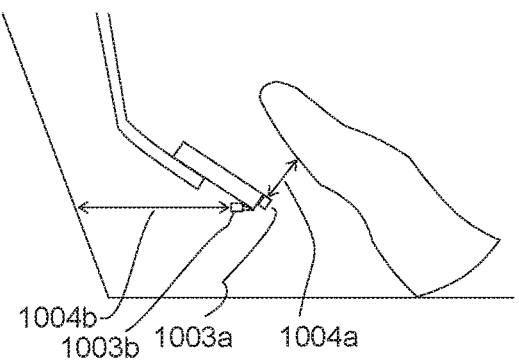
fig 10c
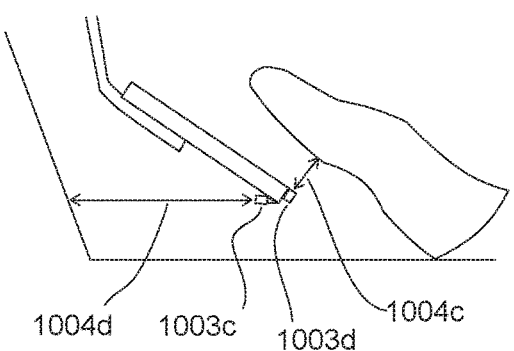
fig 10c1
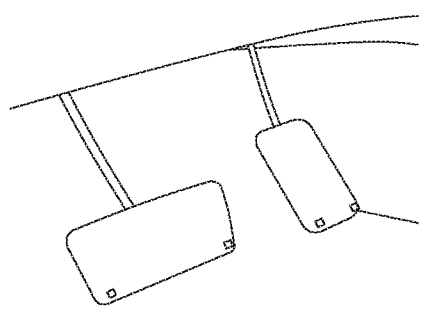
fig 10d
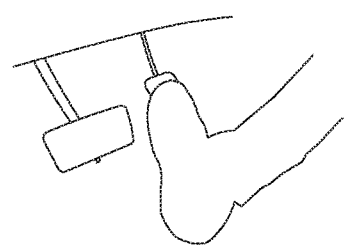
fig 10e
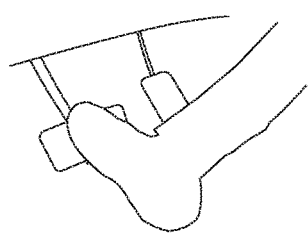
fig 10f
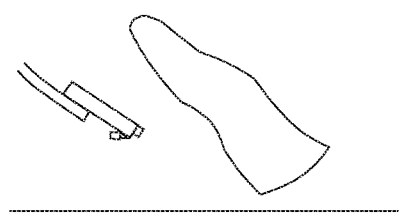
fig 10g
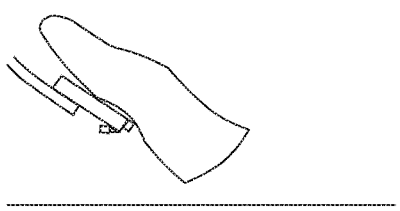
fig 10h

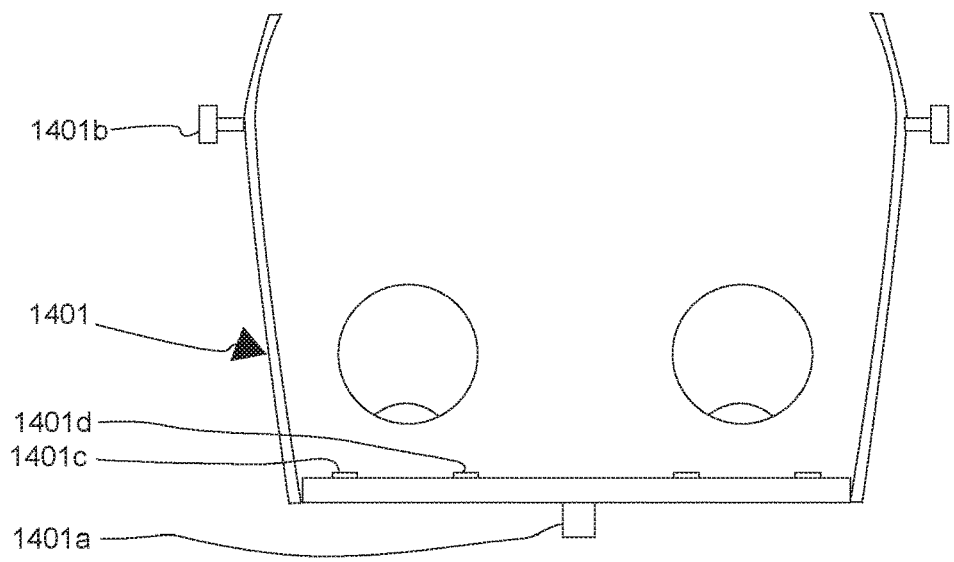
fig 14a1
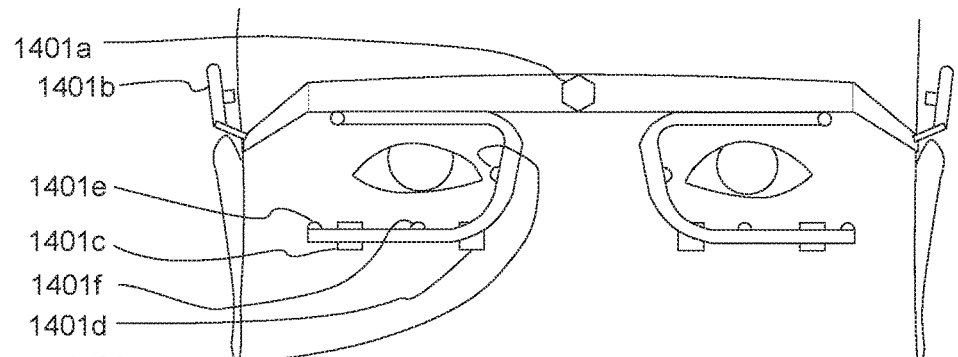
fig 14a
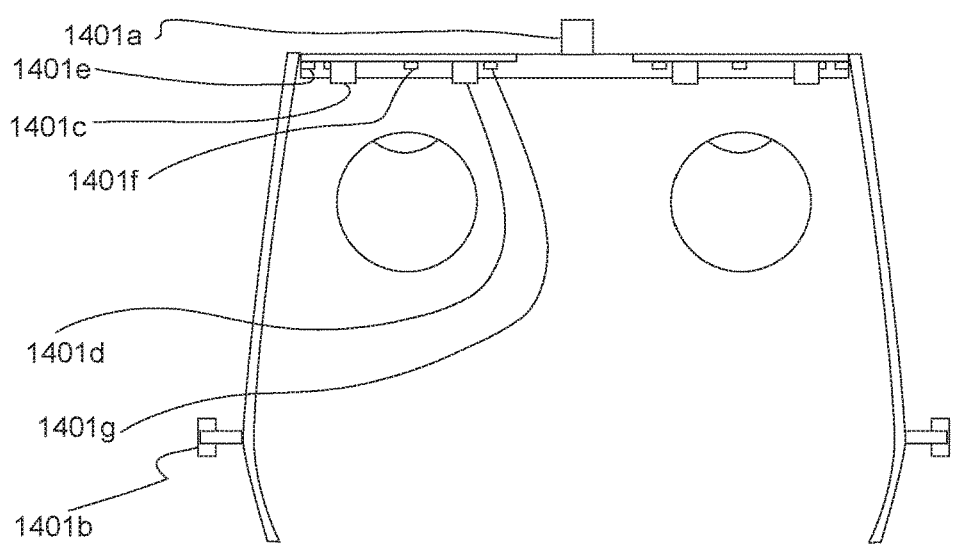
fig 14a2

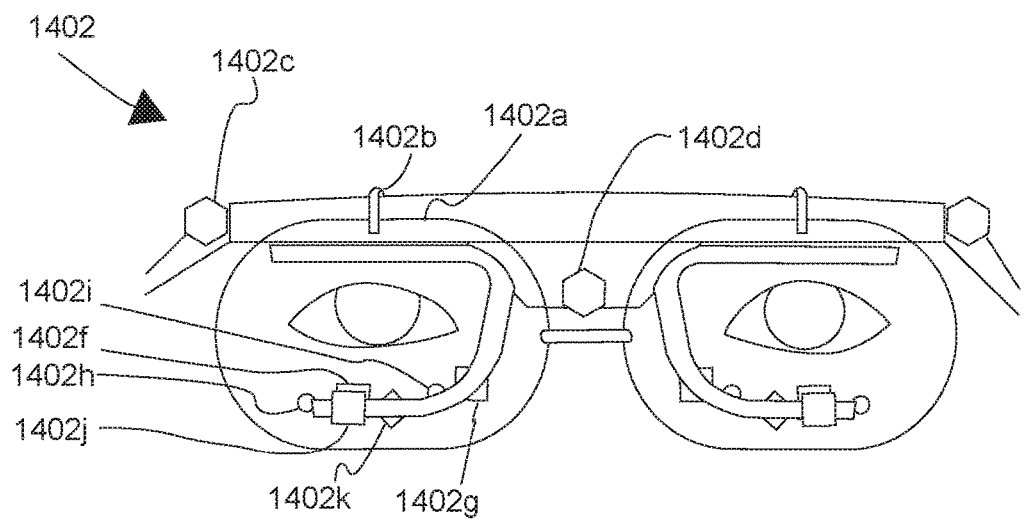
fig 14b
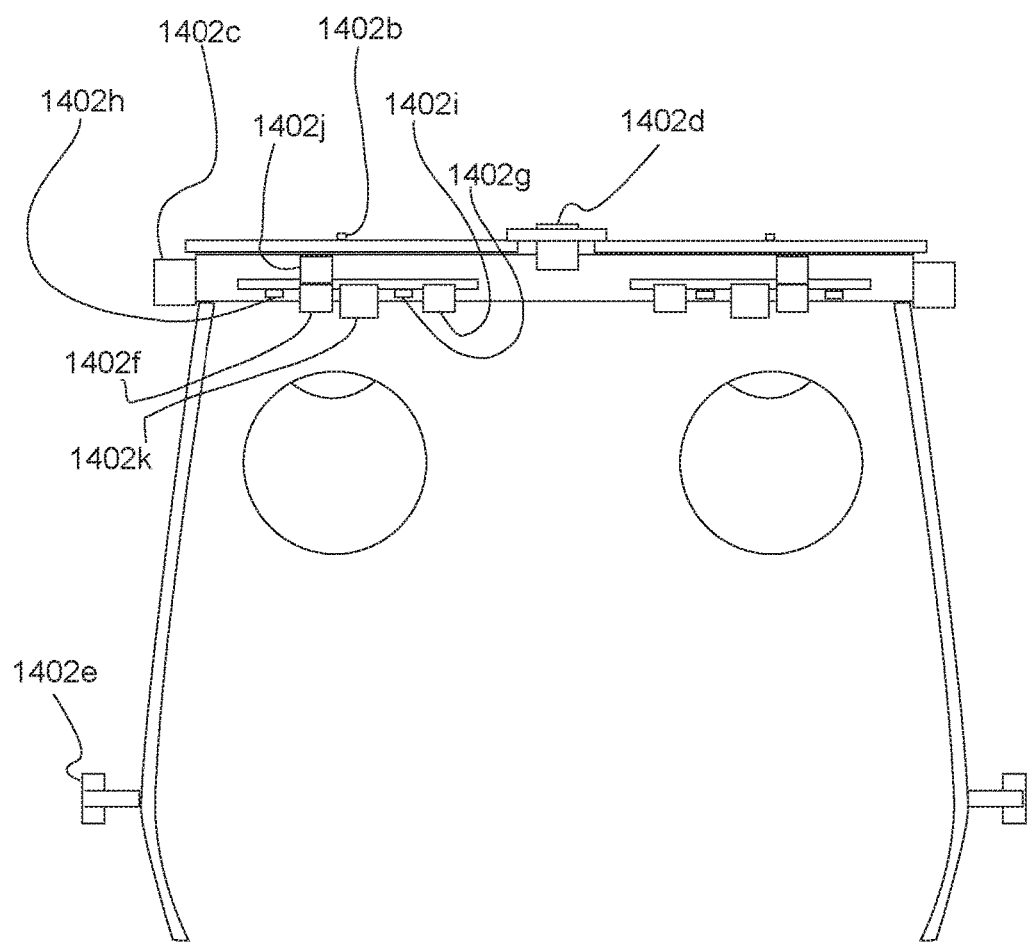
fig 14b1

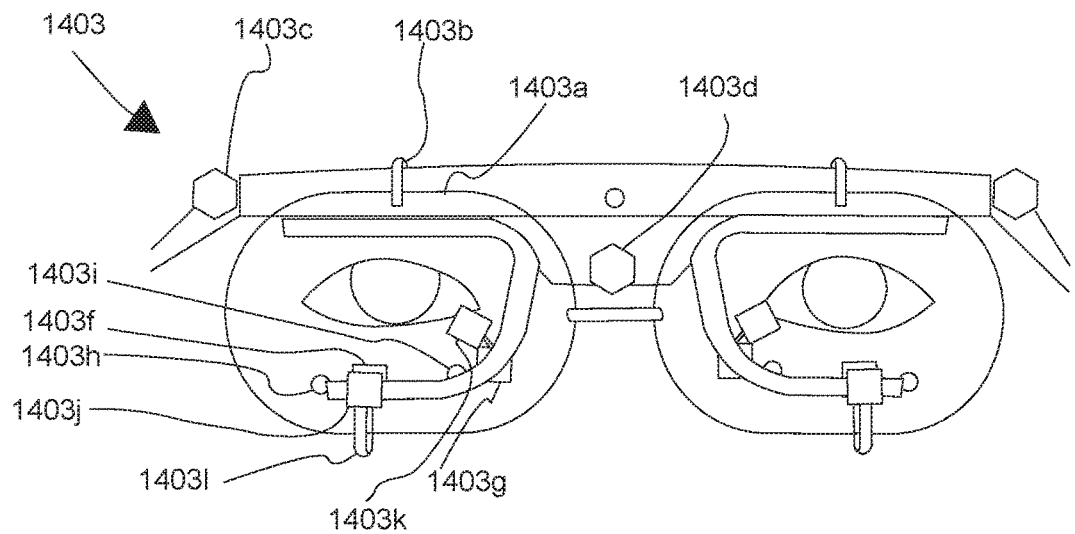
fig 14c
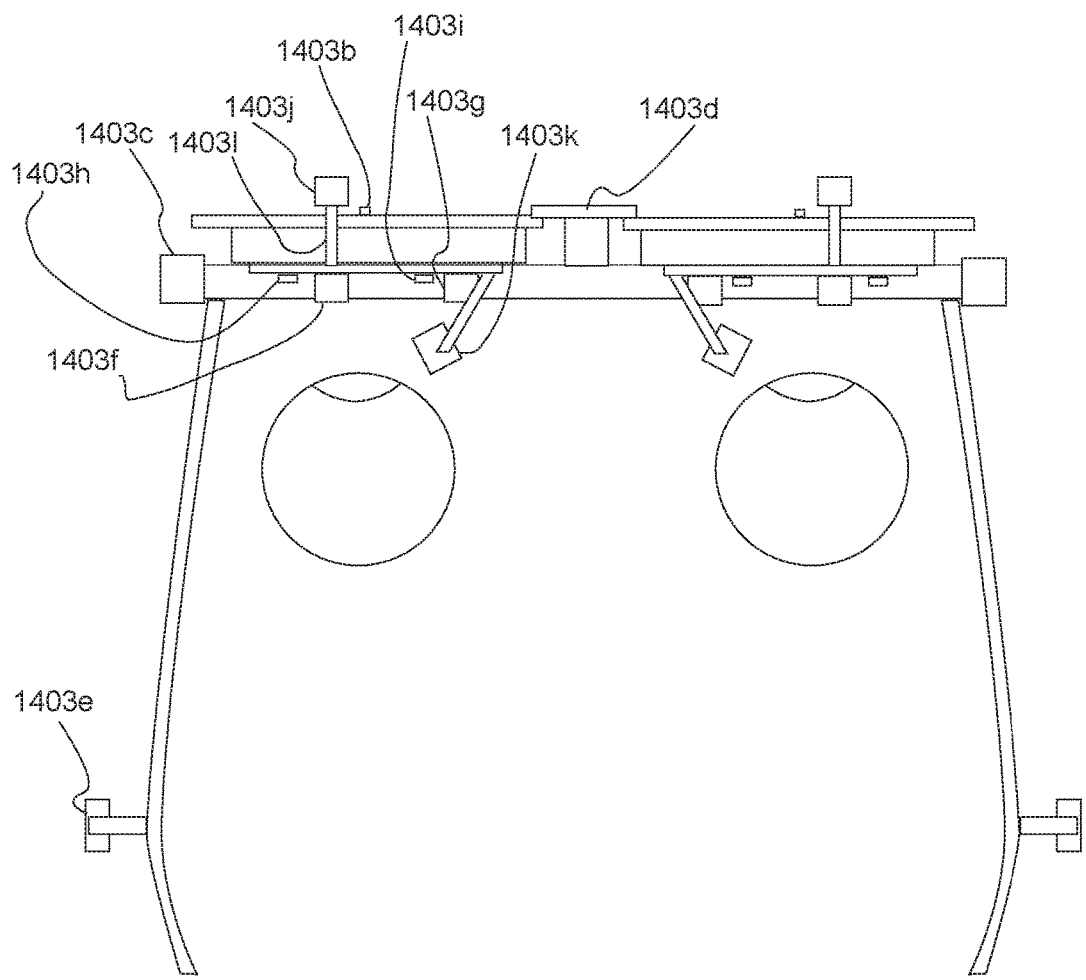
fig 14c1

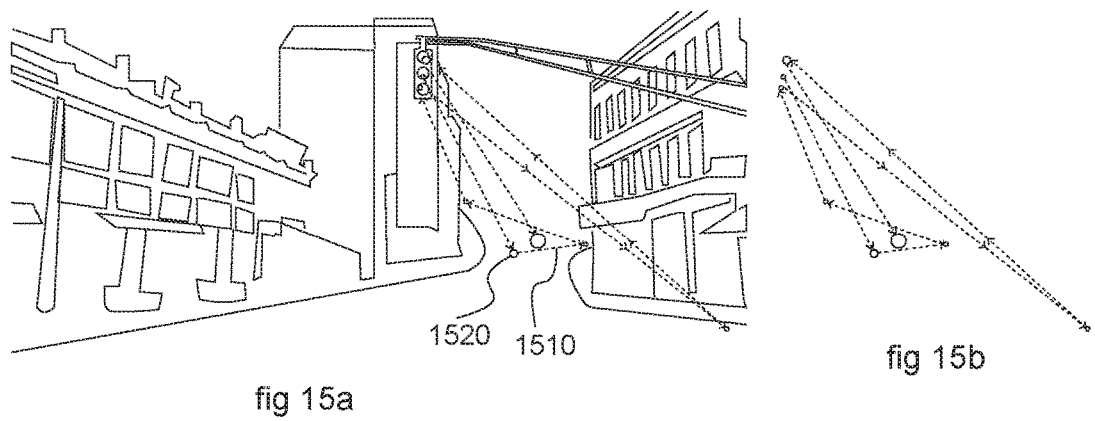
fig 15a
fig 15b
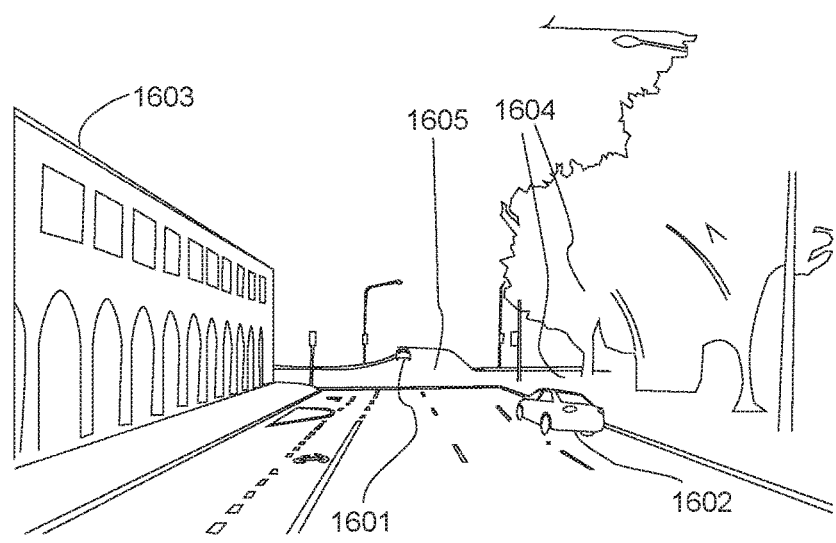
fig 16
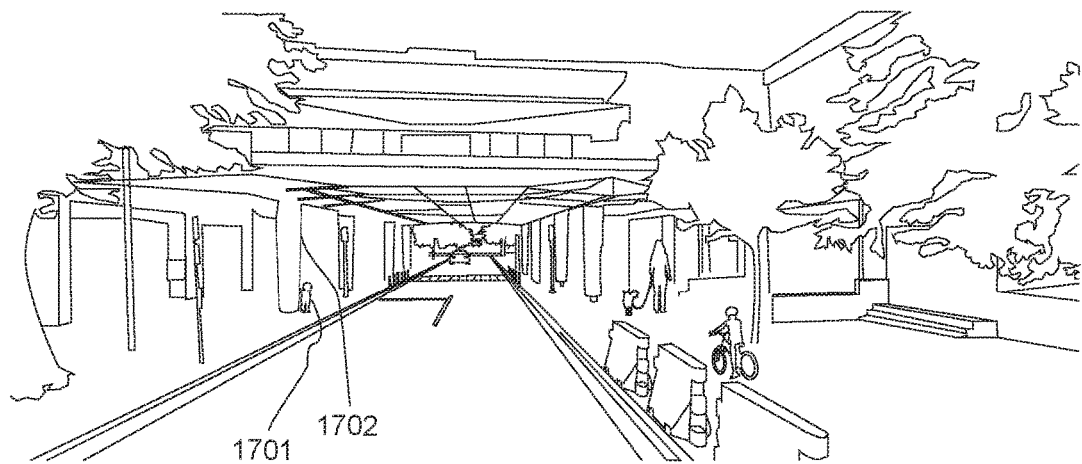
fig 17

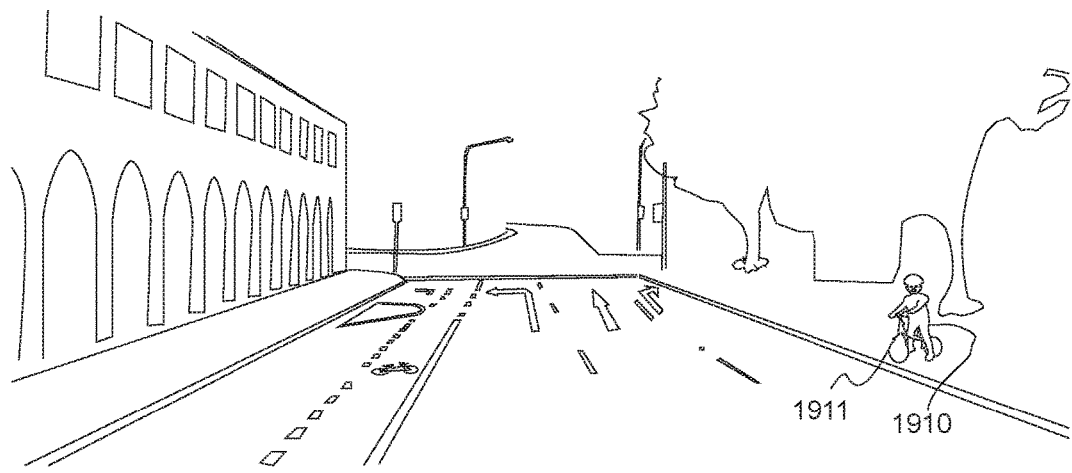
fig 19b
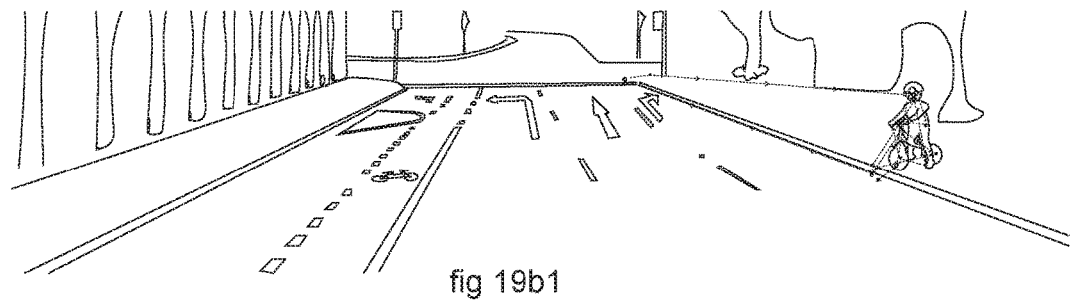
fig 19b1
fig 19b2
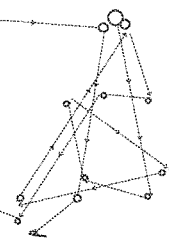
fig 19b3
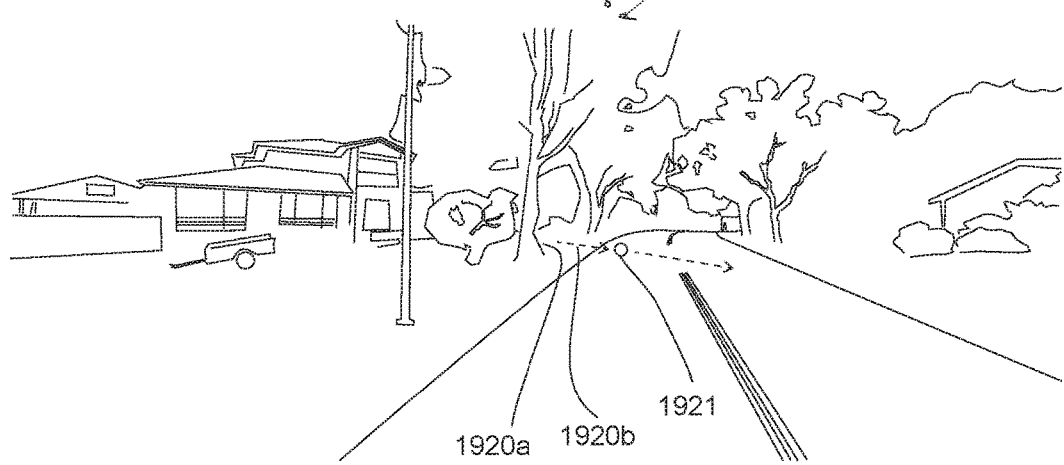
fig 19c

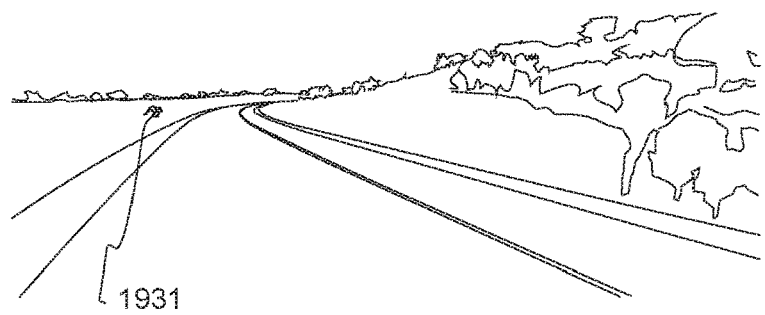
fig 19d1
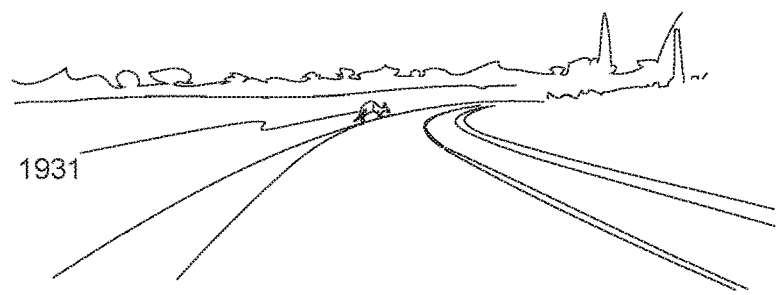
fig 19d2
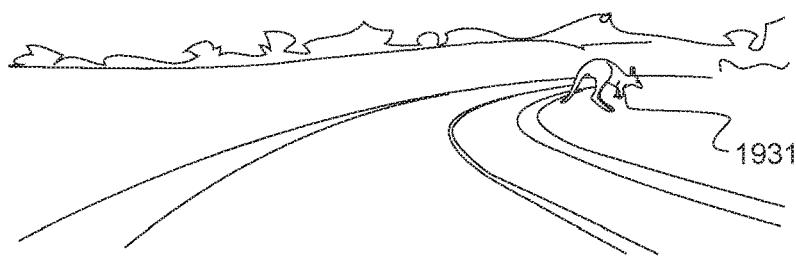
fig 19d3
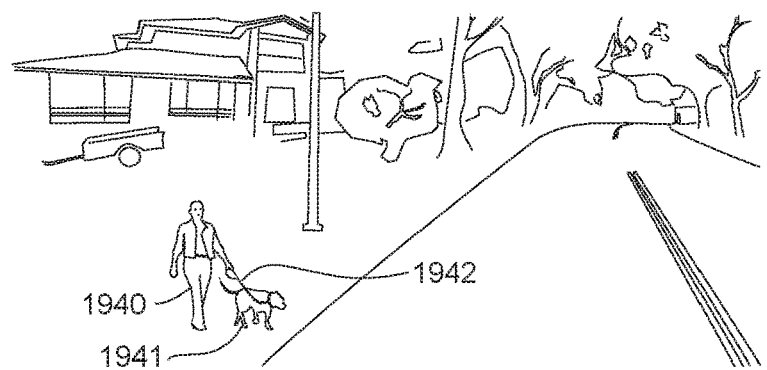
fig 20

2400 SIGN

SIGN = [([[SIGNAME][TIME][GEOLOCATION][SN][CN][SGN][PN]] [2200](EST))]
[([[SIGNAME][TIME][GEOLOCATION][SN][CN][SGN][PN]] [2200](EST+ΔT))]
[([[SIGNAME][TIME][GEOLOCATION][SN][CN][SGN][PN]] [2200](EST+2ΔT)] ...
[[[SIGNAME][TIME][GEOLOCATION][SN][CN][SGN][PN]] [2200](EST+EP))]

WHERE

[SIGNAME] = [SIGCAT][SIGVAR][SIGVER][SIGFEAT]

AND

2500 CATEGORISATION OF SIGNATURE

2501 DANGER (PRIORITY A)
2502 CHILD (PRIORITY B)
2503 EFFICIENCY (PRIORITY C)
2504 COURTESY (PRIORITY D)
2505 SPECIAL OCCASIONS (PRIORITY E)
2506 WEATHER RELATED (PRIORITY F)
2507 NEW TRAFFIC SITUATION (PRIORITY G)
2508 UNCLEAR SITUATION (PRIORITY H)
2509 STARTLED (PRIORITY I)
2510 UNEXPECTED OBJECTS (PRIORITY J)
2511 UNEXPECTED ACTIONS OF OTHERS (PRIORITY K)
2512 SUDDEN ACTIONS OF OTHERS (PRIORITY L)
2513 COMFORT LEVELS- SPEED, DISTANCE (PRIORITY M)
2514 ENVIRONMENT (LOW-LIGHT, SUN-IN-EYES, HIGH-BEAM) (PRIORITY N)
2515 LEGAL (PRIORITY O)

fig 25

2700 NON-EVENT CATEGORIES

2701 LAWFULNESS (WEIGHTAGE: -10 TO +10)
2702 SAFETY (WEIGHTAGE: -10 TO +10)
2703 RESPONSIVENESS (WEIGHTAGE: -10 TO +10)
2704 STATE (WEIGHTAGE: -10 TO +10)
2705 DEFENSIVE (WEIGHTAGE: -10 TO +10)
2706 SKILL (WEIGHTAGE: -10 TO +10)
2707 CONDUCT (WEIGHTAGE: -10 TO +10)
2708 KNOWLEDGE (WEIGHTAGE: -10 TO +10)

fig 27

| Category | Vehicle type | Eye movement sensor type | Aural sensor present? | Foot sensor present? | Hand sensor present? | World type |
|---|---|---|---|---|---|---|
| C1 | VV | P, C | ? | no | no | CW, VW |
| C2 | VV | P, C | ? | yes | yes | CW, VW |
| C3 | RV | P | no | no | no | RW |
| C4 | RV | P, C | yes | yes | yes | RW |
| C5 | RV | P, C | yes | yes | yes | RW | fig 37

2801 SUBJECT FAILURE SCORING

2801A SUBJECT PRIMARY FAILURE
(WEIGHTAGE- 100X-50X)
CAUSING SEVERE HUMAN INJURY AND DANGER TO LIFE

2801B SUBJECT SECONDARY FAILURE
(WEIGHTAGE- 49X-25X)
CAUSING MEDIUM HUMAN INJURY REQUIRING HOSPITALISATION BUT NO DANGER TO LIFE
POTENTIAL TO HAVE CAUSED SUBJECT PRIMARY FAILURE

2801C SUBJECT TERTIARY FAILURE
(WEIGHTAGE- 24X-13X)
CAUSING MINOR INJURIES NOT REQUIRING MEDICAL HOSPITALISATION BUT REQUIRING FIRST AID
HIGH DAMAGE TO PROPERTY, POTENTIAL TO HAVE CAUSED SUBJECT SECONDARY FAILURE

2801D SUBJECT QUATERNARY FAILURE
(WEIGHTAGE- 12X-6X)
CAUSING HUMAN INJURY NOT REQUIRING ANY MEDICAL ATTENTION OR FIRST-AID
MEDIUM DAMAGE TO PROPERTY
POTENTIAL TO HAVE CAUSED SUBJECT TERTIARY FAILURE

2801E SUBJECT QUINARY FAILURE
(WEIGHTAGE- 5X-2X)
POTENTIAL TO HAVE CAUSED SUBJECT QUATERNARY FAILURE
MINOR DAMAGE TO PROPERTY

2801F SUBJECT SENARY FAILURE
(WEIGHTAGE- 1X)
POTENTIAL TO CAUSE SUBJECT QUINARY FAILURE
NO POSSIBILITY OF HUMAN INJURY
NO DAMAGE TO PROPERTY

2801G SUBJECT SEPTENARY FAILURE
(WEIGHTAGE- 0.1X)
POTENTIAL TO CAUSE SENARY SUBJECT FAILURE
NO POSSIBILITY OF HUMAN INJURY
NO POSSIBILITY OF DAMAGE TO PROPERTY

2802 SUBJECT SUCCESS SCORING

2802A SUBJECT PRIMARY SUCCESS
(WEIGHTAGE- 100X-50X)
PREVENTING SEVERE HUMAN INJURY AND DANGER TO LIFE

2802B SUBJECT SECONDARY SUCCESS
(WEIGHTAGE- 49X-25X)
PREVENTING MEDIUM HUMAN INJURY REQUIRING HOSPITALISATION BUT NO DANGER TO LIFE

2802C SUBJECT TERTIARY SUCCESS
(WEIGHTAGE- 24X-13X)
PREVENTING MINOR INJURIES NOT REQUIRING MEDICAL HOSPITALISATION BUT REQUIRING FIRST-AID
PREVENTING MAJOR DAMAGE TO PROPERTY

2802D SUBJECT QUATERNARY SUCCESS
(WEIGHTAGE- 12X-6X)
PREVENTING HUMAN INJURY NOT REQUIRING ANY MEDICAL ATTENTION OR FIRST-AID
PREVENTING MEDIUM DAMAGE TO PROPERTY

2802E SUBJECT QUINARY SUCCESS
(WEIGHTAGE- 5X-3X)
PREVENTING MINOR DAMAGE TO PROPERTY

2802F SUBJECT SENARY SUCCESS
(WEIGHTAGE- 2X)
PREVENTING SUDDEN CHANGES IN SPEED, DIRECTION, DISTANCE fig 28a

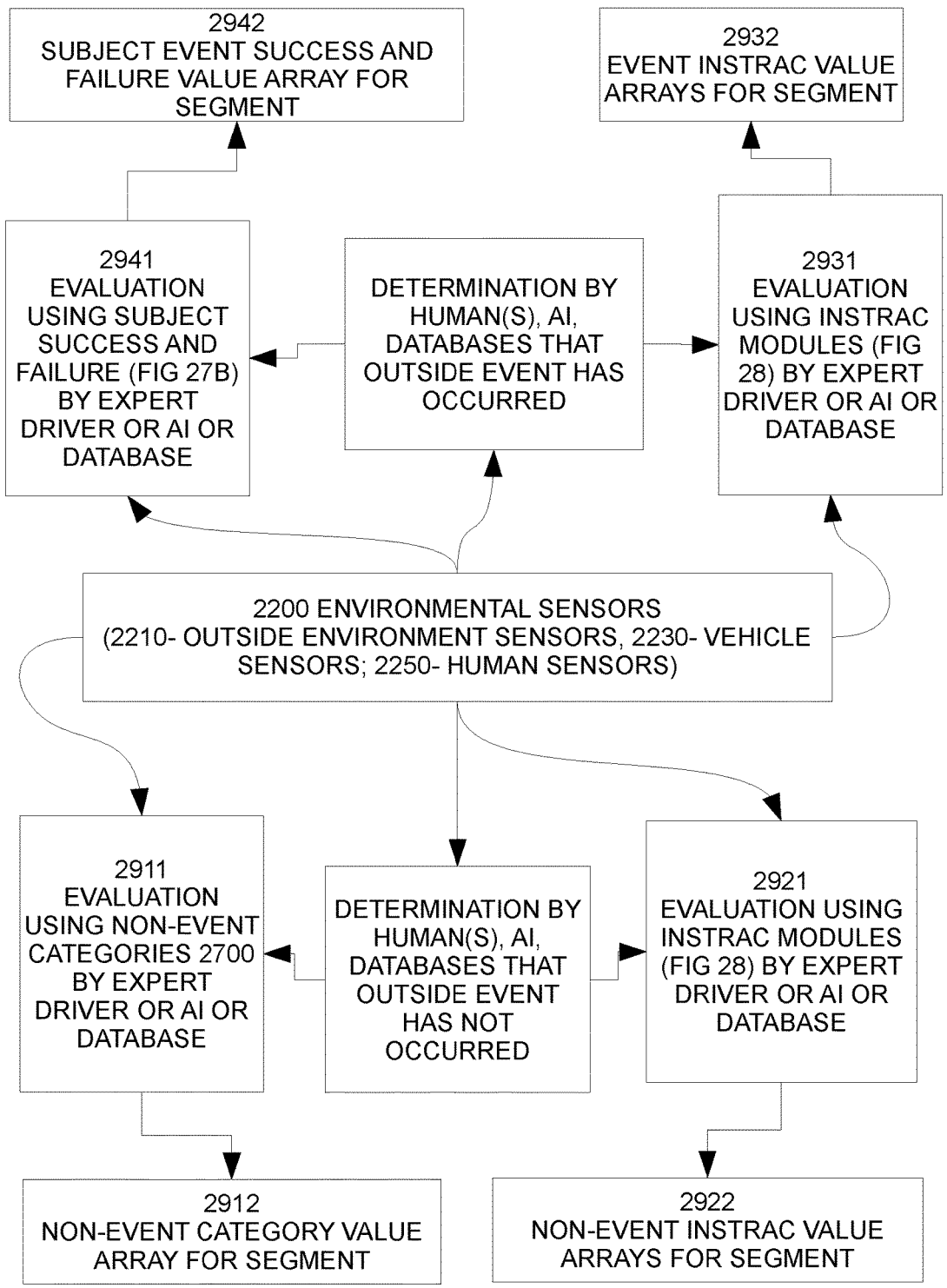
fig 29a1

3000 PATH AND SEGMENT ARRAY

| PATH 1, SEGMENT 1 P1SG1 | PATH 1, SEGMENT 2 P1SG2 | PATH 1, SEGMENT SGN P1SGN |
|---|---|---|
| PATH 2, SEGMENT 1 P2SG1 | PATH 2, SEGMENT 2 P2SG2 | PATH 2, SEGMENT SGN P2SGN |
| PATH PN, SEGMENT 1 PNSG1 | PATH PN, SEGMENT 2 PNSG1 | PATH PN, SEGMENT SGN PNSGN |

3025 SUBJECT ARRAY

| SUBJECT 1 S1 | SUBJECT 2 S2 | SUBJECT N SN |
|---|---|---|

3050 CONDITION ARRAY

| CONDITION 1 C1 | CONDITION 2 C2 | CONDITION N CN |
|---|---|---| fig 30c

3010A PATH AND SEGMENT SCALING FACTOR ARRAY

| PATH 1, SEGMENT 1 SCALING FACTOR SF(P1SG1) | PATH 1, SEGMENT 2 SCALING FACTOR SF(P1SG2) | PATH 1, SEGMENT SGN SCALING FACTOR SF(P1SGN) |
|---|---|---|
| PATH 2, SEGMENT 1 SCALING FACTOR SF(P2SG1) | PATH 2, SEGMENT 2 SCALING FACTOR SF(P2SG2) | PATH 2, SEGMENT SGN SCALING FACTOR SF(P1SGN) |
| PATH PN, SEGMENT 1 SCALING FACTOR SF(PNSG1) | PATH PN, SEGMENT 2 SCALING FACTOR SF(PNSG2) | PATH PN, SEGMENT SGN SCALING FACTOR SF(PNSGN) |

3025A SUBJECT SCALING FACTOR ARRAY

| SUBJECT 1 SCALING FACTOR SF(S1) | SUBJECT 2 SCALING FACTOR SF(S2) | SUBJECT SN SCALING FACTOR SF(SN) |
|---|---|---|

3050A CONDITION SCALING FACTOR ARRAY

| CONDITION 1 SCALING FACTOR SF(C1) | CONDITION 2 SCALING FACTOR SF(C2) | CONDITION CN SCALING FACTOR SF(CN) |
|---|---|---| fig 30d ered by the

TRAINING OF VEHICLES TO IMPROVE AUTONOMOUS CAPABILITIES

BACKGROUND OF THE INVENTION

Autonomous vehicles (AV) are expected to eventually replace the much of the traditional human operation of vehicles. The task of automation is greatly aided by the exponential growth of computing capabilities, including hardware and software. Improved software, lidar, radar, infrared and ultrasound sources are being deployed in test vehicles to improve their autonomy. However, vehicles that are truly fully autonomous have not yet been developed.

BRIEF SUMMARY OF THE INVENTION

In an embodiment, human eye movements captured during driving are used to train vehicles to be more autonomous. In another embodiment, additional human sensors gather data from binaural microphones, data related to hand (grip and contact area on steering wheel) and foot position, which are used to train vehicles to improve their autonomous functionality. Eye movement is captured through cameras and smarthphones located on frames mounted on humans or on dashpads of vehicles. Illumination sources include IR illuminators, light from phone screens, and ambient light. Hand grip and contact area on the steering wheel is captured using a sensor array that reads contact points and their position as well as grip forces on each sensor.

The driving pattern of drivers from a group are evaluated and scored. Using cutoffs or selection criteria, expert drivers are chosen from this group, and their driving pattern is used to train vehicles to become autonomous or enhance their autonomous capabilities. Evaluation can be done under varying operating conditions, on segments or whole paths. The vehicles can be real vehicles operated by humans or non-humans (autonomous vehicle software) on real world segments of paths, or virtual vehicles (on a screen) operated on virtual world segments or segments of real-world paths that have been recorded by video cameras.

BRIEF DESCRIPTION OF DRAWINGS

FIGS. 5a, 5a1 show parts of a human eye.

FIG. 5b shows the axes of the eye.

FIG. 5c shows different types of reflections from an eye.

FIG. 5d shows visual field of an eye.

FIG. 6a shows the image of an eye illuminated by an IR source.

FIG. 6b shows an arrangement of crosshairs on the driver's seat to account for thermal drift.

FIGS. 7a, 7b show a binaural recording dummy head.

FIG. 7c shows the placement of microphones inside the dummy head.

FIG. 7d shows a variation of the binaural device that is truncated above and below the ears.

FIGS. 8a-8c shows examples of placement of binaural microphone devices.

FIGS. 9a-9e show hand contact area and grip sensing devices and their details.

FIGS. 10a-10h show foot position sensing concepts.

FIG. 12b shows the image acquired by the setup of FIG. 12a.

FIGS. 14a-14c1 show various arrangements of frame mounted eye and sound imaging systems.

FIG. 15a shows a scenario of eye movement data being used to train a vehicle to improve its autonomy.

FIG. 15b shows eye movement data of FIG. 15a.

FIG. 16 shows a scenario on a road with an approaching ambulance.

FIG. 17 shows a scenario on a road with a child at the edge of the road.

FIGS. 19b, 19b1, 19b2, 19b3 show a scenario on a road with a child on a bicycle at the edge of the road, and the saccades/fixations of the associated ROI.

FIG. 19c shows a scenario on a road with a ball rolling onto the road.

FIGS. 19d1-19d3 show a scenario on a road with a kangaroo crossing the road.

FIG. 24 shows aspects of a typical signature.

FIG. 25 shows a signature categorization scheme.

FIG. 27 shows non-event categories.

FIG. 28a shows a scheme to categorize and score failure and success of a subject.

FIG. 29a1 shows a second scheme for obtaining event and non-event value arrays for a segment.

FIG. 30c shows data arrays used to score and rank subjects.

FIG. 30d shows scaling factors associated with the arrays of FIG. 30c.

FIG. 37 shows an example ED identification scheme used to develop a platform to facilitate improving autonomous vehicle software.

DETAILED DESCRIPTION OF THE INVENTION

When examples and embodiments are described to be related to vehicles, these vehicles can include land, air, space, water vehicles, including wheeled, tracked, railed or skied vehicles. Vehicles can be human-occupied or not, powered by any means, and can be used for conveyance, leisure, entertainment, exploration, mapping, recreation, rescue, delivery, fetching, and provision of services, messenger services, communication, transportation, mining, safety, or armed forces. Vehicles can be operated in a range of modes. They can be fully under the control of a human, which is the case for non-autonomous vehicles; they can be fully autonomous, without the need for human intervention, assistance or oversight; or a range of types in between, which can be broadly termed semi-autonomous. Non-autonomous vehicles require a human operator, whereas fully autonomous versions do not require a human operator. All examples of vehicles appearing in this disclosure have automatic transmission, and they have no clutch pedal, just accelerator and brake pedals that are both operated by the same foot. However, this disclosure can be non-inventively modified by skilled artisans to be used in manual transmission vehicles. This disclosure can be adapted to be used in non-wheeled vehicles.

Figure 1:
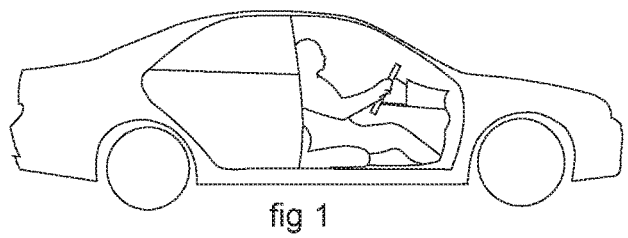
FIG. 1 is an example of a prior art non-autonomous vehicle.

FIG. 1 is an example of a non-autonomous vehicle. Here, a human operator is driving a car. The steering wheel is on the right hand side (right hand drive—RHD), the traffic pattern is left hand traffic (LHT). The human driver has control of all functions, including steering, braking, acceleration, signaling (turn indicators, emergency indicator), lights (high and low beams), windshield wipers, vehicle atmospheric control (ventilation, heating, cooling, humidity control, defrosting). The car can have features like cruise control and anti-lock braking system (ABS), but these are not considered to contributing to vehicle autonomy in this disclosure.

Figure 2:
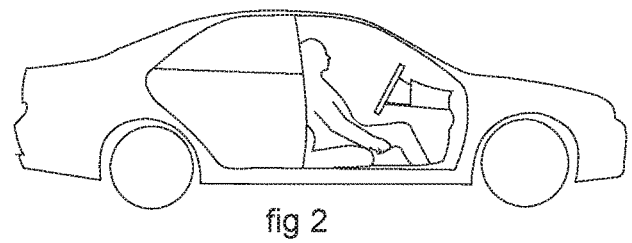
FIG. 2 is an example of a semi-autonomous vehicle.

FIG. 2 is an example of a semi-autonomous vehicle. Here, a human occupant is sitting in a RHD car in front of the steering wheel. The car's Autonomous Control System (ACS) has control of most functions, including steering, braking, acceleration, signaling (turn indicators, emergency indicator), low beam headlight, windshield wipers. The occupant's intervention, assistance, or oversight is only required in certain situations, for example, in unfamiliar, unexpected, unmapped, abnormal, emergency or malfunctioning situations, or when a potentially dangerous or illegal situation might arise.

Figure 3:
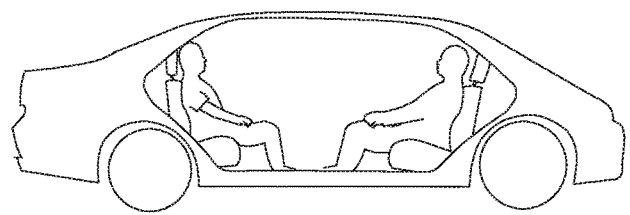
FIG. 3 is an example of a fully autonomous vehicle.

FIG. 3 is an example of a fully autonomous vehicle. Here, human occupants are sitting in a car. There is no visible steering wheel. The car's ACS has control of all functions, including steering, braking, acceleration, signaling (turn indicators, emergency indicator), low/high beam headlight, windshield wipers, and defroster. The occupants' intervention is limited to emergency situations, wherein an emergency alert can be sent, or the car can be made to perform a subroutine like slowing down and stopping at the nearest safe location. Such situations can include, for example, during abnormal, emergency or malfunctioning situations. Emergency maneuvers can be performed automatically, or manually, for example, by pressing a button, or choosing from a list in a menu. Optionally, a normally stowed steering can be accessible. Driving skills are not required for most of these procedures or maneuvers.

Figure 4B:
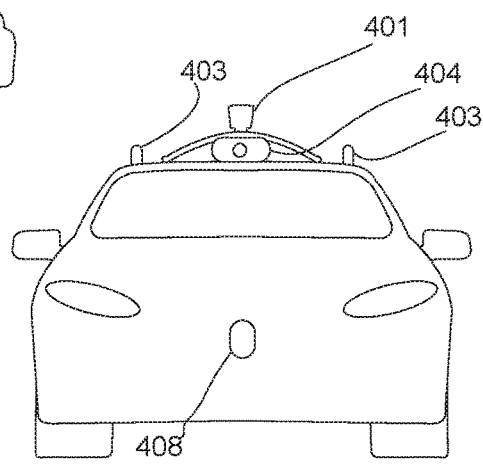
FIGS. 4a, 4b show different views of a trial autonomous vehicle with traditional sensors.
Figure 4A:
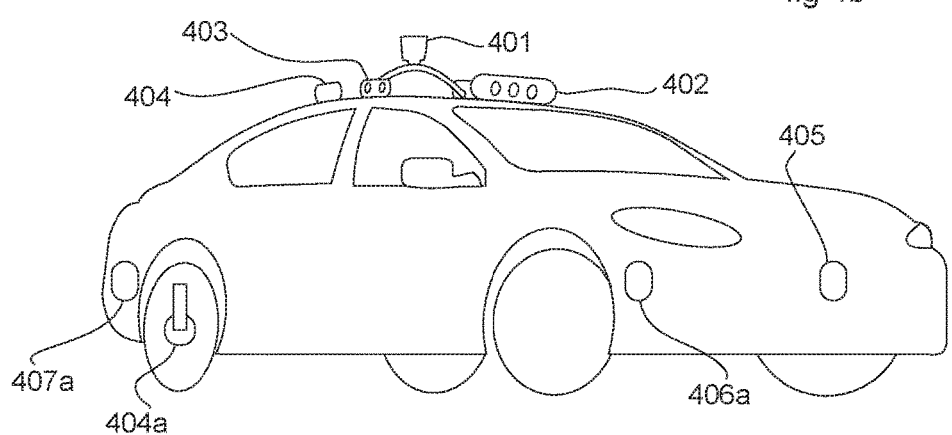

FIGS. 4a, 4b show different views of a trial autonomous vehicle with traditional sensors. Lidar 401 uses pulsed laser light (of infrared wavelengths) to illuminate a scene and measure the reflected light pulses to create a 3D representation of the scene. The front camera array 402 can have one or more visible wavelength cameras. In the example shown, there are three visible wavelength cameras in the front camera array, each camera having an approximately 60 degree horizontal field of view (fov), for a total of 180 degree coverage. The array can optionally have an IR camera (not shown) with a wide-angle lens. The side camera arrays (403) each can have a single visible wavelength camera having a field of view of 60 degrees horizontal fov, and can additionally have an IR camera (not shown). The side cameras can be rotated about 30 degrees to avoid overlap with the front cameras, or the overlap can be electronically removed. The back camera array (404) can have a single visible wavelength camera having a fov of 60 degrees horizontal, and can additionally have an IR camera (not shown). In essence, the vehicle can have 360 degree horizontal coverage in the visible wavelength using 6 cameras. However, this arrangement can be varied. For example, the front array can be made to have 3 cameras with, the middle one having a 30 degree fov, and two 60 degree fov camera on either side, and wideangle cameras on the side and back so that, taken together, all the cameras provide a 360 degree fov. For acquiring stereo images, the camera counts can be doubled, and placed appropriately. The vehicle can include long range (405), medium range (406a on one side, the other side not visible and not shown) and short range (407a on one side, the other side not visible and not shown) radars systems. These radars map information from nearby and far objects (for example, up to 200 meters) related to the objects' velocity, size and distance. Ultra wide-band radar systems can also be used. Ultrasonic sensors (404a on one side, the other side not visible and not shown, but is on the rear left wheel) sense the position of nearby objects.

Since the human eye is one of the most used, useful, versatile and powerful sensors, a discussion of the eye relevant to this disclosure is provided. FIGS. 5a, 5a1 show details of a human eye. The outer part of the eye includes three concentric portions: Cornea (501), Iris (502), and Sclera (503). The border of the cornea with the sclera is the limbus. The iris controls the diameter and size of the pupil (504) and determines the color of the eyes. Pupil diameter is adjustable and controls the amount of light passing through it into the lens (504a). Pupillary constriction is thrice as fast as dilation. Pupillary size or the movement of the iris does not form part of eye movements in this disclosure. The retina (505) is the light sensing part of the eye, and has photoreceptor cells, of which cones comprise 6% and rods 94%. Rods and cones in the retina converts light falling on them into electrical signals, which are then sent through the optic nerve to the visual cortex in the brain for processing. The blind spot is the retinal area to which the optic nerves attach, and has no photoreceptors.

Unlike rods, cones provide color vision. Rods have a low spatial acuity but are better at scotopic vision (imaging in low-light levels), and cones provide photopic vision with high spatial acuity. The macula (506) is an oval-shaped pigmented yellow spot near the retinal center and contains the fovea (507). The fovea is a small 1.5 mm diameter pit that contains the largest concentration of cone cells and is responsible for central, high resolution vision. Eye movements helps images of objects we want to see fall on the fovea. About 25% of visual cortex processes the central 2.5 degrees of the visual scene, and this relationship is eccentric as we move away from the fovea centralis. The fovea is rod-free, with a very high density of cones, which falls off rapidly away from the fovea and then levels off. At about 15°-20° from the fovea, the density of the rods reaches a maximum.

Medial commisure (508) and lateral commisure (509) are the two inner corners where the eyelids join. Palpebral fissure is the opening between the eyelids. Canthal or commisural tilts are the angles between the lateral and medial commisures, with positive angles associated with the lateral aspect being above the medial. The lacrimal caruncle (510) appears lateral to the medial commisure.

Eye movements alter the three-dimensional orientation of the eye inside the head and are controlled by three pairs of muscles to cause horizontal (yaw), vertical (pitch), and torsional (roll) eye movements. Eye orientation uniquely decides gaze direction. FIG. 5a1 shows two such muscles: the superior oblique muscle (511) and the inferior rectus muscle (512).

FIG. 5b shows the axes of the eye. The visual axis is indicated by (516). Illumination along the optical axis (515) (on-axis illumination) will cause light to be retroreflected from the retina, causing the pupil to appear brighter than the surrounding iris—similar to red-eyes in flash-photography, and is called the bright-pupil effect.

FIG. 5c shows different types of reflections from an eye which is illuminated by a light source. Light entering the eye (517) is refracted and partially reflected at various layers. Reflection occurs at the outer corneal surface (called the first Purkinje: P1, this is the brightest), inner corneal surface (second Purkinje: P2), outer lens surface (third Purkinje: P3) and inner lens surface (fourth Purkinje: P4).

When looking at a person's eyes, the reflection we see on the eye is from the cornea (P1). When imaging with a camera, infrared light can be used to illuminate the eye so that this IR light returning from the eye is selectively imaged, while the visible spectrum is muted or discarded. Corneal reflection P1 of the illumination source appears as a spot. Iris reflection is dark (but has color information). The pupil commonly appears dark in the eye image when using off-axis illumination. In this case, light reflected from the retina is not imaged by the camera and therefore the pupil appears as a dark circle against the surrounding iris. This arrangement is more pupil diameter variation tolerant than bright-pupil imaging.

However, retinal retroreflection has strong direction dependence and can be bright at angles closer to normal causing the pupil to be bright. In this disclosure, unless otherwise specified, both the first Purkinje P1 (corneal reflection) and the pupil are detected and used for analysis of eye movements, and dark pupil imaging is used.

When using pupil-corneal reflection systems, calculation of the pupil center can be skewed by descending eyelids, downward pointing eye lashes, and use of mascara. To alleviate these issues, algorithms can work with the following assumptions: both the iris and pupil are roughly ellipsoidal; the pupil is centered inside the iris; the pupil is darker than the iris, which, in turn, is darker than the sclera.

FIG. 5d shows a diagram of the visual field including the fovea, parafovea and peripheral vision regions with an exemplary degree of the visual field that the regions can see. The fovea (507) occupies 5 degrees of visual field and is 1.5 mm in diameter, and provides the sharpest vision; the parafovea (520) previews foveal information, and is 2.5 mm in diameter. The perifovea (521), which is 5.5 mm in diameter, has the lowest sensitivity in the macula (506). Peripheral vision is the region beyond the perifovea, and extends to about 105 degrees each on both sides of the visual axis. Peripheral vision has three regions: near (30 degrees from visual axis), mid peripheral (starting at 30 degrees and extending to 60 degrees from visual axis), and far peripheral. Peripheral vision is sensitive to flashing objects and sudden movements. Peripheral vision has approximately 15-50% of the acuity of the fovea and it is also less color-sensitive. When fixated on a scene, eyes are oriented so that the center of the image of the scene falls on center of the fovea, which is called the point of gaze (POG). A human face can be recognized as a face in the mid to near peripheral vision, with the ability to detect facial features becoming greater towards the fovea.

Eyes move during a majority of the time when awake. When looking at a scene, human eyes move around, rather than being fixed in a position. This movement locates regions of interest (ROI) in the scene to help the brain create a multi-dimensional map. For example, when looking at a (two-dimensional) photograph, the eyes make jerky but fast movements called saccades, and momentarily stop at several points called fixations. When looking at a scene on path of travel, for example a crowded city road, a three-dimensional map is created. Monocular eye movements are called ductions. Movement nasally is adduction, temporal movement is abduction, elevation is sursumduction (or supraduction), depression is deorsumduction (infraduction), incycloduction (intorsion) is nasal rotation of the vertical meridian, excycloduction (extorsion) is temporal rotation of the vertical meridian.

Binocular eye movements, wherein the two eyes move in the same direction, are called conjugate movements or versions. Dextroversion is movement of both eyes to the right, levoversion is movement of both eyes to the left, sursumversion (supraversion) is elevation of both eyes, deorsumversion (infraversion) is depression of both eyes.

Depth perception (stereopsis) is extracted from binocular disparity (disjugacy), wherein the difference in image location of an object seen by the right and left eyes is caused by the horizontal separation (parallax) between the eyes. Vergences are simultaneous movements of both the left and right eyes in opposite directions (which can be converging or diverging) to provide single binocular vision. These disconjugate movements prevent double vision (diplopia) when a foveated object moves in space, for example, from a far distance to closer to the eyes. When moving left to right, a temporal non-syncrony can occur, wherein the abducting eye moves faster and longer than the adducitng eye, with this misalignment being corrected at the end of a saccade through glissades and drift. Most humans have a dominant eye, which may be directed in a different direction from than the passive eye.

Fixation is when the eye temporarily stops at a location while scanning a scene. Fixations allow re-positioning of the fovea over ROIs to acquire and compose higher resolution information in conjunction with the nervous visual processing system. The range for fixation durations is 0.1 to 1 second, typically 200-600 ms. The typical fixation frequency is less than 3 Hz. Fixations are not complete stillness, but can include three micro-movements: tremors, microsaccades (to quickly bring eye back to its original position), and drifts (slow movements taking the eye away from fixation center), or very low gaze velocities (below 10-50 degrees per second).

Saccades are rapid movement of the eye between fixation points, and are events where the eyes move fast and ballistically, with durations in the range 20-100 milliseconds, during which period we are blind. Saccadic velocities can be in the 20-500 degrees per second range, with some peak velocities of up to 900 degrees/second. Saccades are rarely a straight line between two points, they take several shapes and curvatures. The end of a saccade is not abrupt—the eye wobbles before stopping. This post-saccadic movement is called a glissade, and does not appear at the beginning of a saccade. They are used to realign eyes before a steady fixation. This settling is similar to a precision motion controlled closed-loop stage settling when at destination leading to positional "ringing".

The time between a stimulus and start of a saccade is the saccadic latency, which varies depending on the saccadic amplitude that follows, and is usually in the range of 100-350 ms. For a 5-10 degree saccade, the latency can be 200 millisecond. Refractory periods between saccades can be built into saccadic latencies or identified as being distinct periods in cases of very short or an absent inter-saccadic fixation, for example, when another saccade is required to be performed immediately following a saccade. Additional requirements can be set in the software interface for detection of saccades, for example: clear peaks, maximum velocity.

Smooth pursuit are slow motions of the eye as it follows a moving target, for example, an airplane in the sky. During smooth pursuit, the gaze position can lag the target, and the eye makes catch up saccades to re-foveate the target. Overshoots are corrected using back-up saccades, while leading saccades are anticipatory saccades. Velocities of smooth pursuit increases with straighter paths.

Square-wave jerks are conjugate saccadic intrusions in the eye movement while tracking a target that causes the eye to lose tracking position and then restores it. They consist of pairs of small saccades in opposite directions which are separated by saccadic latency.

Dwell has a specific meaning in this disclosure—it is the time spent in one region of interest (ROI). Dwells have starting and ending points, durations and dispersions, but are different from fixations because their temporal and spatial extents are larger than fixations. Transitions are gaze shifts used to move from one ROI to another. In one-way transitions, and unlike two-way transitions, gaze does not return to the same ROI right away. Gaze revisits occur when gaze returns to the same ROI, but after other transitions have occurred in between. Attention maps show the spatial distribution of data. An example is a dwell map, which is a pictorial illustration of all ROIs with a dwell time over a threshold. While viewing a dynamically changing image like a car driving along a crowded city street, the ROIs are dynamically changing. The attention map of the traversed path will have dynamically changing ROIs, and therefore have dynamic attention maps indicating dynamically changing heat and dwell times Tremor has a specific meaning in this disclosure—it is a fixational eye movement of amplitude less than 1 degree, and peak velocities of around 20 second/sec.

Blinks are events surrounding the time period when the eyelid is closed, and can be algorithmically defined as loss of positional signal for a threshold duration in combination with eye movement distance data loss, for example, 50-100 ms over 10-20 degrees. During blinks amongst much of the population, the descending upper eyelid covers most of the cornea. Blink durations increase with drowsiness, alcohol levels, schizophrenia and similar disorders. In this disclosure, blinks and pupillary dilation are not considered a part of eye movements—unlike saccades, glissades, microsaccades, tremors, dwells, smooth pursuit, and square-wave jerks. Although blinks can be recorded, they are used to determine the cause of discontinuity or anomalies in data that are not explainable by eye movements. To reiterate, blinks and iris movement/size changes or pupillary dilation do not form a part of eye movements in this disclosure.

Eye-in-head fixations occur when the eye is not moving relative to its socket, for example when the head is moving along with the stimulus. Eye-on-stimulus fixations occur when the eye is fixated on the stimulus, but moves inside its socket to track as well as compensate for head motion. In normal driving situations, the head is free to move, and therefore both the eye and head move when tracking objects at a high angle away from the median plane of the subject. The median plane is considered to be the same as the as the central vertical plane of the steering wheel.

FIG. 6a shows a screenshot of an eye movement tracker. The eye is illuminated by an IR source, and the acquired image has a dark pupil. The cornea (601) and pupil (602) have been identified, along with the corneal reflection (601a). Crosshairs through the corneal reflection center (601b) and the pupillary center (602a) are overlaid by the image analysis system. Eye trackers are made by several companies, including SMI, Gazpet, Imotions, Tobil, ASL, SR Research, SmartEye, Seeing Machines. Binaural microphones are made by 3DIO, Roland and others.

Mounting of eye trackers can be on the subject's head, on a tower on which the subject's head is resting, or remote from the subject. A combinations of mounting schemes can also be used when required. For example, a configuration can have remote cameras and illumination, but head mounted inertial measure units (IMU) to detect head position in space. Another configuration can have dashboard/dashpad mounted illumination combined with head-mounted cameras. Apart from cameras used to image the eyes, eye tracker units can be combined with scene tracker cameras that capture the scene being viewed along or parallel to the line of sight. These trackers can be mounted on the frame, dashpad or on the outside of the vehicle. Images from the eye and scene trackers can be combined to produce gaze-overlaid images. Furthermore, using head/facial feature detection, head tracking cameras can also be added to these systems.

Most commercial eye trackers have options to adjust camera and illuminator positioning (linear and angular). Cameras can be automatic or manual focusing or require no focus adjustments. Automatic adjustment of linear and angular camera positions can additionally be carried out using feedback from the eye tracker's image analysis system. Eye movement measures can include direction, amplitude, time duration, velocity, acceleration, and time differential of acceleration. Tracing of a subject's eye movements spatially and temporally provides the scanpath events and representations, including saccades and fixations.

In non head-mounted eye tracking systems, extreme gaze angles will cause precision and accuracy deterioration in eye tracking, particularly when combined with head rotation. Multiple cameras and illuminators positioned appropriately can overcome such issues.

Eyes vary widely within the population, and also from the ideal model, because of non-uniform shapes of the eye's components (like cornea and lens) between individuals. Variation between the two eyes of the same individual is also common. Saccadic amplitudes vary within a population for the same scene or task, and also vary between the two eyes of the same subject. All of these variations can occur within the "normal" population, or can be caused by abnormalities.

Identifying and accounting for these variations will help deliver better eye-movement data. A discussion of variations and abnormalities follows, which can be used for calibration purposes whenever needed. Calibration can be carried out before the start of a path before the vehicle starts moving, or in between a path, or at the end of it. calibration can be instructive or interactive. For example, the driver can be prompted to look straight ahead, then look at side view mirrors, then the rearview mirror, then look ahead but into the sky (for infinity—least focus power of the eye's lens). Calibration can provide examples of specific pupil and corneal reflection relations to the tracker. Initial calibration of each individual's left and/or right eye can provide offset factors or equations for compensation when using a global equation based on the assumption of an ideal eye. For those wearing glasses, calibration can be made with and without glasses. Drivers can be instructed to close one eye at a time while performing calibrations. This can detect abnormalities as well as the dominant eye. Calibrations using four gaze positions can account for several non-ideal eye conditions. Lateral and medial commisures, lacrimal caruncle, and canthal tilts can also be identified during calibration, some of which can be used as landmarks or account for head/camera tilts. Visible light sources like red laser LEDs can be used to calibrate eye movement.

Drugs, alcohol, mental and physical disorders, age (very young children and very old people) will all affect eye movement. Data acquired from such subjects can be be adjusted or eliminated by identifying them as outliers. A similar situation arises with contact lenses, thick or complex lensed spectacles, heavy mascara, drooping eyelids (ptosis), squint (due to glare or laughter, for example), teary eyes and subjects with prominent epicanthic folds. If such subjects are a large subset of the general population, eliminating them can provide data that is not truly representative. When such subgroups become a significant proportion of the data population, hardware and/or software settings can be altered to utilize the data without discarding them as outliers. Pupil size changes with the amount of ambient light, drugs, cognitive load, emotional state, fatigue, age. In subjects with anisocorea, pupillary sizes, including during dilation and constriction (mydrisasis and miosis), can be different between the two eyes. Consensual is the normal phenomenon wherein both pupils constrict or dilate even when one eye is closed. Pupil size is sensitive to the angular displacement between the camera and the eye being imaged. Pupil size or changes do not form part of eye movement in this disclosure.

Crossed-eye (strabismus) is present in varying degrees in about 4% of the population, and can be esotropic (nasally convergent) or exotropic (divergent). Strabismus can be comitant (present in all directions of gaze) or incomitant (varies with varying directions of gaze), or hypertropic (vertically misaligned).

Eye trackers can have biases, noise and other statistical anomalies that are inherent to their software, hardware and optical system. Using eye trackers in moving vehicles can compound this due to mechanical vibration, thermal cycling (and drift) and other non laboratory environments/non-deal settings. Using artificial eyes or targets fixed in position can help detect and account for these issues when analyzing acquired data (for example, by using software filters and offsets), and thereby improve accuracy, precision and confidence. This can also be used for startup and intermittent calibration, and camera alignment. For example, FIG. 6b shows crosshairs (610) mounted on the driver's seat and projecting beyond the driver so that they can be imaged by a camera mounted on the dashpad. Averaging data from the two eyes of the same subject can substantially improve precision. However, this comes at a cost, for example, in terms of loss of information related to vergences. Filtering and de-noising functions can be used to overcome these.

If the head were constrained from moving, and only the eyes are moving within their sockets, a single camera and single infrared source can be used for detecting eye movements. Multiple cameras and IR sources can be used for better results if head movement is allowed. Sampling frequencies (frame rate per second) of currently available lower-end cameras start at 50 Hz, and the higher the sampling rate, the better the quality of results, particularly when analyzing saccades, glissades, tremors and microsaccades.

In commercially available software, parameter settings are used to identify specific events and separate them. These parameters include sensitivity settings for each category of events, saccade-onset, steady-state and end-velocity threshold, and acceleration threshold. Since different manufacturers use different algorithms, hardware and software settings, these parameters are not universally applicable. In many instances, the user interface is simplified to provide a few descriptive settings like low, medium, and high.

Algorithms used to extract events from eye movement data can detect gaze position, velocity, acceleration and jerk, each of them being the time derivative of its predecessor.

In an embodiment, dispersion algorithms are used to detect fixations without using velocity and acceleration data to extract fixation onset and offsets. In an embodiment, probabilistic modeling of saccades and fixations are carried out using Hidden Markov Models. In an embodiment, detection of events relating to gaze, fixation, or saccades to near objects, like control buttons on a vehicle's steering, is carried out by identifying events where glissadic movements are different for each eye of the subject, but where microsaccades occur in both eyes at almost the same time.

During a backtrack, a saccade following a previous saccade occurs in the opposite direction. Look-aheads saccades allow gaze to shift and fixate upon objects that will soon need to be used in some way. This is contrasted with saccading to other objects that may be used in a future planned action, for example, saccading to a radio knob on the dashboard of a vehicle to increase its volume. Ambient processing involving longer saccades and shorter fixations are used to scan the important or critical features of a scene first, followed by focal processing for detailed inspection using shorter saccades and longer fixations within regions. Target selection along a scanpath is guided by past experiences and memories of driving under similar conditions, or similar paths, or the same path, which also avoid revisits of earlier targets that are inconsequential. For example, consider a driver driving home at 6 pm from a his place of work, which he has been doing for the last 5 years as a matter of routine. He will ignore most traffic signs. Although he sees them in his peripheral vision, he will not foveate/saccade to them. However, he will pay attention to traffic lights, saccading slower to the lights because of their expected presence. Saccades will be reduced in number and saccadic velocities reduced (when compared to driving though an unfamiliar path), while fixations and their durations will increase.

In an embodiment, when there is negligible or no intersaccadic dwell or fixation between two saccades, and the first saccade's travel was greater than 15 degrees, the two saccades are considered to be purposed for targeting the same object but broken down into a first saccade and a second corrective saccade. As an example, this can occur when entering intersections or roundabouts, where there is a requirement to scan extreme angles to inspect traffic entering the roads ahead. A similar situation arises when entering a highway from a minor road, wherein the driver is required to check the lane ahead as well as the traffic behind. In routine driving, viewing objects away from the fovea using peripheral vision does not allow for fine-detail cognition. However, details like traffic on adjacent lanes far ahead is relatively unimportant. It is usual to search for details within close proximity to the current ROI using foveal vision, for example, close-by vehicles in adjacent lanes. When viewing a road, saccades to nearby locations can be more common after a fixation (for example, a child on a bicycle, and checking if there are adults accompanying the child), rather than large amplitude saccades to distant locations. In an embodiment, when the distances between objects are very small (on the order of 10 arcminutes, for example: a multitude of pedestrians on the sidewalk), an absence of saccades between the pedestrians is not taken as a lack of cognition of all these pedestrians by the driver, but rather advantageously devoting extra cognitive resources for the available retinal resolution in the peripheral vision and perceiving these pedestrians at lower resolution, all the while using foveal vision to perceive other, more important, objects on the road. When a subject is searching intently (as opposed to performing general overviews), or when concurrently performing other unrelated tasks, saccadic amplitudes tend to drop. Saccadic velocities decrease with drowsiness, predictable targets, older age, neurological disorders, and drug and alcohol use.

In an embodiment, when tracking objects using smooth pursuits, for example, a bird taking off from the middle of a road and flying vertically, signature detection algorithms are programmed to accommodate jumpy vertical smooth pursuits. In contrast, this is not the case for horizontal smooth pursuits, for example, when a ball rolls across the road.

In an embodiment, a specific instance of a table listing settings for threshold and cutoff values for a program having a set of subroutines suited to a particular scenario, imaging and sensor hardware, software and hardware setup is given below. These settings can change from instance to instance.

| Type | Duration ms | Amplitude | Velocity |
| --- | --- | --- | --- |
| Fixation | 100-700 | — | — |
| Saccade | 30-80 | 4-20 degrees | 30-500 degrees/sec |
| Glissade | 10-40 | 0.5-2 degrees | 20-140 degrees/sec |
| Smooth pursuit | — | — | 10-30 degrees/sec |
| Microsaccade | 10-30 | 10-40 seconds | 15-50 degrees/sec |
| Tremor | — | <1 degree | 20 second/sec peak |
| Drift | 200-1000 | 1-60 seconds | 6-25 seconds/sec |

FIGS. 7a, 7b show front and side views of a binaural-recording mannequin-head having a microphone (not shown) in each ear at the end of their ear canals (701). The head can be made of plastics or composites, while the pair of life-like ear replicas are made from silicone. FIG. 7c shows the placement of microphones (702) inside the mannequin. The mannequin's head is similar in shape and size to a regular human head, but lacks many features like lips and eyes. It has ears that resemble the size and geometry of a human ear. The nose is a straight-edge representation of a human nose and casts a shadow of the sound. Sound wraps around the mannequin-head, and is shaped by the geometry and material of the outer and middle ear. Some of the sound is transmitted through the head. The two microphones record sound in way that, when played back, a 3-D 'in-head' acoustic experience is created. The mannequin mimics natural ear spacing and produces a "head shadow" of the head, nose and ears that produces interaural time differences and interaural level differences. Such an arrangement captures audio frequency adjustments like head-related transfer functions. FIG. 7d shows a variation of the binaural device that is truncated above and below the ears of the mannequin.

FIG. 8a shows the placement of such a truncated mannequin-head in a car above the driver-side headrest, with its nose facing the driver. A bluetooth device (not shown) within the mannequin (801) transmits the sound stream from the microphones to a recording device in the car. This recording device can be integrated with the human sensor recording system or a standalone unit which timestamps the sounds as it records it. FIG. 8b shows a whole mannequin head (802) placed on the backside of the backrest, aligned with the drivers head. The nose is above the headrest and facing the driver. FIG. 8c shows a full mannequin head (803) just as in FIG. 8a, but anchored to the roof of the car. Other possible configurations include placing the complete or truncated head on the dashpad, above the rearview mirror, on the passenger-side seat's head-rest, and on top of the driver's head (using a head-strap). A frame-mounted variation of the binaural recording device using a set of smaller ears and without the intervening mannequin-head, is shown in FIGS. 14a-14d. The outer ears and ear-canals of this frame-mounted binaural device are made of silicone, with a microphone each at the end of the ear canal.

FIG. 9a shows a steering wheel with a hand sensing mat (901) wrapped around the outer wheel. FIG. 9b shows a segment (901a) of the hand sensing mat (901). The mat has eight sensors (902) in a row (902a) along its width. The length of the mat is chosen to fit completely around the steering wheel. In the example of FIG. 9a, there are 64 sensor rows (902a) arranged circumferentially, with each row having 8 sensors. Each sensor (902) has a sensing pad that detects both contact and pressure of the palms and fingers. FIG. 9c shows an enlarged section of the mat of FIG. 9b, with a cross-section through a row of mats appearing in FIG. 9d. Each of the sensors (902) are connected to a bus (serial or parallel) (903) that is connected to a processor (not shown). All the rows (902a) are connected to this bus. Each sensor (902) has a unique address. When a sensor (902) is touched or pressed, the touch event and pressure value is sent via this bus (903) to the processor. In an example operating scheme, the steering wheel is programmatically divided into left and right halves. In FIG. 9a, the left side has 32 rows of 8 sensors (for a total of 256 sensors), and the right side the same. Therefore, there are a total of about $1.158 \times 10^{77}$ unique combinations. To derive a simpler correlation, the rows can be numbered 1 to 32. An example of hand sensing information obtained during casual driving of a right hand drive (RHD) car at constant speed along a particular segment of a path on a highway with wide roads and very little traffic, where the highway is fenced, has a central divider, with three lanes in each direction is represented as: {[−34.82088284469496,149.38979801139794]; [t10:32:28]; Left=[y(12), x(2, 3, 4, 5, 6, 7), p(3, 3, 3, 2, 1, 0)]; [y(13), x(3, 4, 5, 6), p(3, 2, 2, 1)]; [y(14), x(4, 5), p(1, 0)]; [y(15), x(4)], p(0); Right=[ ]}. This data point indicates that at the recorded latitude, longitude and time 10 hrs, 32 min, 28 sec, the left side of the steering wheel was contacted at row 12, sensors 2, 3, 4, 5, 6, 7 with pressure on these sensors of 3, 3, 3, 2, 1, 0, respectively. A similar interpretation applies for the remaining y, x, p values. The zero in the pressure data indicates no pressure is being applied, but there is contact. Pressure values are dimensionless, with a range of 0-7, the highest value indicating extreme squeezing of the steering wheel. R=[ ] is a blank data set indicating that the right side of the steering has no contact with a hand (right side of the steering wheel is not being held). For a very simplified understanding of this dataset, the pressure values can be added: [(3+3+3+2+1+0)+(3+2+2+1)+(1+0)+(0)]=21 to indicate that the left hand is engaging the steering wheel at pressure 21 at the particular location and/or time, whereas the right hand is not holding the steering wheel. This can indicate a relaxed, simple and familiar driving situation where the driver is not required to be very alert. This situation can be contrasted with driving in a crowded city road that is un-fenced, undivided, with a lot of pedestrians on the sidewalks, bicycle lanes, traffic lights, intersections, frequently stopping vehicles like buses. The driver in such a situation is much more alert and cautious, with both hands on the steering wheel, gripped tighter than the usual. If the driver is new to the city and this traffic pattern, the level of alertness and caution will be even greater, and the grip on the steering wheel tighter. Another version of a simplified reading on the steering wheel ESCAF (Easy Steering Contact Area and Force) can be of the form ESCAF=(L[0.3][0.2]; R[0.6][0.4]), which indicates that the left hand has a total contact area 30% of the nominal full contact area and 20% of the nominal maximum grip force. The nominal full contact area and nominal maximum maximum grip force are mean values of three attempts when the driver was instructed to grip the steering wheel tightly and with full contact of palm and fingers of one hand at a time during startup or calibration. Calibration can be performed by asking the driver to perform different operations, for example, holding the steering with both hands without squeezing, then full squeeze with both hands, or one hand at a time with maximum contact and squeeze, or one at a time with normal contact and squeeze.

FIG. 9e shows a variation of the hand sensing device. Many drivers hold the steering wheel with their palms and fingers on the steering wheel's ring portion and their thumbs resting on the spoke portions. To sense fingers/thumbs on the spoke portion, additional sensor mats (901a, 901b) are wrapped around on each of the spoke portions adjacent the ring. In FIG. 9e, each side of the ring-spoke intersection has 8 rows of 4 sensors each.

When the vehicle is being turned steeply using the steering wheel, for example, at a left hand turn at a 4 way intersection in LHT, the turning action by the driver will cause the gripping of the opposite sides as the steering wheel is rotated (as the turn progresses). This pattern can be detected by algorithms, and used appropriately (for example, to detect sharp turns), or the dataset can be discarded if not appropriate for the present computation.

FIGS. 10a-10h show foot position sensing concepts. FIG. 10a shows the inside of a LHD car with accelerator (1001) and brake (1002) pedals. FIG. 10b shows a close up of modified accelerator and brake pedals, each having a proximity sensor (1001a, 1002b) mounted on them. Proximity sensors can be any one of those known in the art, including capacitive, light, ultrasonic or time-of-flight (TOF) type. For example, the VL6180 TOF sensor made by ST-Microelectronics can be employed. FIG. 10c shows another example of the foot position sensing concept. Here, there are two sensors (1003a, 1003b) on the brake pedal and two sensors on the accelerator pedal (not shown). Only the brake pedal is illustrated in this figure. The distances measured by the brake pedal sensors (1003a, 1003b) are dbp-foot (1004a) and dbp-wall (1004b), respectively. Similarly, FIG. 10c1 shows the distances measured by the accelerator pedal sensors (1003c, 1003d) are dap-foot (1004c) and dap-wall (1004d), respectively. It is to be noted that dbp-wall and dap-wall are set to a value of zero when not being depressed, which is not apparent from FIG. 10c, FIG. 10c1 (which show the actual distance between the pedal and wall). This can be done during calibration of the pedals at startup. When the pedals are depressed, dap-foot and dba-wall will actually return the values of how much they are depressed, not their distance from the wall.

FIG. 10d shows an arrangement with three TOF sensors on each of the brake and accelerator pedals, two on the front face and one on the backside (this backside sensor is not shown) facing away from the driver. Having two sensors on the front surface allows enhanced mapping of the foot by performing one or a combination of mathematical operations on the measurements performed by these front sensors. These operations can include: averaging, using data from the sensor that is currently providing the highest value, using data from the sensor that is currently providing the lowest value. Furthermore, a calibration step can be incorporated during startup of the vehicle, where the driver is prompted to perform various operations to obtain baseline values. These operations can include: asking the driver to move the foot over from the brake to the accelerator pedal, then rest the foot on, but not depress, the accelerator pedal, then the same operation for the brake pedal, then depressing each pedal (while the vehicle is in park mode).

FIGS. 10e-h shows the principle of operation of the foot sensor, with the both the pedals having two sensors each as described for FIG. 10b. In FIGS. 10e and 10f, the foot is on the accelerator and brake pedals, respectively. The proximity sensor on the pedals on which the foot is on will now record its lowest value. When an anticipation of braking arises, for example, when driving a car and an unaccompanied child is seen 200 meters ahead, standing by the edge of the road and facing the road, the foot goes off the accelerator and moves over the brake pedal, hovering about 8 cm over it as in FIG. 10g (only brake pedal shown). As the car approaches closer and is 100 meters from the child, the foot gets closer to the brake pedal, and is now 4 cm over it. At 75 meters, the foot is on the brake pedal, but not depressing it, as in FIG. 10h (only brake pedal shown). At 50 meters from the child, the brake pedal is slightly depressed to slow the car. The foot remains on the pedal until after crossing the child, and immediately removed from the brake pedal and the accelerator pedal is depressed.

When the brake or accelerator pedals are not depressed, dbp-wall=0 mm, and dap-wall=0 mm. When the foot is on the accelerator pedal, it can not be hovering over the brake pedal, and therefore dbp-foot=x, where 'x' denotes that a value is not present. Similarly, when the foot is on the brake pedal, it can not be hovering over the accelerator pedal, and dap-foot=x. A simpler notation EPO (Easy Pedal Offsets) is used, where EPO=[dap-wall, dap-foot, dbp-wall, dbp-foot], the values being in millimeters. For example, EPO=[15, 0, 0, x] represents the foot pressing the accelerator pedal by 15 mm. As an example of foot and accelerator dataset for a short segment in a path, consider a driver driving a car through a suburban area having residential houses and schools during a school day and school hours. Assume sample data capture starts at time t=0 seconds. The foot is on the accelerator pedal to keep it at a constant speed of 50 km/hour, and this continues for 30 seconds. During this period, dap-foot=0 mm, dap-wall=7 mm, dbp-wall=0, dbp-foot=x, which means that the foot is on the accelerator pedal and depressing it by 7 mm, and therefore EP=[7, 0, 0, x]. As the car approaches a school zone, the foot goes off the accelerator and depresses the brake pedal by 5 mm to reduce the speed to the legal speed limit of 40 km/hour, which occurs for 4 seconds. During this period, EPO=[0, x, 5, 0]. This is an expected pattern of driving, and can be compared with the map, which will similarly indicate a school zone with reduced speed requirement. However, after entering the school zone (at t=35 seconds), it always is a possibility that children will dart across the road. The foot is therefore mostly hovering over the brake pedal, particularly when getting close to the entrance of the school, in anticipation of needing to brake to avoid children darting across the road. At t=37 seconds, EPO=[0, x, 5, 0]. Just after t=37 seconds, the driver notices a small child on a bicycle exiting the gates of the school and driving towards the road. There is a possibility that the child is not paying attention to traffic, and may enter the road ahead. At t=39 sec, the foot depresses the brake pedal for 2 seconds to slow the car down to 20 km/hour. For these 2 seconds, an alternate representation is: EPO(39-41)=[0, x, 0, (5-12), which means dbp-wall=5 mm at 39 sec and 12 mm at 41 sec. This sequence of values from t=0 to t=41 values can be stored in a file along with geolocation/GPS and timestamps. The average of such data sequences collected by several different drivers over several days can be used as a training file for an AV. Data from the training file will indicate school days and hours because of the behavior of drivers, and also the average speed to be followed, and also the speed profile for the section of the segment of the path.

Figure 11A:
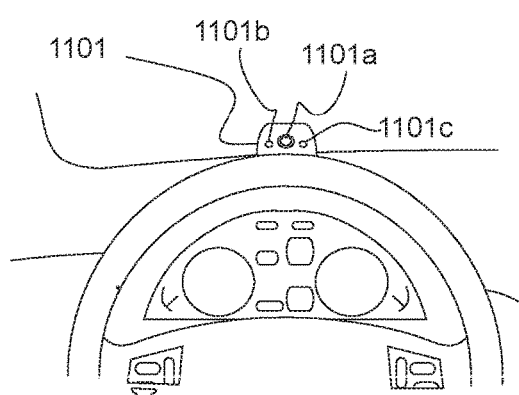
FIGS. 11a-11c shows the inside of a car with various arrangements of cameras and IR illumination sources.
Figure 11B:
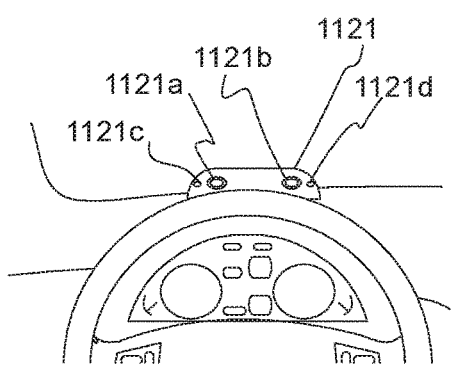
Figure 11C:
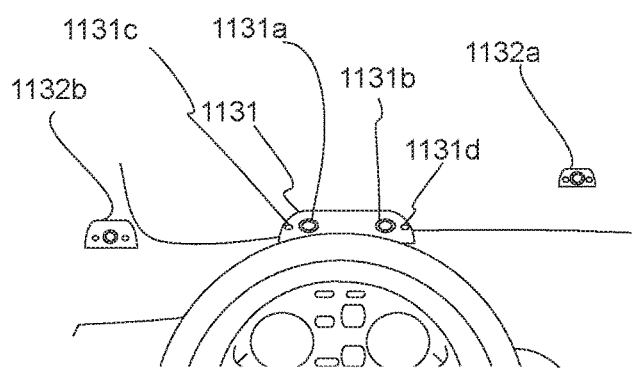

FIGS. 11a-c shows the inside of a car with various arrangements of cameras and IR illumination sources for eye movement tracking. FIG. 11a shows the inside of a non-autonomous car being driven through a path by a driver. The car is equipped with GPS, inertial measurement unit (IMU), LIDAR, radar, outside cameras, inside cameras and other outside environment and vehicle sensors shown in FIG. 22. The inside cameras track the subject's eye movements and head movements. The video data stream is saved with time and geolocation stamps. The saved stream is then analyzed by an image processing system to extract event information, including saccades, microsaccades, glissades, tremors, fixations, and drift. A map incorporating the path's roads, timestamps, geolocation, speed profiles, driver behaviors (lane changes, turn indicators, braking, accelerating, foot going off the accelerator pedal and moving/hovering over the brake pedal, vehicle behaviors (turning radius etc) is created. In FIG. 11a, the car has one imaging device (1101) on its dashpad. The device is closer to the windshield than the edge of the dashpad. The device has one camera (1101a) and two IR illumination sources (1101b, 1101c). The center of the steering wheel is on the same plane as the sagittal plane of the driver, and the center of the camera is co-incident with the plane that connects the sagittal plane with the central axis of the steering wheel. FIG. 11b shows an arrangement with an imaging device (1121) placed on the dashpad and having two cameras (1121a, 1121b) and two IR illumination sources (1121c, 1121d). The two cameras are each offset from the central axis of the steering wheel by 4 cm. FIG. 11c shows an arrangement with an imaging device (1131) having two cameras (1131a, 1131b) and two IR illumination sources (1131c, 1131d), and two additional cameras (1132a, 1132b), with these additional cameras having two IR illuminators for each (not labeled in the figure). The two central cameras are each offset from the central axis of the steering wheel by 4 cm each, while one of the additional cameras is placed below the central axis of the rearview mirror, and the other is placed along the central horizontal axis of the driver-side sideview mirror, and at an elevation lower than the other cameras.

FIGS. 12a-f shows the inside of a car with various arrangements of phone cameras. The cameras of FIGS. 12a-12f can have a clip-on filter (an example appears in FIG. 12c) whose transmission wavelength matches the illumination source wavelength. For example, if the phone's screen were programmed to display a narrowband blue wavelength, then the filter's transmission characteristics would match the same color. The filter can be of any type, including absorption and reflectance. Examples of a phone's screen color characteristics are described below with reference to FIG. 12e. In addition to (or as a replacement for) the filter, a snap-fit or clip-on lens system (single lens or multiple lens or zoom-lens) can also be added to reduce the field of view so that a much larger proportion of the driver's head is captured, thus giving a higher resolution of the eyes. Such a zoom-lens can be connected to the a system that processes the image acquired by the camera so as to make the zoom-lens auto-focus on the driver's eyes, giving a better focus as well as a higher resolution image of the eyes (by filling in more of the camera's sensors with relevant portions rather than unnecessary background). These filter and lens/zoom-lens arrangements can be adapted for front-facing as well as rear-facing cameras.

Figure 12A:
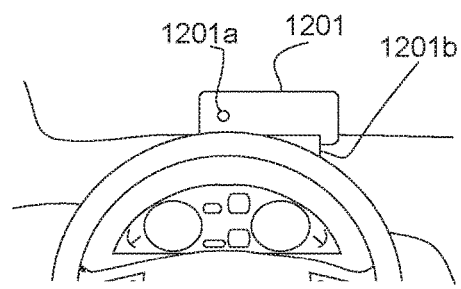
FIG. 12a shows the inside of a car with a single phone camera.
Figure 12B:
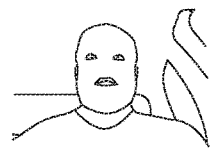

FIG. 12a shows a mobile phone (1201) with its back facing camera (1201a) facing the driver and located along the driver's sagittal plane. The phone is secured on a stand (1201b) which is on the dashpad. Phone stands/holders in all embodiment in this disclosure can have tip-tilt adjustment to help align the camera to account for the inclination/irregularities of the dashpad, angle of the windshield, driver height and placement, steering wheel height, and camera body irregularities. In the embodiment of FIG. 12a, illumination can be using ambient light, light from the phone's screen, or an external illuminator (as embodiment of external illuminator is shown in FIG. 12d), or a combination. The quality of data obtained from ambient light is much lower compared to when using pure IR illumination. FIG. 12b shows the image obtained by the phone's back-facing camera in a non-zoomed mode. The camera can be zoomed in to capture more of the face (and eyes) and less of the background, which will also improve accuracy during event extraction and provide higher quality results.

Figure 12C:
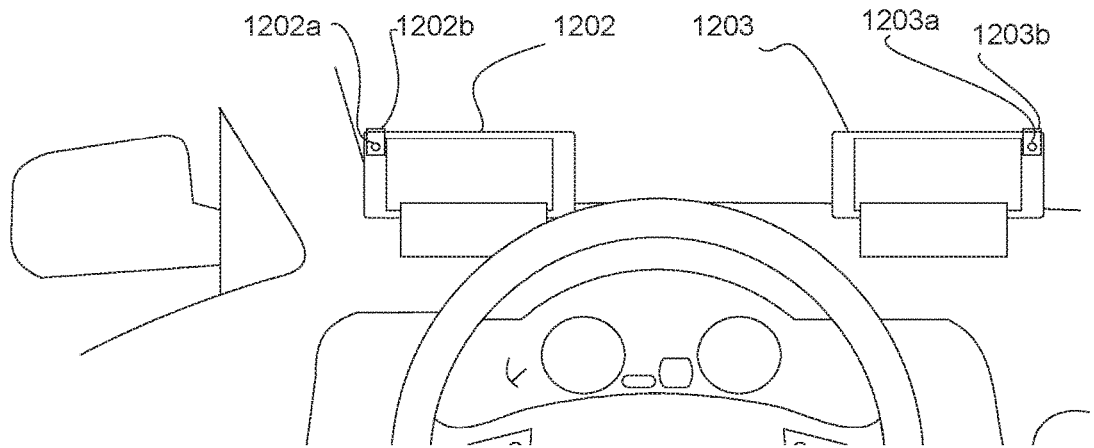
FIG. 12c shows the inside of a car with two phone cameras.
Figure 12D:
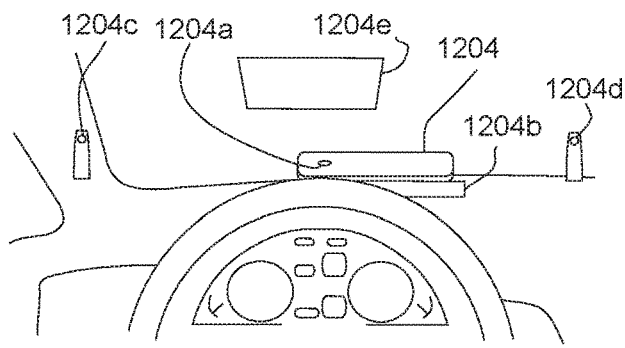
FIG. 12d shows the inside of a car with a single phone camera aimed at a windshield mounted patch.

FIG. 12c shows an imaging arrangement with two mobile phones (1202, 1203) with their front facing cameras (1202a, 1203a) facing the driver. The phones are secured on individual stands which sit on the dashpad of the car. There are no illuminators present except ambient light and/or light from the phone's screen. A clip-on filter (1202b, 1203b) as described earlier is also shown.

FIG. 12d shows an imaging arrangement with a mobile phone. The phone (1204) is lying on its back (screen facing dashpad), with its rear facing camera (1204a) facing the windscreen and located along the vertical axis of the steering wheel. The phone is secured on a base stand (1204b). Two IR illuminators (1204c, 1204d) are aimed towards the eyes of the driver. A patch (1204e) of width 15 cm and height 10 cm is affixed to the windscreen. The center of this patch is aligned with the center of the camera. The base stand (1204b) has tip-tilt adjustment. The base is adjusted such that the camera's center images the driver's forehead at a center point between the eyes. The size of the patch will be smaller the closer it is to the camera. It is wide enough to image an area that is three times the width of the driver's head, with a proportional height. The patch is optimized for full reflectance of IR wavelengths (the specific wavelength band being the band at which the IR illuminator emits light) at angles of 40-50 degrees, preferably 43 to 48 degree angle of incidence. In this imaging arrangement, the placement position of the camera (on the dashpad) and its tip-tilt setting, the placement position of the patch on the windscreen, and the height of the driver are all interrelated. The goal here is to place the path as low as possible on the windscreen, without its line of sight being obscured by the steering wheel, while at the same time centering the driver's eyes on the camera. Light from the IR illuminators is reflected from the eyes of the driver and is then reflected off the patch into the camera. The patch is made of a flexible polymer with typical thickness between 10 microns and one millimeter. Example materials include static cling films made of vinyl, PVC or PET, or adhesive films. The patch is transparent to visible wavelengths, and therefore the driver is able to see through the patch without the view of the road being obstructed. The IR reflectance can be achieved through various methods, including front surface coating of IR reflective materials (usually of sub-micron thicknesses). The patch can also be custom made for specific vehicle models, including its optimum reflection angle at the required angle, taking into account the angle of the windshield. Such customization cal also be aided by the tip-tilt arrangement of the base.

Figure 12E:
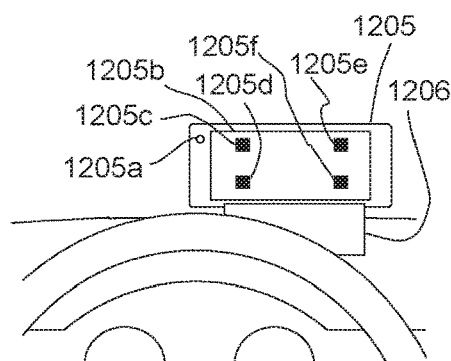
FIG. 12e shows the inside of a car with a single phone camera having illuminator patterns on its screen.

FIG. 12e shows a mobile phone (1205) with its front facing ('selfie') camera (1205a) facing the driver and aligned approximately with the center of the steering wheel. The rear facing camera (not shown) faces the road ahead. The phone is secured on a stand (1206) which is on the dashpad. Illumination is provided by the camera's screen (1205b). The screen has four squares (1205c, 1205d, 1205e, 1205f) of a particular narrowband color, while the rest of the screen is blank (black). These four squares act as illuminators. The particular color can be, for example, the wavelength of 450 nm (blue), with a narrow bandwidth of +/−15 nm. The color can be chosen to be that of the particular phone model's one of the peaks of display illumination intensity (a screen typically has multiple peak wavelengths corresponding to different colors like red, green and blue). In another example, this color can be 540 nm+/−10 nm. Generally, the bandwidth is chosen to be narrow for intensity curves around a peak that are more flattened, and broader bandwidths for intensity peaks around which the intensity curves are steep. The imaging software (of the camera) is programmed to discard (from the acquired images) wavelengths above and below the narrowband wavelengths. The advantage in this imaging setup is that eye movement tracking becomes much more sensitive because the reflections of the four squares from the eye can be captured while rejecting ambient light, including reflected ambient light. The four squares can also each have a different narrowband color, or two of the same color, or any such combination. The phone's software is programmed to cause the screen to display these specific narrowband colored squares, and the phone's imaging software (or any of the image processing systems downstream) is set to reject other colors from the images captured by the camera. Instead of being a square, the shape of the illumination areas can also be another shape, like a circle, triangle, line or a grid pattern, or other patterns similar to those appearing in FIG. 12f. The squares and other patterns can be of a size that works well with the particular zoom level. The color of the illuminator patterns can be set to change periodically, for example, change the color of each square every 0.1 second. The color of the illuminator patterns can be set to change automatically depending on the dominating ambient colors. For example, when driving through roads surrounded by greenery, the phone detects this dominance and automatically changes the color of the patterns to another color. If greenery and blue-skies are dominant, the color of the pattern is automatically changed to another color like red. Further details appear in FIG. 13e, FIG. 13f. The detection of ambient light can be performed by the smartphone itself using its ambient light detector or using its cameras (front or back facing, whichever is facing the driver), or using an external detector (the data from which can be sent to the smartphone). In an embodiment, the screen of the smartphone is blanked when gathering information about the ambient light so that the screen's light reflected from the face and body of the driver, as well as the screen's light reflected from the vehicle's interior, does not contribute to the detected light. The detected light is then analyzed for intensity and/or wavelength distribution.

Figure 12F:
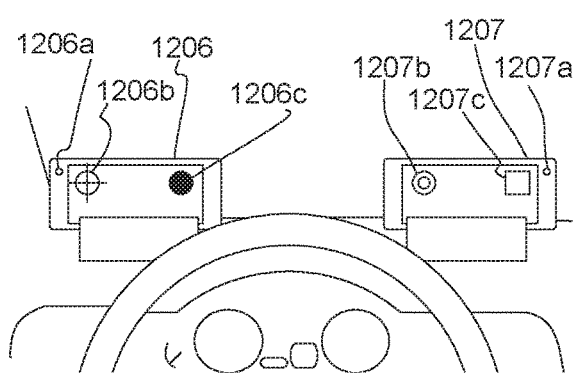
FIG. 12f shows the inside of a car with two phone cameras having illuminator patterns on their screens.

FIG. 12f shows a variation of FIG. 12e. This arrangement shows two mobile phones (1206, 1207) with front facing cameras (1206a, 1207a). Each of the mobile phones have, on their screen, different patterns. The first pattern (1206b) is a circle with a crosshair through it, and second is a solid circle (1206c), the third (1207b) has two concentric circles, the fourth (1207c) is a solid square. As with FIG. 12e, each of the patterns can have the same colors or different colors, or the crosshair can be of one color while its circle can be solid and of a different color, or the two concentric circles can each be of different colors. The patterns are generated by the phone, and the imaging software can be programmed to identify these specific patterns as reflected from the eye.

Figure 13A:
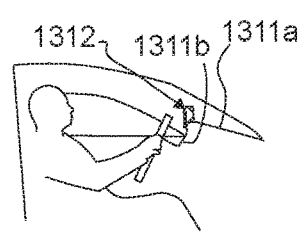
FIGS. 13a-13d show details of an embodiment of a phone camera imaging adapter.
Figure 13C:
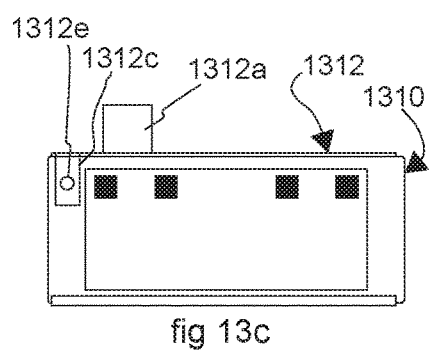
Figure 13D:
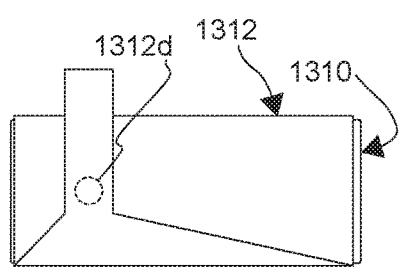
Figure 13B:
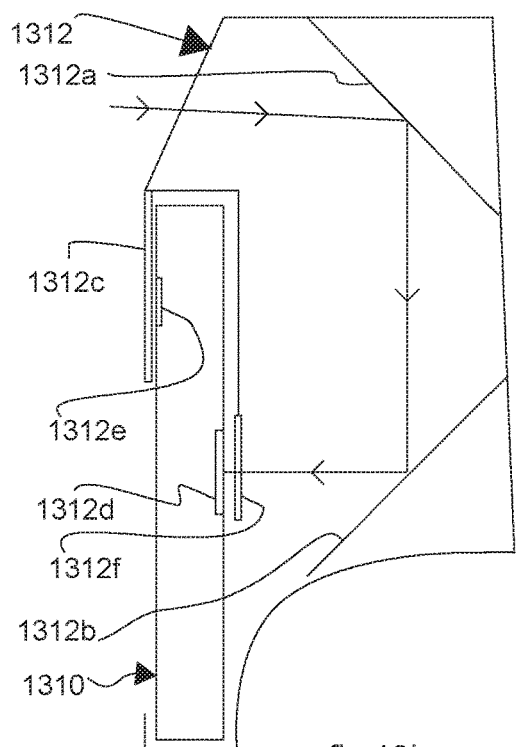

FIGS. 13a-d show details of an embodiment of mobile phone camera imaging arrangement with an adapter. FIG. 13a shows the placement of the phone (1310) on the dashpad (1311a), with a portion of it overhanging into the dashboard (1311b). The camera is aligned to the center of the steering wheel. The adapter (1312) has, built into it, two mirrors (1312a, 1312b) and two filters (1312c, 1312d). The two mirrors are used to direct light (that has been reflected from the eye) into the rear facing camera (1312e). Both the rear facing camera (13120 as well as the front facing (1312e) camera capture images. As with most mobile phone cameras, the front facing camera captures a larger area (but at a lower resolution) compared to the rear facing camera (which has a much higher resolution). The front facing camera is used as a coarse indicator of the eye position in the scene being captured, while the rear facing camera captures the finer details that are useful for eye movement event extraction. The rear facing camera can also be made capable of optical zoom (as opposed to software zoom) to get close-up images of the driver's eyes. These filters (1312c, 1312d) cutoff all wavelengths above and below the illuminator's narrowband wavelength. The illuminator can be external sources like IR sources, or patterns on the phone's display.

Figure 13E:
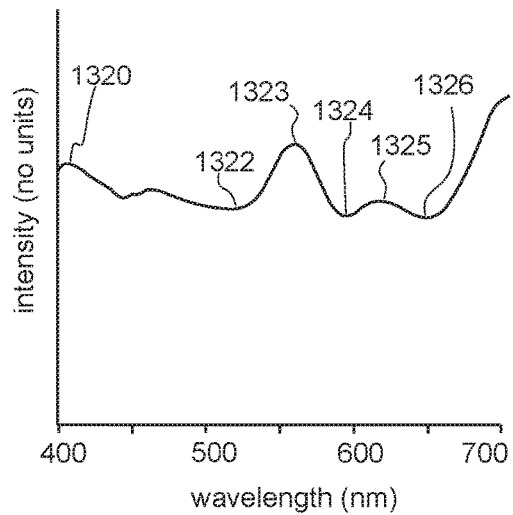
FIG. 13e shows an example ambient illumination spectrum inside a car.
Figure 13F:
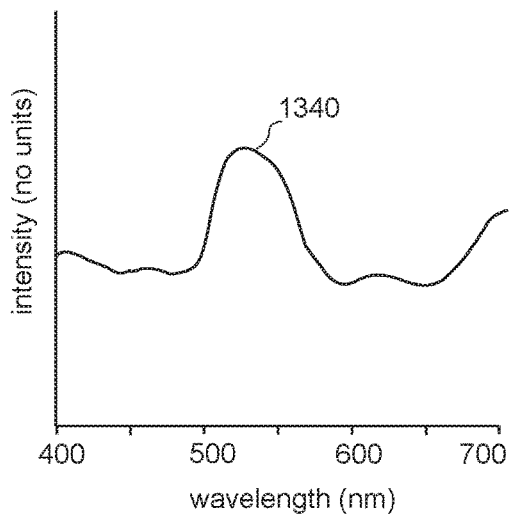
FIG. 13f shows ambient illumination spectrum inside the same car of FIG. 13e when driving through roads surrounded by greenery.

FIG. 13e shows an example of a typical ambient illumination spectrum inside a car with manufacturer tinted glass (only visible wavelengths shown). Clear peaks are marked 1320, 1323, 1325, and troughs marked 1322, 1324, 1326. FIG. 13f shows ambient illumination spectrum inside the same car of FIG. 13e when driving through roads surrounded by greenery. A peak associated with this greenery is indicated by 1340, which has a wide bandwidth of around 100 nm.

Figure 13G:
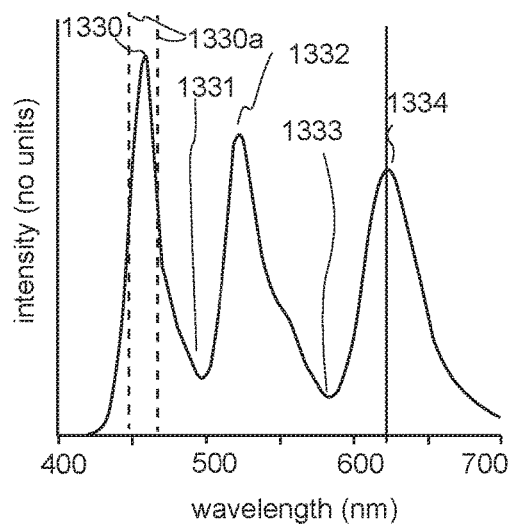
FIG. 13g shows an example smartphone with its full intensity wavelength spectrum.

FIG. 13g shows an example smartphone model with its full intensity wavelength spectrum. Its peaks occur at about 475 nm, 625 nm, 625 nm and are indicated by 1330, 1332, 1334, respectively, with corresponding full-width half maximum (FWHM) of 20 nm, 30 nm, and 50 nm, respectively. The FWHM for peak 1330 is indicated by two dotted vertical lines 1330a. In order to to maximize the use of these specific peaks, filters can be used in front of cameras in any convenient form, including clip-on, snug-fit. They can be for a single peak. If used for multiple peaks, two or more individual filters (that is, each on a separate glass substrate) can be used in sequence. If a single substrate with multiple coatings for each peak are required, dual-band or tri-band (corresponding to each peak) can be used to pass one or a combination of these peaks, and reject the other wavelengths. Alluxa, Inc. of Santa Rosa, Calif., makes a tri-bandpass filter for passing wavelengths in the 475 nm, 544 nm and 632 nm lines with FWHM of 27 nm, 15 nm and 64 nm, respectively. Alluxa also makes a tri-bandpass filter for passing wavelengths in the 438 nm, 513 nm, 572 nm lines with FWHM of 24 nm, 22 nm and 22 nm, respectively. These filters are typically >90% transmissive for the stated wavelengths. More such filters can be custom made and mass-fabricated for leading smartphone models since models differ in their peak wavelengths (and FWHM) of their color producing components. As can be seen from the comparison of FIG. 13e and FIG. 13g, ambient light has a flatter wavelength-intensity curve, while a smartphone screen has clear peaks and troughs. If the intensity of the ambient light is very high, it will be brighter than the phone's screen and overwhelm the camera's sensors, resulting in the inability to efficiently use the phone's screen as illumination patterns. In such cases, an option would be to use IR illuminators. However, this becomes less of an issue when the ambient light is subdued, and/or the vehicle has tinted glass.

In an alternative embodiment, the optical filters can be dispensed with, and a scheme for software implemented filtering as was described for FIGS. 12e can be used. The mirrors can be chosen to be fully reflective for all wavelengths, or in an alternate embodiment, selected for reflection only in the narrowband illumination wavelength. These filters can also be chosen to have coatings that are very transmissive in selected narrowband wavelengths, and highly reflective for all other wavelengths. Such an arrangement will help use multiple colors in the illumination patterns of the screen, and also allow switching of illumination wavelengths depending on ambient light as discussed earlier. In an embodiment, the video from the front facing camera is used to control a base. The base is attached to the car's dashpad via a stepper motor platform and a mount. The platform allows the base to rotate in precise steps. The base has the usual tip/tilt adjustment, and the phone is attached to the base. The front facing camera detects the rotational orientation of the driver's head. This information is used to control the stepper motor on the platform to rotate the platform (and therefore the phone) to rotate and follow the driver's head as when when he rotates his head.

FIGS. 14a-c show various arrangements of spectacle-like frame mounted eye and sound imaging systems. FIG. 14a shows a frame mounted eye movement imaging and ambient sound recording system adapted to be worn by the driver, with only a truncated head of driver shown in the figure. FIG. 14a1 shows the top view of FIG. 14a, while FIG. 14a2 shows the bottom view of the frame worn of FIG. 14a. The frame is symmetrical along its vertical axis, including components mounted on it, and therefore components on only one side of the frame are numbered. The frame (1401) has an inertial measurement unit (IMU) (1401a) with a clock. The IMU allows absolute position tracking of the head of the driver. On each side of the frame, there are: binaural recording device (1401b), two cameras (1401c, 1401d), and three IR illuminators (1401e, 1401f, 1401g). It should be noted that imaging of just one (for example, the dominant eye) can be carried out instead of binocular imaging in both head mounted as well as remotely mounted (dashpad) systems, although details like vergences that are related to binocular vision will be lost. Frame-mounted eye movement imaging systems, unlike dashpad mounted systems, are not aware of when the head is moving. IMUs help extract eye movement information if and when there is associated head movement, for example, in eye-in-head fixations. Both the eyes and head move when tacking objects at a high angle away from the steering wheel. In this disclosure, all reference to eye movement data assumes that head movement has been taken into consideration. It should be obvious that dashpad or other remotely mounted cameras (IR or visible wavelength) can be used to detect head movement instead of using IMUs.

FIG. 14b shows the front view of an embodiment of a frame mounted eye movement and ambient sound imaging system, while FIG. 14b1 shows the bottom view of this frame. The frame (1402) has symmetrical components, and an extra IMU (1402d) in the central portion. Only one side of the symmetrically placed components are identified in the figure. Prescription eyeglass (1402a) is clamped to the frame using a hard polymer clamp (1402b). The frame has another IMU (1402c) and a binaural recording device (1402e). In the space between the eyeglass and the eye, each side of the frame has two eye movement capturing cameras (1402f, 1402i), two IR illuminators (1402h, 1402g), a rear facing (road facing) camera (1402j) that captures images of the scene in front of the driver, and a autorefractor (1402k) that is used to record in near real-time where the eye is focused. The autorefractor faces the pupil and has its own IR source in-built, and projects a pattern on the eye. The cornea and the phakic lens of the eye together focus the pattern onto the fundus. The wavefront reflected from the fundus is sensed by a lenslet array in the autorefractor, and the wavefront is analyzed. The focal length of the eye's lens can then be deduced from this measurement since the cornea has a fixed focal length in an individual. This then gives the plane of focus of the eye. The line of sight (visual axis) of the eye can be derived from the eye position data extracted when recording eye movement data. Combining this line of sight with the focal length of the lens provides information on the point in 3-D space where the eye was fixated on. The road-facing camera on the frame captures video in real-time, and this can be combined with the eye fixation point to determine what object was being fixated on. In an embodiment, the driver wears a headband or frame that has tracker LEDs or geometrical features like patterns that help non-head-mounted imaging devices to track head positions so that imaging devices know the rough position of the head. If this known, the imaging device can pan to that position to better capture eye movements. The panning can be motorized and automated to track the feature on the headband.

FIG. 14c shows an embodiment of a frame mounted eye movement and ambient sound imaging system (upper figure), and the bottom view (lower figure) of this frame. Only one side of the symmetrically placed components are identified in the figure. Prescription eyeglass (1403a) are mounted on frame (1403) using a hard polymer clamp (1403b), the frame including IMUs (1403c, 1403d) and binaural recording device (1403e). In the space between these eyeglasses and the eyes, each side of the frame has two eye movement recording cameras (1403f, 1403g), two IR illuminators (1403h, 1403i), and an autorefractor (1403k) that is used to record in near real-time where the eye is focused. Outside this space (that is, outside the eyeglasses), rear facing/road facing cameras 1403j capture images of the scene in front of the driver. These road facing cameras are connected to the frame by a transparent hard polymer U-shaped member (14031) to the main frame, the U-shaped members going around the eye glasses. If prescription eyeglasses are not required, then the U-shaped member is not required, and instead, the road-facing camera can be attached directly to the frame, for example, just behind one of the eye-facing cameras. The autorefractors in this embodiment do not face the pupil, but instead face the eyeglasses. The eyeglasses have an IR reflective coating applied on their inner surface (the surface closer to the eyes). This coating type can be made almost 100% IR reflective (wavelength specific to the light source used by the autorefractor) at around 30-60 degree angle of incidence. In effect, the eyeglasses act as mirrors at this wavelength. In another embodiment, the autorefractor and the eye imaging cameras can share the same IR illumination source, with the sources having a pattern also suitable for the autorefractor. The autorefractor records in almost real-time the focal length of the eye's lens. As in the previous embodiment, this data can be combined with the eye fixation point to determine what object was being fixated on. In an embodiment, two autorefractors are used for each eye, the autorefractors for each eye spaced apart and placed along a line of canthal tilt of that eye. In another embodiment (not shown), the system of FIG. 14c can be used without the autorefractor.

Any of the previously discussed frame-mounted eye imaging systems can be used for any other purpose other than in a vehicle or during driving. These devices can be used whenever there is a need for eye movement tacking/imaging, or a need to determine the plane of focus and/or the visual axis (line of focus) of at least one eye, or a combination to provide the point of focus of at least one eye. When data relating both the left eye and the right eye are available, they can be combined to form stereoscopic data.

Any of the previously discussed frame-mounted eye and sound imaging systems can be used with a reduced or increased number of components. For example, the frame could have one or more eye-facing cameras for each eye, with one or more IR illuminators. If needed, the frame can be made for imaging only one eye (for example, the dominant eye), the other portion of the frame being empty. The binaural recorders can be dispensed with if not required, and the same with the road-facing cameras and/or IMU sensors. In any of the embodiments of the binaural sensors, any of the previously disclosed binaural sensors can be incorporated into any of the frames of 14a-14c as long as they are of a size that can be mounted on the frame without causing inconvenience to the driver. Furthermore, the binaural sensors can be incorporated to other parts of the car or driver, including the seat's headrest, roof-mounted, or on the driver's head.

Many of the previously discussed dashpad or frame/head mounted eye imaging system that also images the outside road might need to be adjusted so that the eyes as well as the outside road are imaged at the appropriate angles. Dashpad and head mounted monolithic devices like smartphones may not have the facility to separately adjust the tilt of the front facing and rear facing cameras. For example, tilting the phone when placed on the dashpad so that the camera is pointed towards the eyes will inherently cause the road facing camera to point downwards into the road, albeit to a small degree. When such minor vertical adjustments are required, optical flats or optical wedge blocks can be used, including Risley prism pairs. Such an adjustment solution for the horizontal axis might also be required if the device is placed away from the center-line (sagittal plane) of the driver. These optics can be made as clip on devices with minor adjustability, or incorporated into the adapter of FIG. 13b. If the two cameras (front and rear facing) are separate devices, as in the frames of FIG. 14b1 and FIG. 14c1, they can be made individually adjustable (mechanically) in the vertical and horizontal axes instead of using additional optics.

The devices mentioned in this disclosure, including the devices of FIGS. 7a-7d, 8a-8c, FIGS. 9a-9d, FIGS. 10a-10h, FIGS. 11a-11c, 12a-12f, 13a-13d, 14a-14c, as a whole system or as individual components, can be linked to processing units like laptops, tablets, computers, smartphones, notebooks or other devices, whether remote or local, using wi-fi, internet, intranets, bluetooth, USB connections, other cabled connections, 3G, 4G or 5G mobile connections, IR or any other convenient method. Information from these devices can be stored locally or remotely using these setups.

FIG. 15a shows 2.5 seconds of eye movement data of a driver captured when he drives a car. The non-autonomous car (car is not shown, only the scene in front of the car is shown) driven by a human driver has environmental sensors 2200 and human sensors 2250 as in FIG. 22. FIG. 15a shows just the first image of the video, but with 2.5 seconds (starting with time of the first image) worth of saccades and fixations overlaid on this image. Saccades are indicated by dotted lines (with arrows pointing the direction of the saccade), while fixations are indicated by circles. FIG. 15a has an example saccade (1510) and one fixation (1520) marked. The largest fixation circle is 600 ms, the smallest 200 ms. What is visible to one of the outside facing cameras is shown in the figure. As the driver is driving, the eye movement imaging system (dashpad mounted or head mounted or a combination) captures the eye movements of the driver. An image analysis system extracts data related to at least saccades and fixations, and optionally also data related to glissades, smooth pursuits, microsaccades, square wave jerks, drifts and tremors. FIG. 15b shows saccades and fixations isolated from FIG. 15a for clarity. Time and geolocation stamps are gathered along with outside video, driver's eye movement video, and LIDAR. It should be appreciated that not all data might be available at all times.

for example, during blinks, driving through tunnels, and poor weather conditions, but available data is recorded at all times. This data is saved in the vehicles on-board computer. Much higher computational efficiencies can be attained if foveated portions of an image are analyzed instead of the entire image. Also, foveated regions can be processed for color information, while the peripheral vision can be analyzed for moving objects, flashing objects, and sudden movements, lending itself to much faster, accurate and efficient computation.

Figure 22:
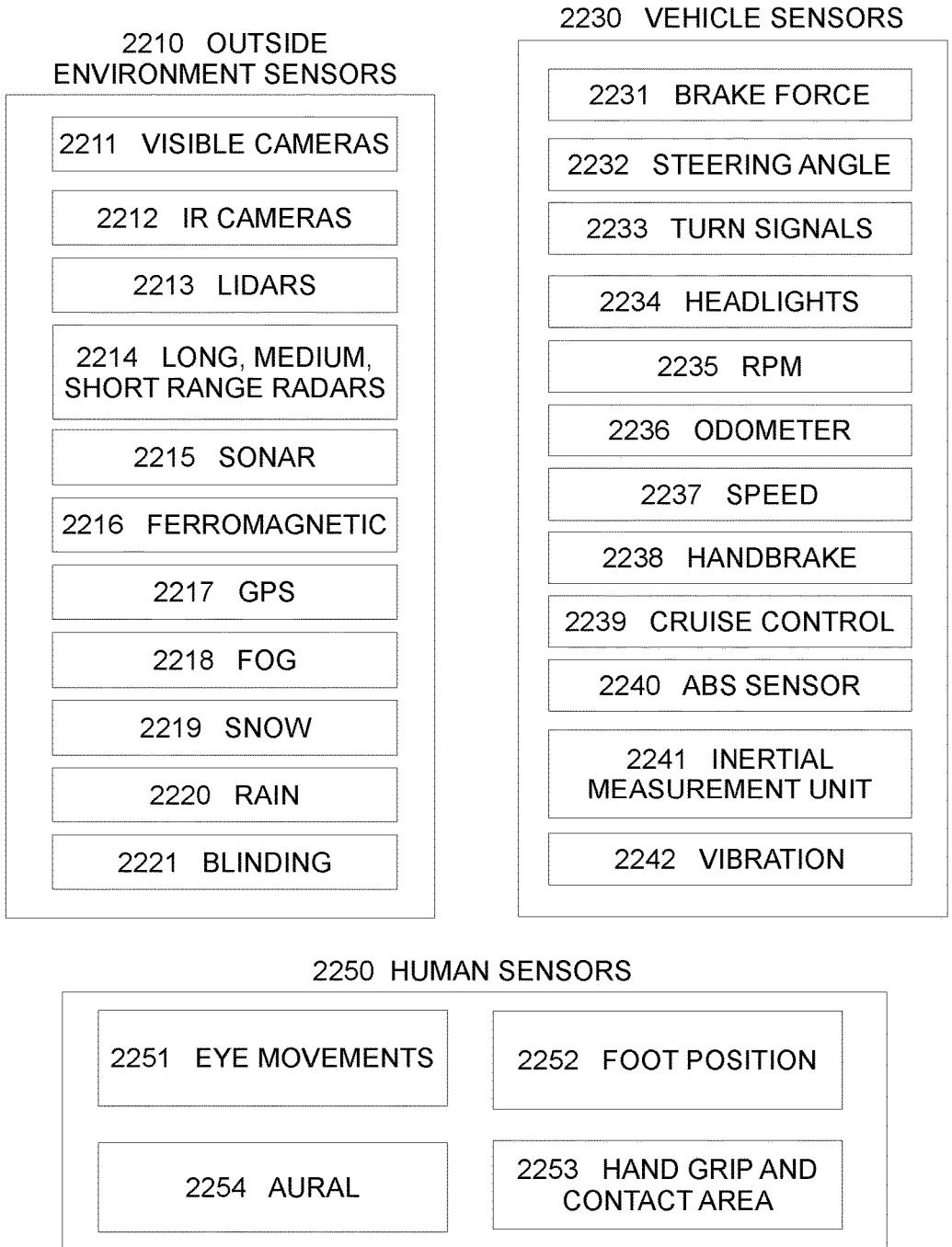
FIG. 22 shows different types of sensors used in a vehicle.

In the scenarios of FIGS. 16-20, time and geolocation stamps are gathered along with sensor data of FIG. 22 (environmental sensors 2200, human sensors 2250), including outside video, driver's head/dashpad mounted outside road facing camera video, driver's eye movement video, binaural audio, foot and hand sensor data, speedometer, RPM, wheel turning angle, weather (temperature, precipitation, visibility, humidify), LIDAR, radar, and ultrasound. Signatures are relative to each frame in a video, or a series of sequential frames of the video. The values of these events are recorded within each video frame (as metadata) or in a separate file (but with synchronized timestamps and/or geolocation data) as multi-dimensional arrays that include timestamps, geolocation (GPS/IMU), vehicle, outside environment and human sensor (shown in FIG. 22) data. It should be appreciated that not all sensor data may be available at all times. For example, when using a mobile phone to record sound and eye movement, binaural data will not be available, just a single microphone data. Or, the driver may be driving a vehicle that doesn't have all the sensor systems installed. Absence of some of these sensor system doesn't take away from the fact that event signatures can still be extracted—although with a loss of robustness and fidelity and possible increase in latencies.

Optionally, driver facing camera video can be discarded when called for. Instead, eye movement data can be appended to road facing video frames. It can also be saved as a separate file with appropriate time stamps and or geolocation.

In an embodiment, front facing (road facing) cameras are not used, or not turned on in smartphones. That is, video of the road ahead is not captured. Only the eye movement data/video, or this combined with foot and hand sensor data, is captured. This data can be mapped onto to a segment along with geolocation. A database of such information for each segment can be built. Although this arrangement cannot capture outside events, when used for a large population (sample size), it can provide useful data to identify possible outside events. The rationale is that events typically don't occur at the same geolocation all the time, and do not correspond to a map (that is, the associated map does not require the actions/responses of the driver). Repeated similar or identical combinations of at least one each of primary and secondary human sensors around the same geolocation could indicate a higher probability of an outside event occurring at such locations. This can be used to make improvements in AV software so that the software becomes more alert (and possibly slow down the vehicle and/or use different types of sensors) in these locations. An example is a short stretch of road where schoolchildren often cross the road (and not use designated pedestrian crossings that maybe at a far distance away as indicated on the associated map). When there is a mix of AVs and non-AVs on the road, the arrangement of this embodiment can be used for concurrent or near real-time training of AVs on the road if the vehicles are connected to a central server or are in communication with each other. This becomes important if a new outside event has suddenly become significant, for example: strikes/demonstrations, concerts, ball games occurring in the vicinity. If the outside (road facing) video is turned on, this concurrent training can be enhanced by transmitting video frames of the outside event and/or a signature extracted from the event, helping in concurrent cross-learning and cross-training between peers (vehicles are all AVs) and non-peers (a mix of non-AVs and AVs). This arrangement becomes more effective the more the number of human driven vehicles with human sensors traversing a particular segment/path. Expert drivers (discussed later) can be given higher weightage so that the event recognition is reliable and accurate, and peer/non-peer cross-learning/training becomes more reliable (less false positives, although there can be a slightly increased likelihood of false negatives due to habituation 2810*o*—discussed later) and occurs faster. Such an arrangement (with or without road facing cameras) can also be used to alert emergency/police personnel or maintenance/regulatory authorities during situation like: pothole in road, leaking water main by the roadside, spill/debris on road, accident on road, drunks leaving a bar etc.

FIG. 16 depicts a scenario of a human driver driving a car in a city road with several intersections and having light traffic. In this figure and its accompanying description, the car being driven by the driver is not shown, and all references to a driver relates to the driver of this car. However other cars (1601, 1602) on the road are shown. The figure shows roads, buildings, and other features from the perspective of the driver. The A-beams of the car are not shown in the figure, only the area within the windshield. The car has human, outside environment and vehicle sensors (as listed in FIG. 22).

An active ambulance is nearby, but not yet visible to the driver because it is hidden by a building (1603). The ambulance's sirens can be heard, but its flashing lights are not yet visible to the driver because buildings are blocking the view of the perpendicular roads ahead. Sounds, unlike light, are not completely blocked by buildings and trees. It appears to the driver that the ambulance is on one of the cross-roads since the road ahead and behind are clear.

Figure 26A:
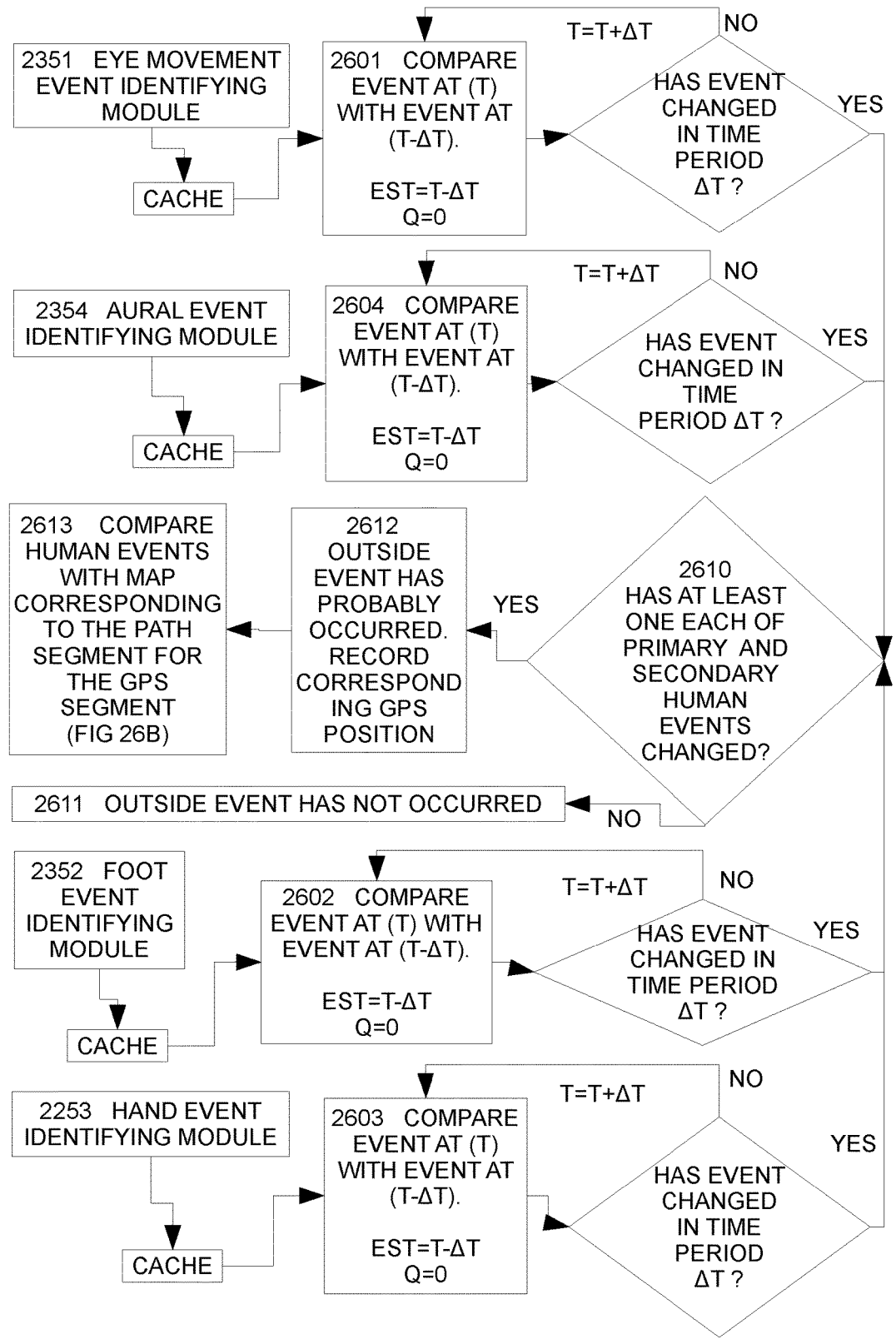
FIG. 26a shows a human event occurrence detection scheme.
Figure 26B:
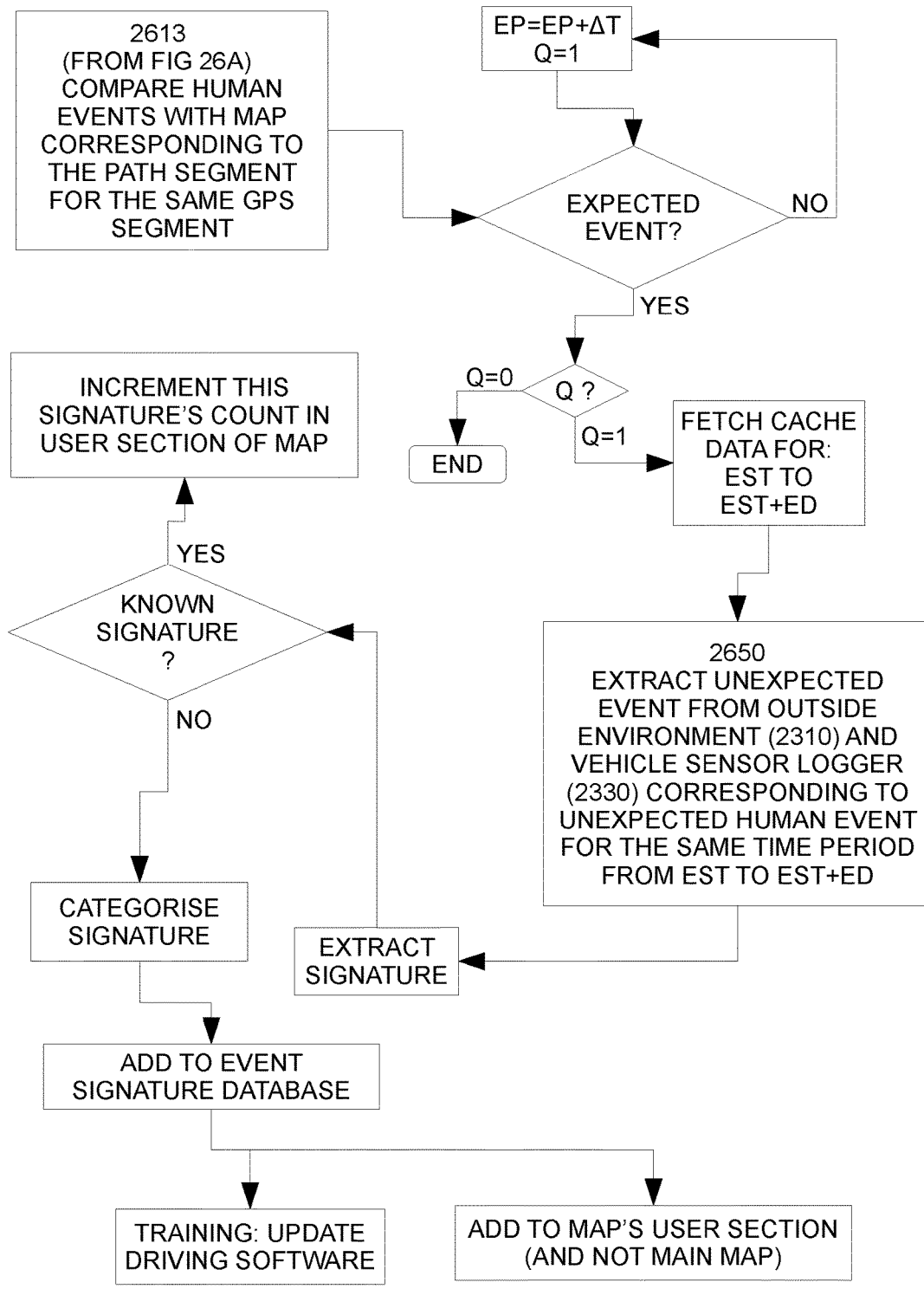
FIG. 26b shows an event extraction scheme.

When the ambulance's sirens become audible and discernible, the driver removes his foot off the accelerator and moves it over the brake pedal, while saccading to the rearview mirror, driver-side sideview mirror, and the left and right side in front to find out where the ambulance is. This saccading pattern is repeated until the driver is able to aurally establish the origin of the sound as coming from the front. After this, the driver's saccades are directed towards that region in the front. As soon as the reflections of flashing lights (1604) of the ambulance are seen by the driver (reflections bouncing from buildings, road and trees), the brake pedal is depressed slightly (inversely proportional to how far ahead the ambulance's lights are). The brake pedal is then continuously depressed to slow the vehicle to bring it to a rolling stop if and when the need arises. As soon as the ambulance exits the intersection (1605), the accelerator pedal is depressed to speed up the car if there are no other emergency vehicles following the ambulance. The binaural recording provides an extractable signature for the ambulance's siren. The human event occurrence detection scheme of FIG. 26*a* is used to detect that a human event has occurred in FIG. 16 since there is a foot release from the accelerator and movement over the brake pedal and also an associated aural event (ambulance siren) detected. Once a human event has been detected, the next step is to find the associated outside event that caused the human event to occur. The associated eye movement data is used to analyze the video images of the road ahead and behind (from road facing cameras) for detectable events. The image analysis is efficient because only the portions of the images where the eyes are saccading and fixating are analyzed. The initial faint lights of the ambulance are detected in the video images. Critical features include flashing lights and specific colors of the light. This forms the process of event signature extraction of FIG. 26b. Extracted components include aural (siren sound), video (flashing light), eye movement, and foot (slowing down of car). This is followed by the categorization, map update and training software update as shown in FIG. 26b. Several such instances under different conditions and from different drivers and geographical regions are similarly extracted and stored in the database. The "ambulance" event (in the form of a subroutine for emergency vehicle identification and reaction) can first be implemented in test vehicles. These test vehicles can be semi or fully autonomous. A variation of this scenario is when there is no light, just sound—which can be the case in crowded cities, for example. In such instances, only the binaural signal is captured. When using non-binaural recording (mobile phone with a single microphone, for example), directionality will be lost, but a sound signature can still be extracted, and combined with other human and vehicle (outside and inside) sensor data.

Signatures from multiple instances of such ambulance appearances from different subject drivers can be used to form an averaged scenario signature (including sound and light signatures) and AV response to an approaching ambulance. These instances can be from a group of drivers in a region having similar flashing light schemes and sounds for ambulances, and also similar traffic rules regarding ambulances. Although one instance can be used for training, for improved accuracy, several such events from several different paths driven by several different drivers can be acquired and used to train AVs. This specific subroutine is then fine-tuned by software self-learning (artificial intelligence) or by a (human) programmer or a combination. After several cycles of fine-tuning and testing, the subroutine can be implemented in non-trial AVs. Without this updated software, the AV would have continued without reducing speed significantly—until an ambulance actually appeared.

FIG. 17 shows a scenario in which a small child is ambling towards the edge of the road of the same lane (LHT). A human driver is driving a car (RHD) at around 36 km/hour speed on this narrow undivided road with buildings on either side. The driver sees the child (1701) 100 meters ahead emerging from behind a pillar (1702) without an accompanying adult being visible. The edge of the pillar is 2 meters from the edge of the road. In reality, an adult is holding the hand of the child, but is behind the pillar and therefore hidden from the driver's view. The driver's eyes saccade to the child and form an ROI around the child (ROI-child), which includes checking for adults minding the child, and tracking the child moving closer to the road, interspersed with saccades to the road ahead. The driver has now become alert, and increased hand grip and contact area on the steering wheel. The foot goes off the accelerator and over the brake pedal. With the eyes unable to find an accompanying adult, and the child being about 70 meters ahead, brakes are applied to lower the speed from the initial 36 km/hour to 18 km/hour in a span of 2 seconds. As the eyes saccade to and fro between the ROI-child (which is now about 60 meters ahead of the driver) and the road ahead, the child inches closer to the road. The driver is still unable to spot an adult. The car is slowed from 18 km/hour to 10 km/hour in 4 seconds. The child is now 1.5 meters from the edge of the road, and the car is about 50 meters from the child. The brake pedal is kept depressed in preparation for a complete stop to take place about 10 meters from the child. However, 30 meters from the child, the driver is able to see the adult holding the child's hand. The driver's eyes saccade to the adult, fixate, and then establish an ROI around the adult cum child. The adult (who has apparently seen the approaching car) restrains the child from moving forward. The foot goes off the brake now. The driver then presses on the accelerator pedal to quickly bring back the speed to 36 km/hour. This signature is captured and processed, and then filed in an "unaccompanied child approaching road" subcategory under main category "Child" (2502 as listed in FIG. 25). From the foregoing, it can be seen that the driver was being over-cautious. He reduced the speed to 5 km/hr at 50 meters from the child, even though the child was 1.5 meters from the road. However, when data is gathered from a large population of drivers, the average speed at 50 meters from the child would be 20 km/hr, which can be used by an actual AV.

The human event occurrence detection scheme of FIG. 26a is used to detect that a human event has occurred in FIG. 17 since there is a sudden foot release from the accelerator and movement over the brake pedal and increase in hand grip and contact area on the steering, both with associated eye-movement to the side of the road and formation of ROIs and saccades/fixations around the child. Once a human event has been detected, the next step is to find the associated outside event that caused the human event to occur. Video images from cameras facing the road are analyzed using image processing, and the child is identified as corresponding to the eye movement data, as also the edge of the road. This video clip, along with critical features like lack of adult accompanying the child, and the spacing between the child and the road are stored as part of the signature. This forms the process of event signature extraction of FIG. 26b. This is followed by the categorization, map update and training software update as shown in FIG. 26b. Several such instances under different conditions and from different drivers and geographical regions are similarly extracted and stored in the database. When AVs (semi or full) are operating on roads, they continuously monitor road-facing video. The video is examined and features extracted in real-time, the extracted features including nomenclature and categorization information. Extracted features are compared immediately to features in the AV's database. It is to be noted that the comparison is not video to video (or video-frame to video-frame) comparison of the current scenario to the database, but rather extracted features in the scenario to the extracted features in the database. As to what features in the video clip require extraction since there are dozens of features in each frame, the features that were saccaded to, or fixated at, or slow tracked, or an ROI formed, are extracted (along with the road and its outline when necessary). When the updated training software is used by an AV, and the AV encounters a similar "unaccompanied child approaching road" scenario (that is, the features extracted from the video include a child without an accompanying adult, and at the edge of the road), it reduces speed and analyzes the ROI around the child at a higher priority, while reducing speed to about 20 km/hour by the time it gets to 50 meters of the child. Once the adult is detected, the speed is resumed to 36 km/hour. Without this updated averaged software, the AV would have continued without reducing speed, and an accident could have probably occurred if the child was actually unaccompanied and entered the road. The additional benefit of using the updated software is that higher speeds can be maintained without being overly cautious, and rational speed decisions can be made depending on how the situation evolves.

In the above discussion, only road facing video was discussed as being relevant or as being analyzed. Although LIDAR data can also be used for this purpose, either by itself (if possible) or in conjunction with video data, for the sake of simplicity, only video data is discussed. In this disclosure, when the discussion and examples (and also the figures) do not include LIDAR data but only video data, it should be understood that this is done for simplicity in explanation and illustration, and is not be construed as excluding the possibility of using LIDAR data. Vision is one of the key sensors for humans. To perform more human-like tasks, vision will become the primary differentiator compared to vehicles using LIDAR. While this transition is occurring, LIDAR can be used by itself or along with visible wavelength video. However, in the long run, LIDAR will eventually be mostly replaced with visible wavelength video. LIDAR can not resolve features like video can do. For example, analysis of a child to determine age (using body and facial features) can be done by video but not LIDAR. Other drawbacks of LIDAR include: low resolution, monochrome, low operating ranges, low scan rates, can only detect physical objects and their outlines, but not signage, emitted/reflected light (like road signage, brake lights). Therefore, in this disclosure, LIDAR use can not be substituted for video unless LIDARs are capable of performing the function being discussed (including seeing through bad weather, poor lighting conditions).

Figure 18A:
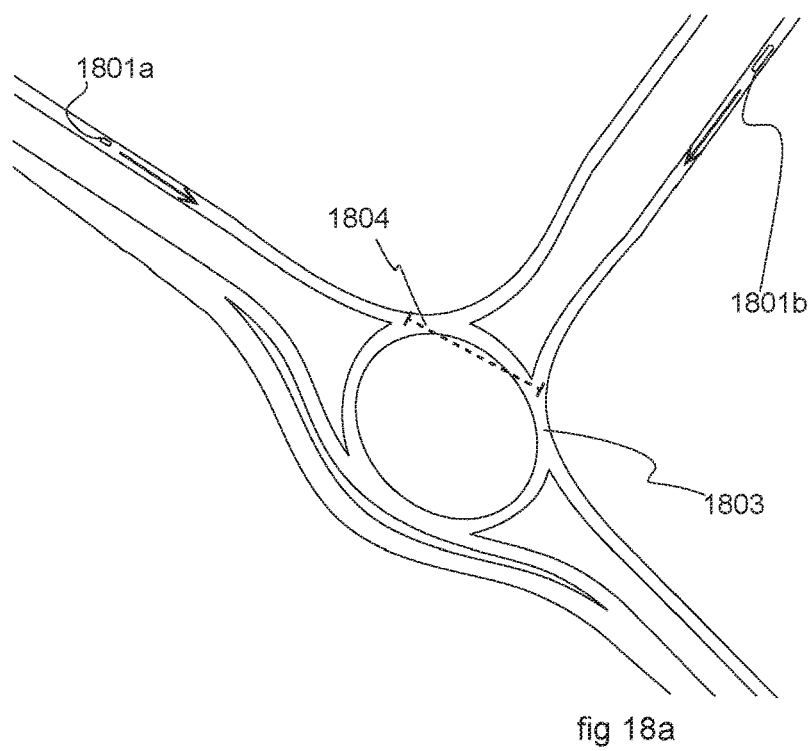
FIGS. 18a-18b show a scenario on a road with a long truck that is not slowing down.
Figure 18B:
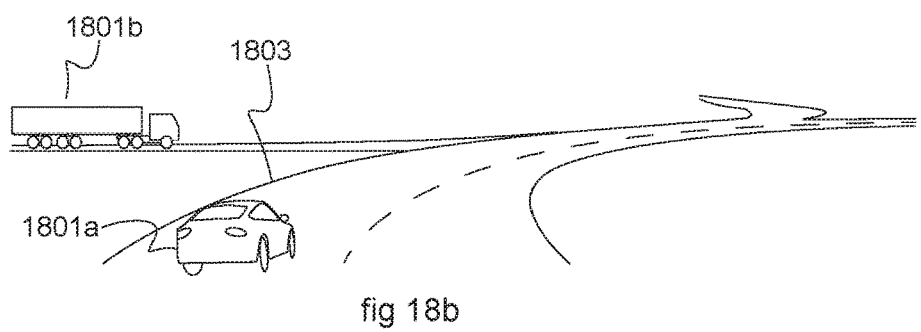

FIG. 18a shows an aerial view of a scenario in which a human driver is driving a car (1801a) that is approaching a roundabout having three roads entering it. All references to a driver in this scenario relate to the driver of the car. A heavy truck (1801b) is also approaching the roundabout (1803). Both the car and the truck are traveling in the directions shown, and are 200 meters from the roundabout. The car is traveling at 80 km/hour and the truck slightly slower at 75 km/hour. The distance (1804) between the car's entry point into the roundabout and the truck's entry point is about 75 meters. While FIG. 18a shows this starting scenario. The truck is not slowing down as it is getting closer to the roundabout. The car has the right of way, but the driver is not sure if the truck will eventually stop. The truck appears in the driver's peripheral vision, and the driver makes a saccade towards the truck, and then slow tracks it (for about 3 seconds) as it approaches the roundabout. During this period, the driver's grip on the steering wheel and the contact area increase slightly. The foot goes off the accelerator, but does not move over the brake pedal. The driver then makes a saccade towards the roundabout to check if there are other vehicles in or about to enter the roundabout (vehicles inside the roundabout have the right-of-way), and observes that the roundabout is clear. The driver's eyes then quickly saccades to the truck and then slow-tracks it for another 3 seconds. Since the truck is not slowing down, but continuing towards the roundabout, the driver's foot goes over the brake pedal and depresses it to halve the speed from 80 km/hour to 40 km/hour in 4 seconds. FIG. 18b shows the perspective view of the scenario at this time, wherein the truck is about 40 meters from the roundabout and starts slowing down rapidly and the car has already entered the roundabout. The car driver has been slow tracking the truck, and notices it is slowing down. The driver's foot goes off the brakes for 1.5 seconds, while the eyes saccades to the roundabout to check for entering traffic, and saccades back to the truck (which has almost come to a complete stop) and goes over the accelerator pedal and depresses to rapidly speed up to 60 km/hour and enter the roundabout. The scenario beginning at FIG. 18a, proceeding through 18b, and ending after the car has exited the roundabout, is captured and a signature extracted and categorized under "Danger" (see signature categorization in FIG. 25 and related text).

Figure 19A:
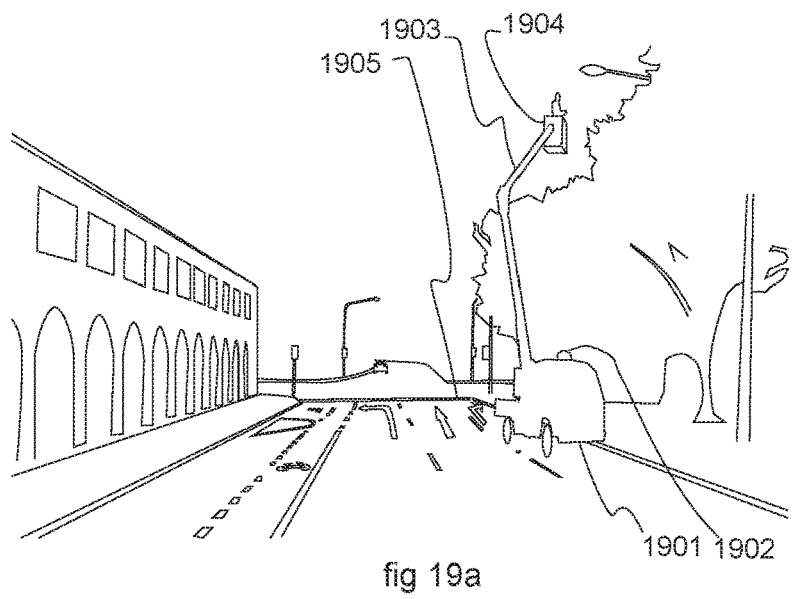
FIG. 19a shows a scenario on a road with a maintenance vehicle on the road.

FIG. 19a shows a scenario where a driver driving a car (in a LHT road) encounters a maintenance truck on the same (right-most) lane replacing street lights. In FIG. 19a, the car is not shown, only the maintenance truck (1901) is shown. The truck has a flashing yellow light (1902), and an extended boom (1903) with a platform (1904) having a person on it. The car is 60 meters from the truck and traveling at 40 km/hour, and the truck is 40 meters from the intersection (1905). The car is on a 'right turn only' lane, and intends to turn right at the intersection. The driver sees the truck on the lane. The driver's eyes saccade to the truck body, then to the boom and the platform above, and then to the person on the platform. The eyes establish an ROI around the truck, boom and person, saccading around it, while the hand grip and contact surface area on the steering wheel increases. The foot simultaneously goes off the accelerator and on to the brake pedal, slightly depressing it. The eyes then saccade to the rearview mirror and sideview mirror, the end of the road (which the driver notices is about 40 meters from the intersection), and then back to the truck. The car is slowed down to 15 km/hour over 3 seconds. The car is now 30 meters from the truck. The driver instinctively decides to drive around the truck by switching to the other lane on the same side without expecting the truck to start driving away. After this, the driver switches back into the original lane. If the truck were parked at the intersection, then the human driver would have switched lanes and taken an alternate route, for example, going straight through the intersection. The decision to switch lanes to get around the truck involved the eyes establishing an ROI around the truck-boom-platform, and saccading and fixating within this region, and also to the rear/sideview mirrors and the intersection, deciding it is safe to switch to another lane and back again (while mentally noting that there is no traffic in rear/side view mirrors, and there is enough distance between truck and intersection). The signature of this event is captured (as described in the previous scenarios), and categorized under "Unexpected Objects" (see signature categorization in FIG. 25 and related text), under a sub-category of "Maintenance vehicle, stationary". The signature includes the video clip of the relevant time segment, relevant features that were extracted from this segment, including: maintenance truck with flashing yellow lights, extended boom with platform. The video clip is saved for archival and for later analysis whenever needed. If there is a need to save storage space, the signature can either be stored without this video clip, or with only a reference to the video clip (for example, a video clip serial number by itself or including date, time, geolocation, vehicle and environmental sensor data like speed and heading, weather, road lighting-level information etc). The signature will have data relating to the type of event (maintenance vehicle, stationary, unexpected object) as discussed earlier.

FIG. 19b shows a scenario of a child on a bicycle on the pavement on the same side of the lane (on a LHT road) that a human driver is driving a car. FIG. 19b1 shows eye movement data for the first 4 seconds of this scenario superimposed on a still image. FIG. 19b2 shows just the eye movement data, while 19b3 shows an enlarged version of FIG. 19b2. The circles represent fixation points and time, the largest circle corresponding to a fixation time of about 500 ms, while a majority of them are 150 ms. The straight lines represent saccades, with directions indicated by arrows. Over the course of this scenario, there is no other distraction in the foveal or peripheral vision, including no traffic lights or other traffic. The car is on the rightmost lane and 100 meters away from the child (1910), driving at 50 km/hour. There is no traffic on the road. The driver's eyes saccades to the child and the bike (1911), forming an ROI around it. The eye-brain combination conclude that the bicycle is stationary, with both feet of the child on the ground, and the front wheel is close to the edge of the road. There are no adults accompanying the child (and therefore the child's actions can be more unpredictable and risky). The child appears very young, perhaps 4-8 years old, and therefore can perform unexpected moves, including riding the bike into the road without waiting for the car to pass, or stumbling and falling onto the road. Expecting this, the driver's grip and contact area on the steering wheel increases slightly, while the foot goes off the accelerator and goes over the brake pedal and depresses it to bring the speed down to 25 km/hour over 4 seconds, all the while saccading within the same ROI to detect unexpected actions of the child, except for one saccade to the end of the road and one slightly to the right of this point. The car is now 60 meters from the child. The child is closer, and the driver is able to confirm that the child is indeed very young, probably 4-6 years old. With no change in the child's pose (i.e. the child is well-balanced and stable, and not rocking the bicycle back and forth), the driver's apprehension level drops, but is still very cautious because of the age of the child, and reduces the speed to 15 km/hour in 4 seconds. The car is now 35 meters from the child. The driver halves the speed, down to about 8 km/hour over 4 seconds, and is about 20 meters from the child. The car proceeds at this very low speed until it is 5 meters from the child. The driver then removes the foot from the brake and depresses the accelerator pedal to bring the speed to 40 km/hour in 3 seconds. The signature of this event is extracted and categorized under "Child" (see signature categorization in FIG. 25 and related text), under sub-category: "Child on bicycle", sub-sub-category "unaccompanied child on bicycle" and a further sub-category: "unaccompanied child on bicycle at edge of the road".

The learning here is that the driver's reaction is proportionally related to the child's age, distance from the edge of the road (inverse relationship), absence of accompanying adults, and present speed of travel. These reactions include saccades around the ROI, grip and contact area on the steering wheel, reduction in speed (including the quantum of reduction, latency to starting the reduction process, distance from the child before the reduction is applied). If this were an AV software, the image processing system would process these factors to form a response, including speed reduction. Without training, a traditional AV software will not prepare for evasive actions or reduce speed to account for the unexpected. Being over-cautious all the time, the overall speeds of AVs are lower than humans. Training AVs can make them faster, while helping incorporate more logic and rationale. If a very small child on a small bicycle is being closely accompanied by an adult, then the image processing will identify the adult following the child's bike and become less cautionary. There are variations in such a scenario: for example, there is an adult, but the adult is 5 meters away from the child. Caution and speed reduction will become greater now. Automatic identification of such an "unaccompanied child on bicycle at edge of the road" scenario will become easier, efficient, and more comprehensive when data from a swarm of drivers is used. The collection of such scenarios will grow with time, and become well-defined algorithms in the training software. Over time, variations of "kid on a bike" (like "kid on skateboard") can be added to the set of algorithms, particularly as the test-base grows. New, but unidentifiable, variants can be manually processed for scenario detection and response.

FIG. 19c shows a scenario where a soccer ball rolls into a suburban road on which a human driver is driving a car. The car is traveling at 50 km/hour. The driver notices the ball (1921) entering the road 50 meters ahead from a point (1920a) behind a tree. The driver's eyes saccade to the ball and slow tracks it for about a second. The direction of the ball is indicated by arrows on the broken line (1920b). After confirming that it is a ball rolling into the road, and anticipating the possibility of a child following the ball into the road without watching out for traffic, the driver's grip and contact area on the steering wheel increases slightly. The foot goes off from the accelerator pedal and onto the brake pedal without depressing it. The eyes stop tracking the ball, but instead saccade to the point from where the ball came from, and establishes a ROI around that area. After the car gets to 20 meters of point 1920a, the area around it becomes clearer (not hidden by trees or shrubs). The eyes saccade to a point that is a backward extension of line 1920b and which is 5 meters from the road. The car has meanwhile slowed to 45 km/hour (because the accelerator pedal was not depressed). Seeing no person present there, the driver assumes that no one is following the ball, and returns the foot to the accelerator pedal 5 meters from point 1920a to return to a speed of 50 km/hour. The signature of this event is then extracted and categorized under "Child" (see signature categorization in FIG. 25 and related text) rather than "Unexpected Objects". A non-human navigating a vehicle will notice the ball rolling across the road, but will continue if the ball has exited the lane. A human would expect a child to appear unexpectedly following the ball. The eye movement pattern will be saccading to the ball, smooth pursuit for a short time and saccading to the region from where the ball might have originated. Depending on the vehicle speed and distance to the ball, the foot might move away from the accelerator pedal and move over to the brake pedal at different speeds, and might depress it very little (or not at all) or a lot. However, the basic signature underlying such variations will have a similar pattern.

FIG. 19d1-19d3 show the scenario of a kangaroo entering a single-lane LHT rural highway on which a human driver is driving a car at 100 km/hour. The sun has already set, and it is dusk now. The car has its high-beam lights on. The driver has been driving in a relaxed manner, with just two fingers and a thumb lightly touching (and not pressing down hard) the steering wheel. One hundred and fifty meters ahead, the driver sees an object moving in his peripheral vision. His eyes saccade to the object, and notices it is a 1.5 meter tall kangaroo (1931). Both of the driver's hands grab the steering wheel, gripping it (medium force) with all fingers. The foot simultaneously releases the accelerator pedal and moves over the brake pedal, depressing it with medium firmness. The car is now 100 meters from the kangaroo and moving at 70 km/hour. The driver's eyes are slow tracking the kangaroo as it hops into the driver's lane. An experienced driver, he knows that kangaroos move in mobs, and there might be more of them following the one that just got on the road. He also knows that kangaroos often stop and stare at a car's blinding lights, sometimes even turning around from the middle of the road or right after just crossing it. He continues pressing down on the brake pedal to slow the car down to 50 km/hour, while forming an ROI around the kangaroo (but fixated on its glowing eyes whenever it looks at the car), slow tracking it whenever it hops. The kangaroo hops away into the far side of the road just as the car passes it. The signature of this event is extracted and categorized under "Danger" (see signature categorization in FIG. 25 and related text), under sub-category: "Animals", sub-sub-category "Kangaroo". Incidents of kangaroos on (or by the side of) the road are recorded and signatures extracted. There will be numerous variations of this signature. For example, the kangaroo stopped in the middle of the road and would not budge, or it turned around and hopped back into the car's lane after reaching the divider line, or there were more kangaroos following the original one. However, common aspects will include slow-tracking of hopping, or fixation on the kangaroo, all of which can be extracted from eye movement video, road facing camera video (IR and/or ambient light), and long range radar and LIDAR (if used) is used, and combined with hand and foot sensor data. Pattern analysis can be used to identify both the kangaroo as well as bright spots (eyes) on the roads and shoulders in the night in rural or kangaroo-prone roads. Smooth pursuit when looking far away from the side of the road indicates the kangaroos are not close to the road, and therefore there is no danger. The gait of kangaroos varies with their speed. When they are ambling or feeding, they use all their limbs. While running at low speeds, they are on their hind limbs, but not hopping very high. When running fast, they are on their hind limbs and hopping much higher. The gait of kangaroos is also distinguishable from other animals like cows because the preference of kangaroos to use hind limbs. This aspect of kangaroos preferring hind legs for locomotion can be exploited by the outside facing video image analysis to distinguish kangaroos from other animals. With numerous such events being captured under different conditions, a robust automated kangaroo detector and countermeasure subroutine can be formed. Capturing the appearance (size, shape, color) and gait of different animals under different conditions allows the extraction of signatures unique to each animal, and categorization under appropriate animal sub-categories. It will be appreciated that the signature extraction schemes in the various scenarios in this disclosure not only capture human actions and reactions to specific events, but they also indirectly capture the memories and experience of the human drivers, along with human logic, deduction, rationality and risk-mitigation strategies since these are the factors that cause drivers to act and react a certain way. For example, the driver just discussed knows from experience and memory that kangaroos move in mobs, and that there might be many more crossing the road, and that kangaroos have a tendency to linger on the road or hop back into the road after seeming to try to cross it. Using such signatures will reduce or negate the need for these actions and reactions of the driver to be manually programmed into AV software by a human programmer. Such signatures carry a wealth of human knowledge, experience and logic accumulated over years and spread among a wide variety of geographies and populations, and their trade-offs with rationalization and risk management, allowing safe, fast, efficient and pleasant transportation. As societies transition towards non-human vehicle operators, all this is saved as signatures for use by AVs without being lost to time.

Figure 20A:
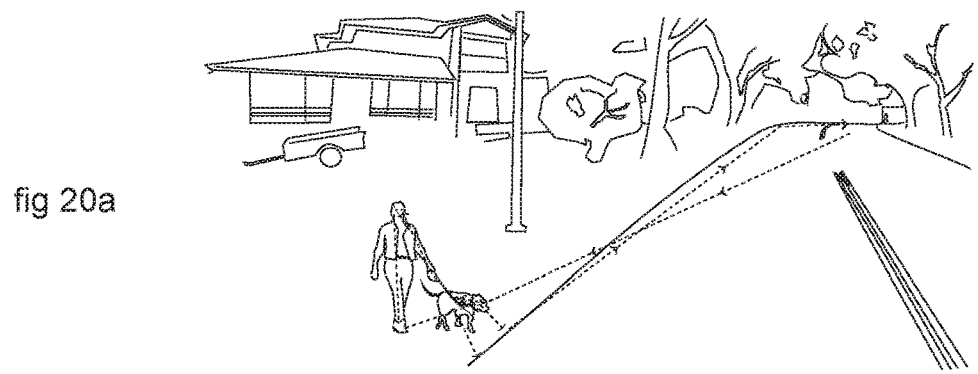
FIGS. 20-20b show a scenario on a road with a dog on a leash by the edge of the road, and the saccades/fixations of the associated ROI.
Figure 20B:
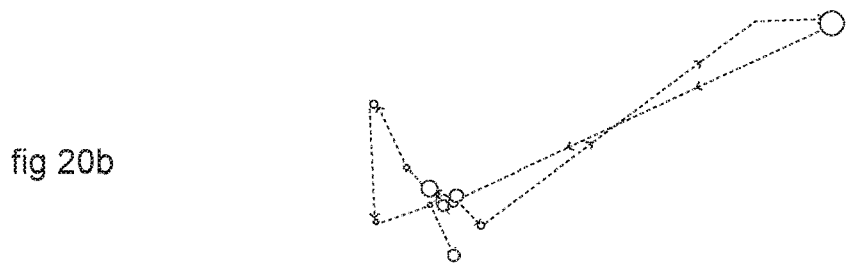
Figure 21:
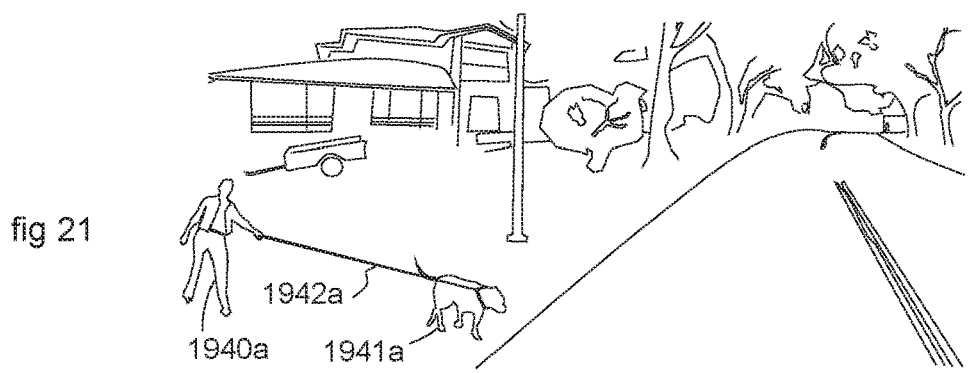
FIG. 21-FIG. 21b show a scenario on a road with a dog on a stretched leash by the edge of the road, and the saccades/fixations of the associated ROI.

FIG. 20 and FIG. 21 show two scenarios of a dog on a leash by the side of the LHT road and walking towards the road on which a human driver is driving a car. In the first instance (FIG. 20), the dog (1941) is close to its human (1940), and the leash (1942) is sagging. In the other case (FIG. 21), the dog (1941a) and its human (1940a) are further apart, with the leash (1942a) taut and the dog appearing to be tugging on the leash. In the first instance, the driver will not observe a possible danger, and will continue driving normally. In the second case, the driver will slow down, expecting the possibility that the leash would give way or pull the human along as the dog runs into the road. The driver's eyes will saccade to the dog, form an ROI around it (and notice its body to check its body size and whether its body pose indicates tugging), then trace the leash and form a simple ROI around the human (and check if it is an adult, and body pose to see how much control the human has). Depending on the outcome, the driver slows down or continues at the same speed, with corresponding hand grip/contact area, foot positions.

Figure 21A:
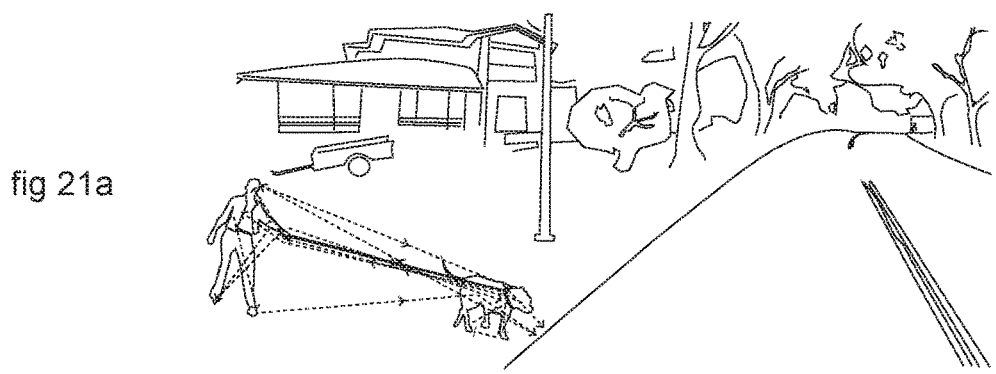
Figure 21B:
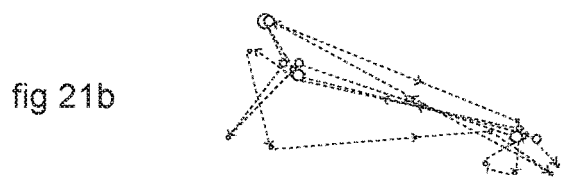

FIG. 20a and FIG. 21a show corresponding eye movements for FIG. 20 and FIG. 21. The eye movement overlay is shown separately (for the sake of clarity) in FIG. 20b and FIG. 21b, and also show added fixation details. The eye movement overlays in FIG. 20a and FIG. 20b starts from when the driver notices the dog in his peripheral vision and saccades to it, and ends 2 seconds after this. It should be appreciated that most eye movements are not conscious. Saccade directions are indicated by arrows, fixations are indicated by circles, with the smallest circle being about 100 ms, and the largest one 350 ms. The eye movement overlay in FIGS. 21a, 21b starts from when the driver notices the dog in his peripheral vision and saccades to it, and ends 3 seconds after this. The dog and the human have separate ROIs in FIG. 21a, but are a single ROI in FIG. 20a. Signatures are extracted and categorized under "Danger", sub-category "Animal", sub-sub category "Dog", which can have sub-sub-sub categories "large dog", "small dog", "seeing dog" etc. The appearance of the dogs by the side of the road caused the driver's eyes to saccade and form ROIs around the dog/human features. Although there is a continuously changing scenery as the vehicle traverses the path, not all features on or by the side of the road are of interest or concern to the driver. The driver's eyes may saccade and form an ROI around a house painted in bright pink, but this is not a cause for concern to the driver. Therefore, the driver will not slow down the car or grip the steering wheel harder. That is, the pink house is not an event outside of the car to be of concern to the driver. However, a dog tugging on its leash is an outside event that is a cause for concern to the driver. The driver will then perform the human events of saccading and forming an ROI around the dog/human, slowing down the car (by releasing his foot off the accelerator pedal and depressing the brake pedal) and grip the steering wheel harder to steer away from the dog. For automatically detecting if an outside event has occurred, the outside event occurrence detection scheme of FIG. 26a can be used. Video images from cameras facing the road are analyzed using image processing, and the dog-human pair are identified as corresponding to the eye movement data, as also the edge of the road. Critical features like the spacing between the dog and human, size of the dog, leash curvature (lack of), human pose, and distance to edge of road are stored as part of the signature. This forms the process of outside event signature extraction of FIG. 26b. This is followed by the categorization, map update and training software update as shown in FIG. 26b. Several such instances under different conditions and from different drivers and geographical regions are similarly extracted and stored in a database, and made available to AV software for training to recognize such outside events. When the updated/trained software is used by an AV that encounters a similar "big dog at edge of road tugging on leash held by human" scenario, it reduces speed and becomes cautious (analyzes the ROIs at a higher priority). Without this updated software, the AV would have continued without reducing speed significantly, and an accident could have probably occurred if the leash were to break or slipped out of the human's hand, or the dog, dragging its human, had entered the road. Features extracted from the scenario and stored into the signature include big dog, leash, accompanying human, edge of road. The storage is not as a video segment or still-image frame(s), but as feature nomenclature, properties, classification/categorization, geolocation, time/date. However, the video clip can be stored for other purposes like later analysis and additional feature extraction, manual comparison at a later time, quality control, software capabilities development and enhancement, further training, archival or legal reasons. The signature will also have data related to vehicle inside and outside sensors, and human sensors as discussed in FIG. 22 and FIG. 24 and corresponding text.

The scenarios discussed include numerous types of eye movements. However, it should be noted that not all these types of eye movements will necessarily occur for every scenario. For example, when driving on a road, a van is trying to enter the road from a side-road. The eyes will saccade to the van. Detection of this saccade can be used as an indication of the beginning of the scenario of a van entering from a side-road. Not all eye movements need to be captured by the imaging system. However, this causes a reduction in eye movement data captured, and therefore leads to lowered quality, fidelity, robustness and reliability. For example, the system can be made to capture just saccades, or just saccades and fixations, or just glissades and fixations, and so on. Saccades (or its related eye movements: glissades and square wave jerks) and slow-tracking are two types of eye movements between fixations. While driving, slow tracking occurs much less frequently than saccades. Therefore, the eye movement imaging and analysis systems in this disclosure must, at a minimum, be able to capture, process and extract saccades (or at least one of glissades or square wave jerks as an indication that a saccade has occurred). In addition, the ability to capture, process and extract fixations can be added to improve the quality, fidelity, robustness and reliability of eye movement data.

In order to observe and record human events, human sensors are deployed inside vehicles. These sensors compliment sensors already present in vehicles, which are collectively termed environmental sensors.

FIG. 22 shows details of an enhanced set of environmental sensors that include human sensors. Environmental sensors (2200) include sensors to sense the environment outside the vehicle (2210), sensors to sense vehicle functioning (2230), and human sensors (2250). Outside environment sensors (2210) include: visible cameras (2211) to capture visible wavelength images outside the vehicle, including front, rear and side facing cameras, infrared cameras (2212) to capture images in the infrared wavelength. Lidars (2213) are time-of-flight distance measurement (and also intensity) sensors using pulsed lasers in the 0.8-2 micron (infrared) wavelength range. Lidars provide a 3D map of the world around the vehicle, including distances to objects. Radars (2214) map the position of close-by objects, while sonar (ultrasonic) sensors (2215) detect nearby objects. Ferromagnetic sensors (2216) detect ferromagnetic objects, particularly those on the road, including buried strips. GPS (2217) use global positioning satellites to determine the vehicles position. Other environment sensors include fog (2218), snow (2219) and rain (2220) sensors. Blinding (2221) sensors detect light that is blinding the driver, including sun low on the horizon, and high-beam headlights from vehicles coming from the opposite direction. Vehicle sensors (2230) sense the vehicle's actions, performance and instantaneous position. It includes sensors for measuring current brake force (2231) and steering angle (2232), detection of turn signals (2233), status of light (whether headlights are turned on/off, and high beam) (2234), RPM (2235), odometer (2236), speed (2237), handbrake position (2238), cruise control settings (2239), ABS activation (2240), readings of the vehicle's inertial measurement units (IMU) (2241), and vibration sensors (2242) that detect unusual vibration of the vehicle, for example, from rumble strips, alert strips, speed bumps, gravel, and potholes. Human sensors (2250) include eye movement sensors (2251) consisting of at least one imaging device, foot position sensors (2252) and hand grip and contact area on steering wheel sensors (2253), and aural (2254) sensors. Human sensors have been discussed in detail previously, and also in FIGS. 7a-14c1. In this disclosure, road facing cameras in smartphones can be used in the place of visible cameras (2211). Smartphones can also be used as eye movement sensors (2251) and aural sensors (2254).

Figure 23:
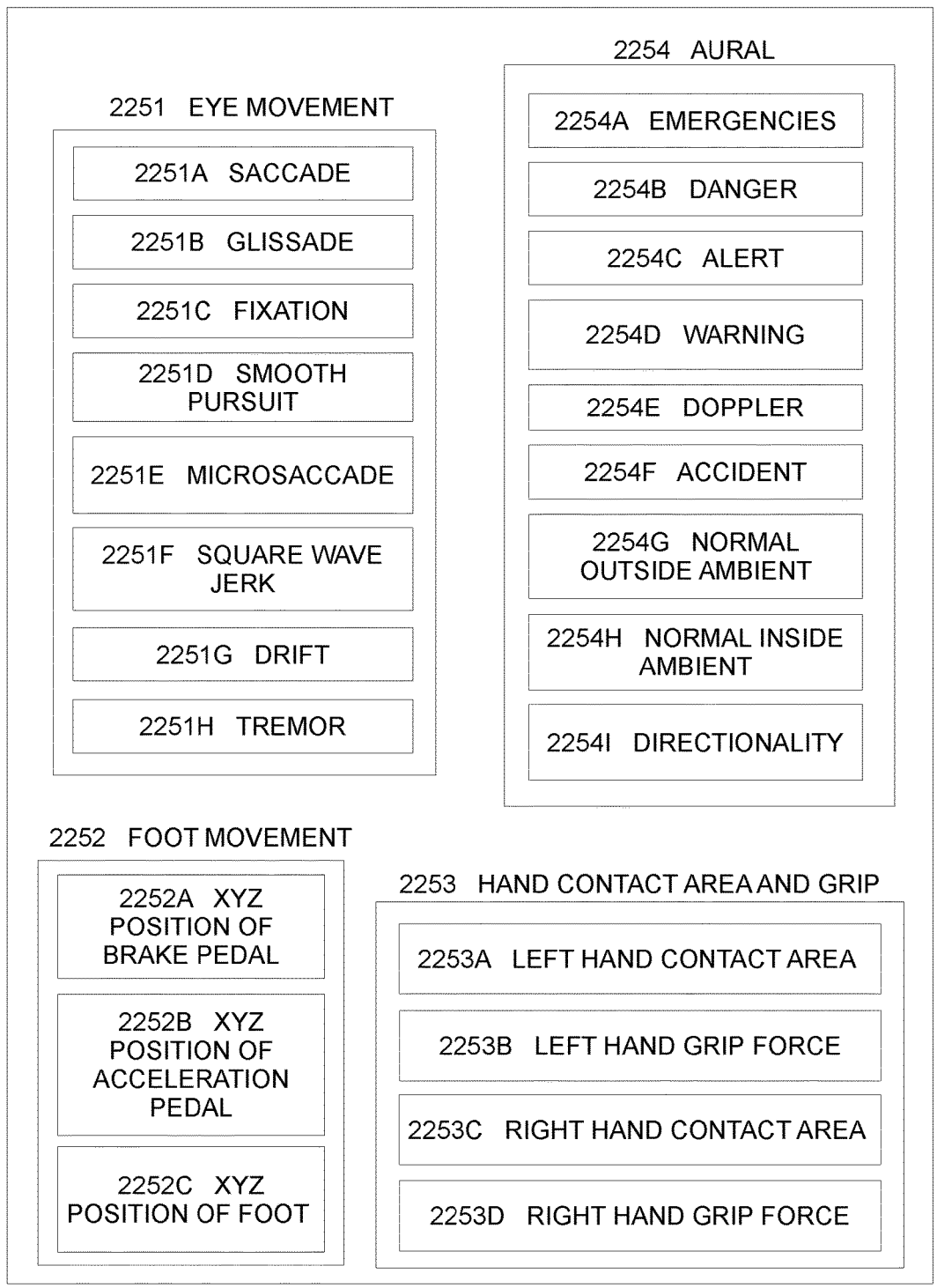
FIG. 23 shows aspects recorded by human sensors.

FIG. 23 shows the different kind of human sensors (2250) used, and the events they record. Eye movement sensors (2251) detect the following eye movement events: saccades (2251a), glissades (2251b), fixations (2251c), smooth pursuits (2251d), microsaccades (2251e), square wave jerks (2251f), drifts (2251g) and tremors (2251h). Foot movement sensors detect three aspects: position of brake pedal (2252a), position of acceleration pedal (2252b), and position of the foot (2252c) of the driver. See FIG. 10b and FIG. 10c (and associated text) for details of aspects measured. The combination of 2252a, 2252b and 2252c helps make a determination of where the foot is with respect to the brake and accelerator pedals, and whether either one of them are being depressed, and to what extent they are being depressed. Hand contact area and grip sensors detect the hand contact area and grip on the steering wheel. The left hand contact area (2253a) and its grip force (2253b), and the right hand contact area (2253c) and its grip force (2253d) on the steering wheel are sensed and measured as discussed under FIG. 9a-9e (and associated text). Aural sensors (2254) detect sounds and its aspects like: emergencies 2254a (police, ambulance and other emergency vehicle sirens), dangers 2254b (sounds of wheels screeching, honking by other vehicles etc), alerting sounds (2254c), warning sounds 2254d (for example, police using handheld loudspeakers for warning), Doppler detection 2254e (for example, to detect if a police siren is approaching the vehicle or receding away), accidents 2254f (sounds of crashes, fender benders, thuds). Aural events also include normal ambient sounds outside the vehicle (2254g) and inside the vehicle (2254h) (which in essence means no abnormal events are occurring) and directionality 2254i (direction from which a particular sound is coming from).

(Discussion of FIG. 24 follows the discussion of FIG. 26a.) FIG. 25 shows the categorization of event signatures (and their priorities) so that they can be stored, recalled and used appropriately. The priorities are not in any particular order. For example, priority B can be made the highest priority in an AV's software. The categorization process can use several variants. For example, it can be based on eye movements correlated with other human, vehicle, and outside sensors. For example, saccades to a point, fixation, and return saccades to that point followed by cautious slowing down could indicate a possible unsafe situation. However, a saccade to a point and immediate slowing down might indicate a more immediate danger. Such scenarios can be accompanied by rapid checking of the side-view and/or rear-view mirrors in anticipation of performing a cautionary action like lane change or complete stop. When analyzing this scenario for extracting training information, if there is any confusion as to what feature the eye had saccaded to because multiple objects were present in the line of sight but the objects are at different depths, autorefractor information (when available) of focal length of the eye's lens can be used determine what was fixated on. From this scenario, several concepts can be extracted, including the appearance of what features relative to the lane on the road require caution, judged distance to the feature, slow-down and braking profile depending on what the feature is, cautionary, defensive and evasive actions to be performed.

The event signatures include: Danger (priority A) 2501, Child (priority B) 2502, Efficiency (priority C) 2503, Courtesy (priority D) 2504, Special occasions (priority E) 2505, Weather related (priority F) 2506, New traffic situation (priority G) 2507, Unclear situation (priority H) 2508, Startled (priority I) 2509, Unexpected objects (priority J) 2510, Unexpected actions of others (priority K) 2511, Sudden actions of others (priority L) 2512, Comfort levels-speed, distance (priority M) 2513, Environment (low-light, sun-in-eyes, high-beam) (priority N) 2514, and Legal (priority O) 2515.

Event signature Danger (2501) relates to events that are dangerous, with potential for human injury or property damage. For example, consider a scenario where a potential accident was averted when a heavy truck entered a road without yielding. The event signature can include eye movements (like saccades, fixations, slow tracking), binaural recording, along with hand and foot sensor data, all combined with road facing video of the time-segment where a collision with this truck could have potentially occurred, but the driver took evasive action to avert this accident.

Event signature Child (2502) relates to events associated with a child, either averting an accident, or driving cautiously in expectation of an unpredictable, illegal or unexpected action by a child. For example, consider a scenario in which potential injury to a child was averted. The child, along with a caregiver, are walking straight ahead along a sidewalk of a road. The driver on the road notices the child turning back and looking at a bird on road's divider. The driver slows down expecting the child to cross the road to pursue the bird. The caregiver is unaware of what is going on. As expected, the child lets go of the caregiver and darts across the road. The driver is already slowing down and completely alert, and is prepared to stop, and does stop one meter from the child. Eye movement data, hand and foot sensor data, and forward looking video are all analyzed to extract relevant information and formulate an event signature.

Event signature Efficiency (2503) relates to events that help in improving efficiency of transportation. This can be, for example, taking the shortest route, or taking the fastest route, or avoiding to the contribution of traffic congestion on a particular segment of a path. These scenarios are typical in congested portions of large cities. The driver takes side routes which are slightly longer, but helps get to the destination faster, and also helps prevent congestion at a particularly notorious segment.

Event signature Courtesy (2504) relates to actions of the driver that lend to politeness, civility and courtesy. This can be, for example, the driver slowing down to let another car enter the lane. In this situation, there is no other need or indicator for slowing down, including legal (traffic signs or laws), traffic conditions or other event categories. Eye movement data, aural data, hand and foot sensor data, and forward looking video are all analyzed to extract relevant information and formulate an event signature.

Event signature Special Occasions (2505) relates to non-normal occasions, and the driver's response to it. For example, consider a situation where traffic diversions are in place for a popular tennis match. Roads approaching the venue have traffic diversion signs. However, these signs are on road-side and of the moving/scrolling display type. Such signs are not in the database of regular traffic signs. The driver follows these diversions, although this route is not the optimal one as per the map of the region. In ordinary circumstances, this action by the driver will be deemed inefficient and scored low. However, if the time-period for the segment of the path has already been indicated as Special Occasion (as obtained, for example, from a remote information server), and the driver follows the diversions, then the actions of the driver will be used to extract an event signature. Such a signature can include: saccading to the road-side display, which becomes a new region of interest (ROI), and saccades/smooth pursuits following the scrolling/moving letters within this ROI, while saccading back and forth to the traffic ahead, slowing down (foot movement) to read the signs, and gripping the steering wheel a little tighter.

Event signature Weather Related (2506) relates to environmental (local weather) characteristics that cause a driver to change driving characteristics. For example, during a first rain, roads becomes slippery, and an experienced driver will slow down much more than usual when turning. During subsequent rains, the magnitude of slowing down will reduce. As another example, on a rainy day with wet and slippery roads, the driver will maintain a longer following distance, be more vigilant when traffic is merging, foot will be more often hovering over the brake, with a lot more alternating acceleration and braking, while the hands are firmly gripped on the steering wheel, and there are a lot more saccades towards adjacent lanes.

Event signature New Traffic Situation (2507) relates to the driver's behavior during changed traffic situations. This can include accidents ahead, lane closures, and certain segments being converted to one-way roads. These situations will generally be a surprise to drivers. Their response to these situations will deviate from the normal, and the routes they take will vary from what is required by a map or a trip-plan. Hand and foot sensors will detect some indecisiveness (unusual slowing down, foot off the accelerator and hovering over the brake, with intermittent pressing of the brake pedal, both hands on steering), while eyes will register regions with unusually slowing traffic (saccades to various portions of oncoming as well as on-road traffic) which is confirmed by forward looking camera video.

Event signature Unclear Situation (2508) relates to situations when the driver is not sure of what to do next. For example, when lane markers on roads are faded, drivers unfamiliar with the segment of the path will be confused as to the lane boundaries. This can translate into the foot getting off the accelerator and hovering over the brake pedal without depressing it, even though the speed limit for that segment is much higher. Other examples include: a situation when traffic lights are malfunctioning, or when another car has turned on its turn-indicator but is not entering the lane on which the driver is. Lack of clarity in these situations can be traced from saccades to and from different ROIs, hand grip pressure and foot position. Aural sensors may not detect any abnormality in ambient sounds.

Event signature Startled (2509) relates to an event in which the driver is startled. In such a situation, the driver becomes alert instantly. The hand-grip tightens instantly, with more number of fingers and more surface area of the palms making contact with the steering wheel. The foot instantly gets off the accelerator and moves over the brakes, usually depressing the brakes at least slightly. Eye movements will indicate rapid saccades between very few ROIs. An example is when a truck behind sounds its air-horn unexpectedly. Another example is a very small bird flying across the road right in front of a car (for example, bird is entering the road 5 meters ahead when the car is traveling at 40 km/hour), startling the driver. The bird has no potential to damage the car. There will be a sudden foot movement from the accelerator to the brake, instantaneous grip and more contact area on the steering wheel, a saccade to the bird and then a very short and rapid smooth pursuit tracing the bird as it flies away, the steering wheel grip-force relaxing almost instantly but slower than at the beginning of this event (when the bird was first sighted) and the foot going back to the accelerator. This example event lasts around three seconds.

Event signature Unexpected Objects (2510) relates to an event in which an unexpected object appears to the driver. In such a situation, the driver becomes alert gradually (for example, as the object comes comes closer and its visual clarity increases). The hand-grip tightens gradually, with more number of fingers and more surface area of the palms making contact with the steering wheel as the object comes closer. The foot gets off the accelerator and moves over the brakes gradually. Eye movements will indicate a saccade to the object, and then fixations and saccades within this region, and then a saccade to the rear-view or side-view mirror, and then a saccade back to and within the object ROI. An example is a large bird hopping across the road 100 meters ahead while the vehicle is traveling at 60 kn/hour. The bird has no potential to cause major damage to the car. There will be a slow foot movement from the accelerator to the brake (which is not depressed) while a saccade to and within the ROI that defines the bird. This is followed by a slow smooth pursuit as the bird hops away from the road, the steering wheel grip force relaxing and the foot going back to the accelerator. This example event lasts over 3 seconds. Another example is pieces of shredded tire on a highway appearing starting 200 meters ahead while traveling at 100 km/hour.

Event signature Unexpected Actions of Others (2511) relates to events that are dictated by the actions of other vehicles. For example, when a car in front travels at 60 km/hour on a highway marked 100 km/hour, the drive is forced to slow down. Such an event is usually accompanied by saccades to the object in front, then to the rear-view mirror and then side-view mirror, while the foot moves from the accelerator to the brake pedal, and the steering wheel grip has tightened slightly along with a greater contact area. The driver is not startled, and the car in front is not an unexpected object.

Event signature Sudden Actions of Others (2512) are events that where the actions of other vehicles on the road lead to a driver performing a reflexive or conscious action. For example, when a vehicle in an adjacent lane swerves very slightly (but stays within its lane) towards the lane of a driver, the driver swerves away instantaneously but slightly, and then slows down a little. Eye movements will indicate a sudden saccade as the swerving vehicle enters the peripheral vision. The saccade is followed by almost instantaneous foot movement away from the accelerator and onto the brake, which is depressed (there is no hovering over the brake, the foot depresses it immediately), while hand-grip and contact-area values increase instantly. The time period for this example event is about one second.

Event signature Comfort levels (2513) are event signatures surrounding drivers' attempts to adjust driving parameters to suit their comfort levels. This can be, for example, adjusting following distance, speed, lane position, preference for a longer route rather than taking a much shorter but crowded route, or avoiding driving close to very large vehicles. These events typically last much longer, with most sensor readings spread over a larger time and lower amplitudes (slower foot motions, grip on steering wheel is lighter and has less contact), including slower speeds and higher latencies for saccades, near-absence of microsaccades, and very low amplitude glissades. An example is when a driver driving on a divided multi-lane highway with sparse-traffic encounters a long segmented-trailer (carrying two levels of cars) ahead. The driver is uncomfortable driving behind this trailer, and prepares to get ahead of it by switching lanes and merging back. Slow saccades are directed to the rear-view and side-view mirrors, and a gradual speeding up of the car (foot stays on the accelerator since there was no prior braking for several minutes before of the start of this event) occurs. The steering wheel is gripped a little tighter than before (the previous grip was of very low value, and the contact was only three fingers of one hand, the present grip becomes slightly tighter and with two hands and more fingers engaged). Saccades to the trailer, rear-view and side-view mirrors can all be, for example, one to two seconds apart during the lane change procedure. After the lane change and getting ahead of the trailer (for example, after 15 seconds), switching back to the original lane involves slow saccades, mostly directed to the rear-view and side-view mirrors.

Event signature Environment (2514) relates to driving behaviors that are affected by the environment. Examples are low-light levels, sun straight-ahead and low on the horizon, high-beam lights of oncoming traffic. When any of these events happen rapidly or unexpectedly, the driver slows down, maintains a longer following distance, is more cautious, all of which mostly translate to foot hovering over or depressing brakes, tighter grip and higher contact area on the steering wheel, without affecting saccades, glissades and microsaccades.

Event signature Legal (2515) relates to the actions of drivers while following legal guidelines. For example, a driver stopping the car at the instruction of a police officer waving for the driver to pull over, or giving way to a ministerial motorcade, or pulling over for a random roadside breath-test. These events are not routine in any segment of a path, and may not happen to every driver on that segment. They can appear slightly similar to stopping at traffic lights, but are distinguishable because there are no traffic lights on the corresponding map. These events can be accompanied by the driver pulling away from the road and onto a side or a non-road area. They can also be a general slowing down, with slow tracking of the slower vehicles on the passenger's side (faster traffic is on the driver's side).

FIG. 26a shows a human event occurrence detection scheme, while FIG. 26b shows how this detection scheme feeds data into an analysis scheme to extract signatures and use it to train AVs. This scheme is used to make a determination as to when an outside event (event outside the car) has occurred. The sensors are continuously capturing data. However, not all of this data necessarily goes towards training an AV. Specific events occurring on the outside of the vehicle are correlated with human sensor (2250) data, outside environment sensor (2210) data, and vehicle sensor (2230) data. Eye movement events (like saccades, fixations) and aural events (non-normal sounds like ambulance sirens, honking) are classed as primary human events, while foot events (like foot going off accelerator, depressing brake pedal) and hand events (increasing the grip and contact area on steering wheel) are classed as secondary human events. When at least one each of primary and secondary human events have occurred within a defined time-frame, there is a possibility that this was caused by or in anticipation of an outside event. In FIG. 26b, these human events are compared to the pre-existing map (associated with this part of the road) to confirm if the human events correspond to an outside event, and if there is no correlation, the conclusion is that no outside event has occurred. If there is a correlation, then there is an expectation that an unusual outside event has occurred to which the driver is responding. For example, on a divided highway with sparse traffic, drivers might increase speed when they realize they are driving below the speed limit, or decrease speed when the speed has increased over the speed limit. However, there was no outside event that caused these actions, and therefore no correlation between the human events and what is happening outside the car. Similarly, when following a routine path home from their workplace, drivers will have the usual patterns of saccades, glissades, microsaccades, fixations, hand and foot sensor readings, and similar aural recordings. In these cases, an unusual outside event has not occurred to cause a change in their normal driving pattern.

In FIG. 26a, data relating to eye movement (2351), aural (2354), foot (2352) and hand (2353) are fed to eye movement event comparator (2601), aural event comparator (2604), foot event comparator (2602) and hand event comparator (2603), respectively. The comparison is between the respective events at time T and time T−ΔT, where ΔT is a small increment in time, wherein ΔT can be chosen to be a value appropriate for the scenario, for example, anywhere in the range 0.1-2 seconds. ΔT can also be chosen to be higher. As an example, if the probability of an outside event occurring is very low, as when driving on an isolated long desert highway with straight roads, ΔT can be 1 minute or higher. This comparison helps determine whether a change in a human event has occurred in the time period ΔT. Thresholds can be set to determine what constitutes a change. For example, a 25% increase in hand contact area on the steering wheel and/or a 50% increase in total grip force on the steering wheel can be set as the minimum for triggering a change-determination. Similar threshold settings can be used for other human events. The thresholds can be tailored for individuals, segment/path locations (for example, rural versus urban), male/female drivers, type of vehicle being driven, time of day, day of the week, and other factors. If no change has occurred, the comparison continues starting with T incremented by ΔT. If a change has indeed occurred, then a check is made (2610) to see if at least one each of primary and secondary human events have changed for this time period. If the answer to this in the negative, then the determination is made that no outside event has occurred (2611). If the answer is affirmative, then an outside event has probably occurred (2612), and the human events are compared (2613) with the map corresponding to the path segment for the same time period T−ΔT to T. The results of this comparison are shown in FIG. 26b. It should be noted that while all these comparisons are going on, each of 2351-2354 are continuously feeding data to each of 2601-2604, respectively. This process continues irrespective of the outcomes at 2601-2604 and 2610. Regarding eye movements, it should be noted that tremors and drifts can be used as alternatives or to augment fixation detection. Similarly glissades can be used as alternatives or to augment saccade detection, or for detecting the end of a saccade. The notation Q is a binary variable used to detect the end of the current event by making a continuous check of its value. Q helps terminate the loop when an expected event has occurred. Before the start of an outside event occurrence subroutine, Q is set to zero. In FIG. 26b, if an outside event has occurred (i.e. what has occurred is not an expected event when compared to the map), then Q is set to 1. If an outside event has not occurred, there is no point in continuing the loop, and therefore Q is set to 0 so that the loop can exit (and continue with FIG. 26a: detecting if an outside event has occurred or not). If Q=1, the loop continues until the unexpected event has ended, at which time the loop exits with Q=1 and proceeds to retrieve data from the cache for the duration of the outside event. Event start time EST is used to keep a track of when the event started.

FIG. 26b shows a scheme for event signature extraction, categorization, map update and training software update by using human event data from FIG. 26a after confirmation that an outside event has occurred. The human event is compared to the corresponding map segment to see whether this was an expected event. For example, if the map indicates that there is a traffic light for the segment at a point corresponding to when a driver stopped the car (saccades to the traffic light above and ahead of the car, hand contact area increased slightly, foot off the accelerator and over the brake and slow depressing of brake to come to a complete but rolling stop), then there was probable cause for the car to have stopped on the road. Since events can be of different durations, EP (event period) is used to track how long the event lasts. EP and EST indicate the total duration of this particular event and when it started. As can be seen in FIG. 26a, EP was initialized to 0 before starting the event-checking loops. In FIG. 26b, EP is incremented by time segments ΔT as long as the unexpected event continues, and once it has stopped, the loop exits. The use of the binary variable Q has been discussed previously. Data from the environmental sensors (2200) corresponding to this time segment (EST to EST+EP) are extracted from the cache and stored in a data vector. The signature extracted from this data vector forms the signature of the outside event which caused the human to act or react a certain way. This signature is compared to the existing signature database to see if it is a known signature, i.e, a similar event has occurred in the past. If it is a known signature, the signature's count is incremented in a user section of the map (the main map is not altered). If this is an unknown signature, then the signature is categorized under the scheme of FIG. 25 as to belonging to one of 2501-2515. This signature is then added to the appropriate category in the signature database, and also added to the user section of the map. The AVs training software is then updated. Over time, the signature base will grow, and so will the list in FIG. 25. Also, signatures already present, like Child (2501), will develop sub-categories because of variations that are being encountered.

Signatures will typically include identification of when, where, from who, and under what conditions each signature was collected, including timestamps, geolocation, details of subject operating the vehicle. They will also include a host of sensor data, including 2210, 2230 and 2250. Some of the concepts and data types used in signatures are discussed in later parts of this disclosure. Signatures are captured beginning from the start time of the signature (EST) to the end time (EST+EP, where EP is the event time period, i.e. how long the event has occurred). The frequency of capture within the time period EP can set be set by the user as a preference parameter. The inverse of this frequency is $\Delta T$ of FIG. 26a and FIG. 26b. The user can include the driver, the programmer of the software, people who administer the data capturing, a regulatory organization, or AV software makers. This frequency can be set to the outside front-facing visible video camera's frame rate, for example: 50 frames per second (fps), so that data is recorded every 20 milliseconds. Newer cameras, including consumer smartphones, have frame rates that are much higher, and therefore are desirable to better capture eye movement data (EMD) because of the speeds associated with saccades etc. However, the sampling frequency of other sensors (like foot, hand, speed, rain, headlight etc) need not be as high as that for eye movements. Instead, data can be captured at a lower frequency, for example, at every 100 ms for sensors like ultrasonic (2215), and every 500 ms for headlight, fog, rain sensors. Such optimizations can be carried out as a matter of routine trial and error depending on the types of road, conditions, vehicles, drivers etc. In the event signature dataset, $\Delta T$ is the same for all sensors, including eye movement sensors. Commercially available eye movement tracker software and systems are well-developed. Many can accurately capture all the eye movements mentioned in this disclosure when used with 200 fps cameras, while most eye movements can be captured with 30 to 100 fps cameras. Instead of using EMD available in a signature, that is, EMD that was captured every $\Delta T$, eye movement maps (for the entire EP) as in FIGS. 15b, 19b2, 20b, 21b as provided by commercially available eye movement analysis software can be used for the entire EP.

When outside events occur, signatures of the events are extracted. Several example scenarios were presented and analyzed previously. These included: an unaccompanied child at the edge of the road, a kangaroo on the road, a maintenance vehicle parked on the road, a ball rolling across a road, a large vehicle an an adjacent road that is not slowing down but intends to merge, a child on a bicycle on the edge of the road, a small dog on a leash, a large dog on a taut leash, a not-yet-visible ambulance. Features extracted from the video segments corresponding to outside events will typically include the features in the video segment that were saccaded to, or fixated at, or slow tracked, or an ROI formed, are extracted, along with the road and its outline (which serves as a reference/orientation marker) when necessary. These event-specific features will include the children, kangaroo, dogs with humans, rolling ball, maintenance vehicle, large vehicle (plus trace of adjacent road). Aural features associated with aural events, like the siren of the ambulance, will also be extracted from the aural segments corresponding to the outside events. The data is not stored in the signature as video or audio segments or still-image frame(s), but as feature nomenclature, properties, classification/categorization (for example: big dog, taut leash, dragging accompanying human, edge of road), geolocation, time/date. The signature will also have data related to vehicle inside and outside sensors, and human sensors as discussed in FIG. 22 and FIG. 24 and corresponding text. If necessary, video and/or audio segments can be stored in signatures for other purposes like later analysis and additional feature extraction, manual comparison at a later time, quality control, software capabilities development and enhancement, further training, archival or legal reasons. If there is a need to save storage space, the signature can either be stored without video clips, or with only a reference to the video clip (for example, a video clip serial number by itself or including date, time, geolocation, vehicle and environmental sensor data like speed and heading, weather, road lighting-level information etc).

When AVs (semi or full) are operating on roads, they continuously monitor road-facing video. The video is examined and features extracted in real-time using image analysis systems, which also tag the extracted features with nomenclature and categorization information. Extracted features are compared in real-time to features in the AV's database. However, the comparison is not video to video (or video-frame to video-frame) or audio file comparison of the current scenario to the database, but rather extracted features in the scenario (or features as they are being extracted in real-time) to the extracted features in the database, including the tagged information. As soon as a match between feature(s) from the real-time video to feature(s) in the signature database is made, the corresponding signature(s) in the database is tracked. The AV is triggered to start following patterns in the signature(s) while continuously monitoring the outside video to see if the feature(s) in it continue to correspond to the signature(s). These patterns are related to speed, braking, turning, indicating, lane change etc, as was done in the stored signature(s) that are now being followed. The video capture devices as well as the image analysis systems are prioritized and allocated extra resources for the features (since these were saccaded/fixated, slow tracked etc when the original signature was acquired by a human), for example, higher resolution and higher processing speed. The same applies to audio components if an aural event is detected.

As an example, when an AV's software has been updated with the signature of FIG. 17, and the AV encounters a similar situation (unaccompanied child approaching road), it will reduce speed (as was done by the human when the signature was captured) and analyze the ROI around the child at a higher priority and resolution, while reducing speed. Once an accompanying adult is detected, the previous higher speed is resumed. Without this updated software, the AV would have continued without reducing speed, and an accident could have probably occurred if the child was actually unaccompanied and/or entered the road. The additional benefit of using the updated software is that higher speeds can be maintained without being overly cautious, and rational speed decisions can be made depending on how the situation evolves.

When these signatures are used in the context of non-AVs, that is vehicles (real or virtual) operated by humans, the signature of good drivers (EDs—see later discussions) can be used as a benchmark for testing, ranking or scoring new drivers, or those without a ranking. This includes using the list of features extracted in the signatures of each driver, and the criticality of these features as obtained (visually determined through saccades, fixations, dwells etc) by each driver and comparing them to the benchmark.

FIG. 24 shows a version of the entire signature (SIGN) of a particular outside event. This representation of the signature (SIGN) is an array of SIG(t) at different time points. That is, SIG(t) is the data relating to SIGN as a particular time t, the first t being EST, then every $\Delta T$ (i.e. EST+$\Delta T$, and so on), the last being EST+EP, all of which are captured from each of the components of environmental sensors (2200). That is, SIGN={[SIG(EST)] [SIG(EST+$\Delta T$)] [SIG(EST+2$\Delta T$)] . . . [SIG(EST+*EP*)]}

SIG(t)={[SIGDEF] [2200]}(t);

where SIGDEF is the definition (informational aspects: who, when, where, what etc) of the signature:
[SIGDEF]={[SIGNAME][time][geolocation][SN][CN][SGN][PN]}, at time t
where SIGNAME is defined as: [SIGNAME]={[SIGCAT][SIGVAR][SIGVER][SIGFEAT]}
where SIGCAT is the category (2500) of the signature, which can be any one of 2501 to 2515, and SIGVAR is the variation type of the signature category (for example: child-unaccompanied child-unaccompanied child on bicycle-unaccompanied child on bicycle at edge of road, this variation is three levels deep from the main CHILD (2502)), SIGVER is the version number of the particular SIGVAR. SIGFEAT contains the features that were extracted during this signature, for example: very young child, small dog, large dog, adult accompanying child, leash, kangaroo, maintenance vehicle. These are not images of these features, but their nomenclature, classification, categorization. SIGFEAT is an array, also includes the relative criticality value of these features in braces. An example SIGFEAT corresponding to FIG. 21 is:
SIGFEAT[large_dog(4), 0.5m_to_road_edge(2), accompanying_human_strained(1), taut_leash(3)], which means that the feature of the accompanying human who is strained is the most critical feature in this array. Criticality can be proportional to any or a combination of: dwell time on a feature, fixation time on a feature, number of saccades to the feature.

Time and geolocation are the timestamp and GPS location, SN is the subject number, CN is the condition number, SGN and PN are the segment and path numbers (discussed later, under FIGS. 30*a*, 30*b*, 30*c*). At every time t, environmental sensor data captured includes (as in FIG. 22):
[2200]={[2210][2230][2250]}, and
[2210]={[2211] [2212] [2213] [2214] [2215] [2216] [2217] [2218] [2219] [2220] [2221]};
[2230]={[2231] [2232] [2233] [2234] [2235] [2236] [2237] [2238] [2239] [2240] [2241] [2242]};
[2250]={[2251] [2252] [2253] [2254]}, which corresponds to {[EMD][EPO][ESCAF][AUR]}.

Binaural (or aural when binaural is not available) data AUR(t) is stored at every time t, which is actually the sound for a time segment (and not a discrete time-point). For example, the first AUR(t) is AUR(from EST to ΔT), the second one is AUR(from (EST+ΔT) to (EST+2ΔT)), the third is AUR(from (EST+2ΔT) to (EST+3ΔT)), and so on. The last one is AUR(from (EST+EP-ΔT) to (EST+EP)).

Although the schemes of FIG. 26*a* and FIG. 26*b* use information from all four types of human sensors (eye movements: 2251, foot position: 2252, hand grip and contact area: 2253, aural: 2254), not all four are needed to detect outside events and non-events. For example, any one of the following combinations can be used: (2251, 2252), (2251, 2253), (2254, 2252), (2254, 2253). It can be seen that these combinations require at least one from each of the two groups to be used, the first group being primary human sensors (eye movement and aural sensors), the second group being secondary human sensors (foot and hand contact area/grip sensors). However, reduction in the number of human sensors will cause a reduction in types, number and sensitivity of the outside events captured, and therefore lead to lowered variety, quality, fidelity, robustness and reliability of the event detection and capturing system.

FIG. 27 (appearing in the same sheet as FIG. 37) shows non-event categories (and their weightages) which are used to rank subjects. When outside events are absent, the driving is a non-event mode. A detection scheme for detecting non-events is not used, but categorization and evaluation schemes are used. These categories are used to determine driving quality and traits of a driver in situations of normal/routine driving where no unexpected or abnormal outside events (like accidents, ambulances approaching, kids crossing the road etc) have occurred in a path's segment. Although no event has occurred, the driver is evaluated on the quality of driving over a particular segment of a path. The following categories are used for the evaluation, each having a weightage: Lawfulness (weightage: −10 to +10) 2701, Safety (weightage: −10 to +10) 2702, Responsiveness (weightage: −10 to +10) 2703, State (weightage: −10 to +10) 2704, Defensive (weightage: −10 to +10) 2705, Skill (weightage: −10 to +10) 2706, Conduct (weightage: −10 to +10) 2707, Knowledge (weightage: −10 to +10) 2708.

Lawfulness (2701) relates to following the law (road rules or traffic related laws), including those related to speed, right of way, traffic lights and signs.

Safety (2702) relates to the driver's actions that keep the driver as well as other vehicles and pedestrians on the road safe, including maintaining proper following distances and speeds depending on pattern and speed of traffic, nature and sizes of road.

Responsiveness (2703) relates to the driver's response to normal situations around the driver. For example, if the driver reduces speed gradually during an expected traffic stop (coming to a rolling stop instead of an abrupt stop), then the driver scores high on responsiveness.

State (2704) refers to the state of driving and relates to the driver's mental state directed to the tasks that are important. A subject can drive in one or a combination of states: vigilance, concentration, attention, distraction and lapse. If the driver is distracted by billboards on buildings or buses, or by people or objects on sidewalks that in no way have the potential to have an effect on the road (for example, a mime performing on the sidewalk), then the driver scores low on State.

Defensive (2705) relates to defensive driving. They assume others will make driving mistakes and recognize hazardous driving by others and make defensive maneuvers before an outside event occurs. For example, at an intersection, even when a van's driver (driver V) has the right of way, driver V looks at the driver of a car (driver C) slowing down at a yield sign to make sure that driver C has noticed driver V, and is not distracted and therefore will not drive into driver V's lane.

Skills (2706) relates to the driver's skill in driving along various types of paths (city, rural, suburbs) under various factors (sun-in-eyes, night time, rain, fog). Reduced skill indicators include: indecisiveness, last minute changes, unnecessary or sudden deceleration, and poor stopping (too close to the bumper of the vehicle in front).

Conduct (2707) relates to the driver's conduct on the road. For example: proper acceleration and deceleration at stop signs and traffic lights, slowing down gradually when approaching a pedestrian crossing so as not to alarm pedestrians. Conduct and Responsiveness are distinct from Lawfulness since a driver can be driving lawfully but have poor driving conduct and response.

Knowledge (2708) relates to the driver's knowledge of the physical world he is in, including understanding of path layouts (road delineation, cycling path, tram path, shared paths), traffic rules, awareness of timings of traffic congestion. A driver new to the city might have poor knowledge of the layout of roads.

FIG. 28*a* shows a scheme to categorize and score failure and success of a subject operating a vehicle on a segment in a path. This scheme is applicable to outside events. It should be noted that the scoring factors mentioned below can be combined, or split into finer aspects, or new factors can be derived from the broad factors described. The weightages can be re-assessed and new ones prescribed. Types of failures are categorized under Failure Scoring of Subject (2801). These are actions or inactions of a vehicle's operator that negatively affect the well-being of both the subject as well those around the subject, and the subject's vehicle as well as property around the vehicle, including other vehicles. subject Primary Failure (2801a) results in severe human injury and danger to life, and has the highest weightage of between 100× and 50×, where "x" is the multiplication operator. A weightage of 100× indicates every instance of occurrence is multiplied by a factor of hundred 100 when arriving at a total failure score. In an embodiment, the scheme can be setup so that Subjects can be eliminated as soon as their scores reach a certain threshold, for example, causing a major accident or an accident leading to loss of life.

Subject Secondary Failure (2801b) results in medium human injury requiring hospitalization, but no danger to life, and has a weightage of 49×-25×. This type of failure has a potential to have caused Subject Primary Failure (2801a), although it does not actually cause it.

Subject Tertiary Failure (2801c) results in minor human injury not requiring hospitalization, but requiring first-aid, and causes no danger to life, and has a weightage of 24×-13×. This type of failure has a potential to have caused Subject Secondary Failure (2801b), although it does not actually cause it.

Subject Quaternary Failure (2801d) results in human injury not requiring any medical attention or first-aid. This failure does not cause any danger to life, but causes medium damage to property, and a potential to have caused Subject Tertiary Failure (2801c), and has a weightage of 12×-6×.

Subject Quinary Failure (2801e) results in minor damage to property, and a potential to have caused Subject Quaternary Failure (2801d), and has a weightage of 5×-2×.

Subject Senary Failure (2801f) does not result in any damage to property and has no possibility of causing human injury, but has a potential to have caused Subject Quinary Failure (2801e), and has a weightage of 1×.

Subject Septenary Failure (2801g) has no possibility of causing damage to property or human injury, but has a potential to have caused Subject Senary Failure (2801f), and has a weightage of 0.1×.

Types of actions of an operator of vehicle that result in a successful traversal of a segment of a path are categorized under Success Scoring of Driver (2802). These are actions of a vehicle operator that lead to events that positively affect the well-being of both the operator as well those around the operator, and the operator's vehicle as well as property around the vehicle, including other vehicles.

Subject Primary Success (2802a) results in preventing severe human injury and danger to life, and has the highest weightage of between 100× and 50×.

Subject Secondary Success (2802b) results in preventing medium human injury that might have required hospitalization, but did not pose danger to life, and has a weightage of 49×-25×.

Subject Tertiary Success (2802c) results in preventing minor human injury that would not have required hospitalization, but might have required first-aid, and could not have caused any danger to life, and has a weightage of 24×-13×.

Subject Quaternary Success (2802d) results in preventing human injury not requiring any medical attention or first-aid, but could have caused medium damage to property, and has a weightage of 12×-6×.

Subject Quinary Success (2802e) results in preventing minor damage to property, and has a weightage of 5×-2×.

Subject Senary Success (2802f) results in preventing sudden changes in speed, direction or distance, and has a weightage of 1×.

From the preceding figures and discussion, it can be seen that the determination that an outside event has occurred is based on the concept that outside events are associated with at least one of each of primary and secondary human sensors. The hands turn the steering wheel to change the direction of the vehicle, and the foot acts on the brake and accelerator pedals to change the speed of the vehicle. In this disclosure, these two aspects: change in speed, and change in direction, are called primary vehicle events. In the absence of secondary human sensors, sensing related to primary vehicle events (change in the speed or direction of the vehicle) can provide a rough, low-resolution, low-fidelity approximation of foot and hand movements. Direction and speed sensing is readily available in non-autonomous vehicles in the form of odometer and clock readings augmented with geolocation (GPS, IMU in mobile phones, or incorporated separately into vehicles). The trade-off is lowered variety, quality, robustness and reliability of the event detection and capturing system. For example, consider a situation where the hand-grip on the steering wheel has suddenly increased due to the driver getting prepared for a child on the roadside possibly about to enter the road. The driver is now prepared for an imminent emergency maneuver. However, the child's parent was alert and grabbed the child, and the driver did not have to turn the steering wheel. In this case, there will no change in direction of the vehicle, so the event will not be captured—although the event could have been potentially life threatening, and might be so the next time it happens since there was no capture and no learning of the outside event. Similar to the case of replacement of hand sensors with vehicle direction sensors, foot sensors 2252 can be replaced with vehicle speed change sensors. In the same scenario as discussed for the hand sensor replacement, the driver removes his foot from the accelerator (but the speed doesn't reduce significantly enough for the GPS/IMU to sense this) and moves it over the brake pedal. These actions of removing the foot from the accelerator and hovering over the brake pedal is not captured by the speed change sensors. The foot is initially hovering, for example, 5 cm away from the brake pedal. As the vehicle approaches the child, the foot is resting on the accelerator but not depressing it. None of these actions are captured by the speed sensors, and there will be no learning, although the event could have been potentially life threatening, and might be so the next time it occurs. When a vehicle is moving, there are minute changes in both its speed as well as direction occurring all the time. As to what magnitude of change in the vehicle speed or direction constitutes a change in the vehicle primary event, this determination is left to the user. Some example thresholds for speeds include: a change in the speed by 0.25 km/hr, or by 2% of the present speed, or by 2% of the present speed in less than 3 seconds, or by 0.25 km/hr in less than 2 seconds, or 0.5 km/hr in 10 m, and so on. Another example criterion is: in a span of 3 seconds, a change of 1 km/hr at speeds below 20 km/hr, by 2 km/hr at speeds between 20 and 45 km/hr, by 3 km/hr at speeds between 45 and 70 km/hr, by 4 km/hr at 70 km/hr and above. Some example thresholds for determination that a change in direction has occurred include: 2 degree in 3 seconds, or 2 degrees in 3 seconds, 5 degrees over the course of 15 meters. Another example criterion is: in a span of 4 seconds, a change of 10 degrees at speeds below 20 km/hr, by 6 degrees at speeds between 20 and 45 km/hr, by 3 degrees at speeds between 45 and 70 km/hr, by 2 degrees at 70 km/hr and above. Another example criterion is: in a span of 50 meters, a change of 3 degrees, or a change of 5 degrees.

The previous paragraph discussed the differences between vehicle direction and speed change sensors, and the use of hand and foot sensors. The latter captures the intent of the driver, even though brake pedal depression or vehicle turning has not occurred. Similarly, eye movement sensors also capture intentions of the human before the human performs an operation. Hearing is mostly passive because it captures only what is coming into the ears, and aural sensors are similar in nature. They do not seek out information, nor do they perform an action. Therefore, human sensors for eye movement 2251, foot 2252, and hand 2253 are able to detect human intentions as well as actions. Humans exercise mental components when driving, which are aided by information from the senses, and result in intentions as well as actions. These mental components are termed Instrac components in this disclosure, and are discussed in greater detail below. Eye movements, hand contact area and grip force on the steering wheel, and foot movement (foot position with respect to accelerator and brake pedals) all are linked to underlying Instrac components.

Figure 28B:
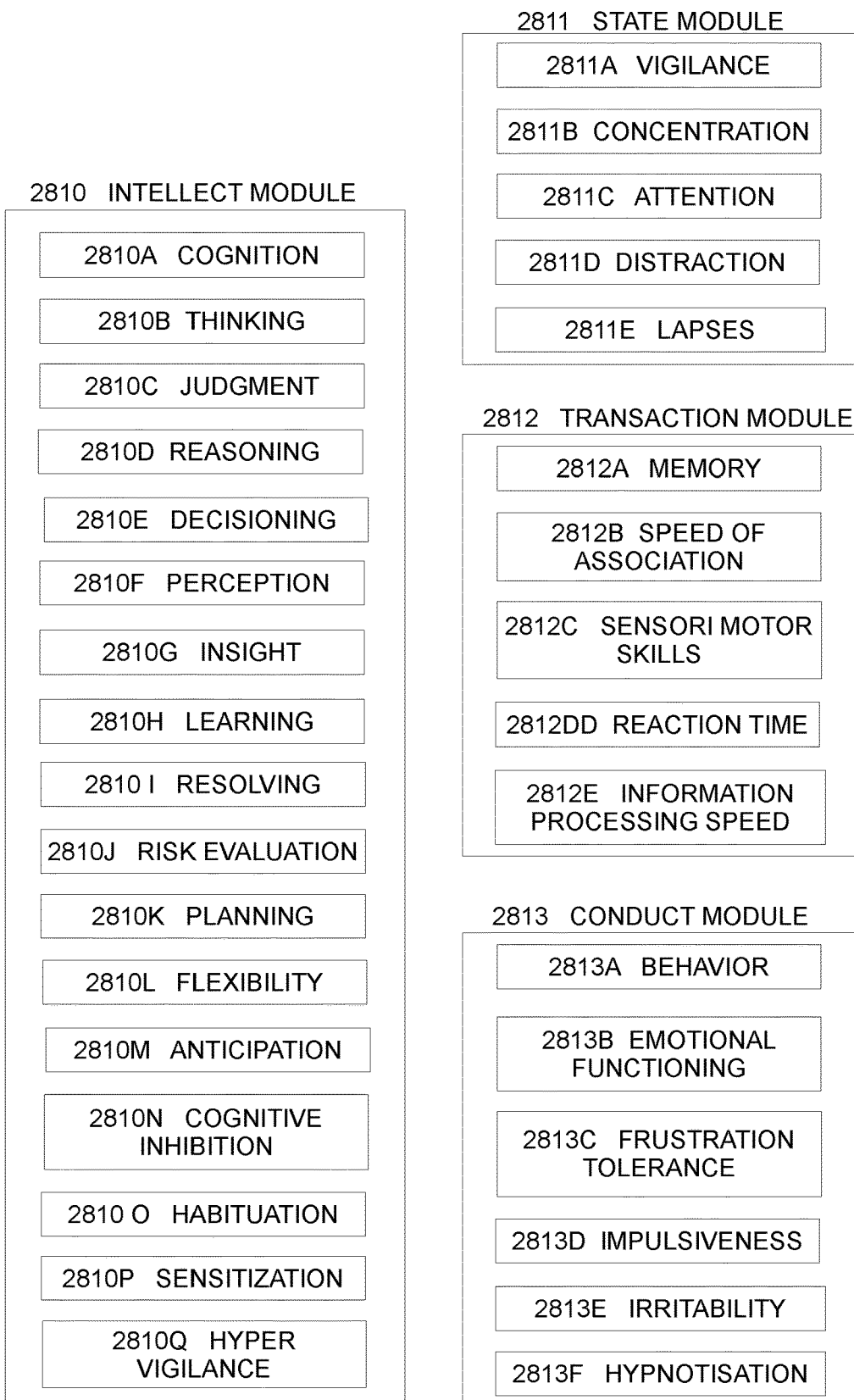
FIG. 28b shows Instrac components used to evaluate driving.

FIG. 28b shows an embodiment in which Instrac mental components that humans exercise when driving are used to evaluate driving. Instrac components are divided into four modules, each having sub-components. The four modules are: Intellect Module 2810, State Module 2811, Transaction Module 2812, and Conduct Module 2813.

Intellect Module 2810 has 17 components. Cognition 2810a: is the acquisition of knowledge and understanding through thought, experience, and the senses. Thinking 2810b is the mental processing of information using abstraction, logic, imagination and problem solving. Judgment 2810c is the forming of opinions, conclusions, and evaluations based on information. Reasoning 2810d is the use of thought to identify, evaluate, and decide upon a solution to a problem. Decisioning 2810e is the use of strategies to plan ahead for a response. Perception 2810f is the process of recognizing and interpreting sensory stimuli. Insight 2810g is the understanding of inner nature. Learning 2810h is the understanding of cause and effect based on identification of relationships and behaviors. Resolving 2810i is the process of finding an answer or solution. Risk Evaluation 2810j is analyzing the positive and negative outcomes of different options or choices. Planning 2810k is the process of thinking about activities required to achieve a desired goal by creating and maintaining a plan. Flexibility 2810L is the process of adapting by re-configuring resources, shifting perspective, and balancing competing demands. Anticipation 2810m is the state of expectation about an upcoming event or situation. Cognitive inhibition 2810n is the unconscious tuning out of stimuli (visual, auditory, motion, tactile) not relevant to the current task. Habituation 2810o is the decreased response due to repeated encounter of the same stimulus. Sensitization 2810p is the increased response due to previous encounter of a similar stimulus. Hyper vigilance 2810q is the excessive and heightened arousal and sensitivity to sensory stimuli.

State module 2811 has five sub-modules. Vigilance 2811a is the constant lookout for stimulus over prolonged periods of time. Concentration 2811b is the focusing on task at hand while ignoring distractions. Attention 2811c is the focused awareness on a subset of perceptual information. Distraction 2811d is the process of paying attention to irrelevant stimuli. Lapse 2811e is the temporary brief shifts of conscious attention away from some primary task to unrelated task.

Transaction module 2812 has five sub-modules. Memory 2812a is the storage and retrieval of information in the human brain. Speed of Association 2812b is the speed at which mental connections between concepts, events, or mental states are made. Sensori Motor Skills 2812c is the process of receiving sensory messages (sensory input) and producing a response (motor output). Reaction Time 2812d is the time it takes to respond to a stimulus (which can be measured in the case of the foot on/off the accelerator/brake pedal or hand grip force and contact area on the steering wheel. Information Processing Speed 2812e is the measure of how quickly a person can comprehend a situation and take in the relevant information.

Conduct Module 2813 has six sub-modules. Behavior 2813a is the conscious and subconscious response and mannerisms to stimuli. Emotional functioning 2813b is the state of feeling resulting in physical and psychological changes that influence thought and behavior. Frustration tolerance 2813c is the calmness, anger, annoyance and disappointment exhibited as the emotional response to opposition. Impulsiveness 2813d is the process of acting on a whim, with reduced forethought, reflection, or consideration of consequences. Irritability 2813e is excessive and easily provoked anger, annoyance or impatience. Hypnotisation 2813f is the altered state of awareness caused by sustained stimuli of the same kind that leads to lapses. This can occur, for example, when driving along long stretches of straight roads with the same scenery.

These components can be a combination of other components or modules of Instrac. Such permutations and combinations can be decided by assessor assessing drivers, and will depend on specific situations, for example: a system to improve autonomy of a particular model of vehicle plying on a specific segment of a path in a small town in the Australian outback. For this example, cognition 2810a can also be construed as a combination of just three sub-modules of the Intellect module 2810: Thinking (2810), Reasoning 2810d, Perception 2810f, and none from the State, Transaction and Conduct modules.

Instrac sub-modules can be broadly divided into two groups: sub-modules that are particularly prone to human weaknesses, but are strengths of machines (software and hardware), and sub-modules that are particularly prone to machines (software and hardware) weaknesses, but are strengths of humans. It is advantageous to eliminate drivers with human weaknesses, and to promote humans who perform well in the areas of machine weaknesses.

Human weaknesses are the sub-modules of: Vigilance, Concentration, Attention, Information processing speed, Reaction time, Sensori Motor skills, Lapses, Memory, Planning ability, Behavior, Emotional functioning, Frustration tolerance, Impulsiveness, Irritability and Hypnotisation.

Human strengths are the sub-modules of: Cognition, Cognitive inhibition, Habituation, Sensitization, Thinking, Judgment, Reasoning, Decisioning, Perception, Insight, Learning, Resolving, Risk Evaluation, Flexibility, Speed of Association, Anticipation, and Hyper vigilance.

The scenario of FIG. 17 will now be analyzed with respect to Instrac components of FIG. 28b. In FIG. 17, a small child (1701) holding the hand of an adult is ambling towards the edge of the road, but the adult is hidden by a pillar (1702). The rest of the text corresponding to FIG. 17 is not repeated here. It is to be noted that not every Instrac component needs to be scored for every scenario, and not every Instrac component will be applicable or available to be scored. Often, some components will be redundant in some scenarios, and some can be a combination of one or more of other Instrac components, with various permutations and combinations available for varying scenarios. In order to have a baseline to which the driver of FIG. 17 can be compared, consider the case wherein a RHD car is driven in this portion of the road by an ideal driver (ID1) in a LHT jurisdiction. ID1 might not score the maximum in each and every Instrac component or path's segment, but scores highest when an overall score is computed.

The sequence of actions by ID1 for FIG. 17 is as follows: The vehicle is being driven by ID1 with only the right hand on the steering wheel. Contact on the steering wheel is mostly from palmar side of the proximal and middle portions (and not distal portions) of the ring, middle and index fingers (and not the pinky or thumb), and the palm excluding the thenar and hypothenar eminences, giving ESCAF=(L[0][0]; R[0.4][0.2]). The foot is depressing the accelerator pedal by 5 mm to maintain a speed of 36 km/hr, so EPO=[5, 0, 0, x]. At 125 m ahead, the child appears in the peripheral vision of ID1. A saccade is then made towards the child, the saccadic latency (time from the onset of the child in the peripheral vision to the initiation of a saccade) being 125 ms, the saccadic duration being 50 ms. A fixation of 125 ms duration occurs on the child, followed by the creation of ROI-child lasting 750 ms, which reveals that that the child might be unaccompanied. The foot starts to release the pressure on the accelerator in 200 ms, and it takes the same time for the right hand to start to gripping the steering a little more tightly, ending with ESCAF=(L[0][0]; R[0.6][0.4]). The vehicle has by now traveled about 13 m (at 36 km/hr). The foot continues removing the pressure off the accelerator pedal (that is, stops pushing down on it) and slowly releases the pedal over the next 5 seconds: EPO(5)=[(5-0), 0, 0, x], during which time the eyes are saccading between ROI-child and the road ahead. The vehicle is now 62 m from the child and traveling at 24 km/hr. The left hand has started gripping the steering, with ESCAF=(L[0.2][0.1]; R[0.6][0.4]). It still appears that the child is unaccompanied. The foot goes 3 mm over the brake pedal, then rests on it but not depressing it, which takes about a second: EPO(1)=[0, x, 0, (3-0)]. Both the left and right hands grip the steering a little more tightly, with ESCAF=(L[0.4][0.2]; R[0.7][0.5]). The vehicle is now about 55 m from the child, who is still inching towards the road. The grip of both hands continues to increase, with ESCAF=(L[0.6] [0.6]; R[0.8][0.6]), while the foot depresses the brake pedal for 2 seconds to bring the speed down to 15 km/hr (EPO(2)=[0, x, 0-3, 0]), and the vehicle is now about 30 m from the child. The eyes are still saccading between the ROI-child and the road ahead. ID1 now sees (through peripheral vision) that an adult is holding the hand of the child and saccades to the adult's face with a saccadic latency of 110 ms, duration 40 ms, fixation 110 ms, and then forming ROI-adult+child, which lasts for 1000 ms. With a time delay of 250 ms, ID1 stops pushing down further on the brake, and starts releasing the brake, while the eye saccades to the road ahead and forms an ROI there. Both the left and right hands reduce their contact area and grip force on the steering, with ESCAF=(L[0.4][0.3]; R[0.7][0.5]), while the vehicle continues to decelerate (slowing due to slight and reducing braking as the pedal is being released, as well as vehicle inertia) to 12 km/hr over the next 2 seconds. The vehicle is now about 20 m from the child, and the foot completely off the brake pedal by 4 mm and about to move over the accelerator pedal: EPO(2)=[0, x, 3-0, 0-4]. Both hands continue reducing their contact area and grip force on the steering, with ESCAF=(L[0.2][0.1]; R[0.6][0.4]). The foot moves over and hovers by 2 mm and steps on the accelerator pedal by 8 mm to bring the vehicle back to 36 km/hr over the next 5 seconds as it crosses the child: EPO(3)[0-8, 3-0, 0, x]. ID1 has released his left hand from the steering, and reduced the grip and contact area of the right hand, with ESCAF=(L[0][0]; R[0.4] [0.2]).

The scenario of FIG. 17 will now be analyzed with respect to Instrac components of FIG. 28b and driven by a test driver TD1, who, by definition, is not as good as ID1. The scenario starts with the car at 36 km/hour, with ESCAF=(L[0][0]; R[0.4][0.3]) and EPO=[5, 0, 0, x]. TD1 peripherally notices an unaccompanied child 100 meters ahead, and his eyes saccade to the child and fixates on it: saccadic latency=140 ms, saccadic duration=50 ms, fixation=150 ms. Formation of ROI-child, lasting 1000 ms, reveals possibly unaccompanied child. TD1 becomes alert. With a time delay of 200 ms, foot releases pressure on the accelerator pedal, hand grip and contact area increases, left hand starts moving towards steering wheel. Left hand then holds steering: ESCAF=(L[0.2][0.2]; R[0.6][0.4]), and, simultaneously, foot goes off accelerator and lands on the brake pedal over 3 seconds: EPO(3)=[(5-0), (0-x), 0, 0]. Meanwhile, the car has traveled 30 m. TD1's eyes are unable to find an accompanying adult. With the child is 70 meters ahead, hand grip increases, brake is depressed by 10 mm for 2 sec to lower the speed from 36 to 18 km/hour: EPO(2)=[0, x, (0-10), 0]; ESCAF=(L[0.4][0.3]; R[0.7][0.5]). The child is now 60 m ahead. TD1 is unable to spot an adult, so car is slowed from 18 to 10 km/hour over 4 seconds: EPO(4)=[0, x, (10-10), 0]; ESCAF=(L[0.5][0.5]; R[0.8][0.6]). The car is now 42 meters from child. The hand grip increases, and the brake is further depressed for 4 seconds (TD1 wants to stop 10 meters from the child): EPO(4)=[0, x, (10-12), 0]; ESCAF=(L[0.7][0.6]; R[0.8][0.7]). However, after these 4 seconds, the car is 30 meters from child at 5 km/hr, and TD1 notices peripherally the adult (holding the child) and saccades to the adult: saccadic latency 120 ms, duration 40 ms, fixation 120 ms, and ROI-adult+child occurs: 1320 ms. It now appears to TD1 that the adult is restraining the child from moving forward. After a delay of 250 ms, the foot releases the brake pedal, and the hand grip reduces: EPO=[0, x, 0, 0]; ESCAF=(L[0.2][0.2]; R[0.4][0.3]). TD1 then accelerates from 5 to 36 km/hour in 3 sec: EPO(3)[20, 0, 0, x]; ESCAF=(L[0.1][0.1]; R[0.4][0.3]).

The performance of TD1 and ID1 in the scenario of FIG. 17 will be analyzed with respect to Instrac components. Starting with State Module 2811, component Lapses 2811e: The child appeared in the peripheral vision of TD1, and his eyes saccaded to the child at 100 m and foveated, forming an ROI around the child. That is, TD1 did not miss noticing the child, and therefore has not suffered any lapses. However, the ideal driver (ID1) noticed the child at 125 m. It is likely that TD1 missed noticing the child at 125 m (at which ID1 noticed). TD1 has suffered a partial lapse, but one that is not very significant, and is given a score of 7/10. ID1's score is 9/10 for this component.

Distraction 2811d: TD1's eyes have been saccading to the ROI-child and the road ahead but not to the child on a bicycle and the lady with a dog (both on the right side of the road in FIG. 17), nor to billboards or mobile phones. This is also borne out by EPO and ESCAF data. Therefore, TD1 is not distracted, and scores 10/10, the same as ID1.

Attention 2811c: TD1 receives perceptual information from the road ahead, which includes traffic on the road, and information from the sides of the road (bicycles, pedestrians, kids, strollers). However, out of this large set of information, TD1 noticed the child 100 m ahead, and then paid focused awareness by forming an ROI around this subset of information. EPO and ESCAF data indicates good agreement with eye movement information and also what actually appears on the road. TD1 scores 10/10 for attention, as also is ID1.

Concentration 2811b: The task at hand is to traverse the segment of the road ahead, while there are distractions on both sides of the road. TD1's saccadic movements do indicate that this is what is being done. When the unaccompanied child is noticed, this becomes an additional key task. TD1 is focused on monitoring the road ahead, while ignoring distractions on the sides of the road. All these are borne out by eye movement and supported by EPO and ESCAF data. TD1 as well as ID1 score 10/10 for concentration.

Vigilance 2811a: TD1 has been on the lookout for unusual situations over the entire course of driving. Similar to ID1, TD1 caught one particular situation. Furthermore, TD1 has been saccading to the road ahead at all times. However, compared to ID1's distance of 125 m, TD1 noticed the child at 100 m, and therefore TD1 scores 9/10 for vigilance, compared to ID1's score of 10/10.

Transaction Module (2812), Information Processing Speed 2812e: This can be inferred from the time between when the child first appeared in the peripheral vision of TD1 to the end-time of the ROI-child, which is a recognition and confirmation of an unaccompanied child in a potentially dangerous position. TD1 took 1340 ms for this operation, while ID1 took 1050 ms. Similarly, the time between when the adult first appeared in the peripheral vision to the end-time of the ROI-adult-child (which is a recognition and confirmation that the child is accompanied and the situation therefore safe) is: ID1: 1260 s, TD1: 1600 ms. From these two time samples, it can be seen that TD1 takes about 27% more time than ID1 to process the same information. Pegging ID1's score at 9/10, TD1 will score 6.6/10 in information processing speed. This is a linear scaling to arrive at the final score in a more forgiving scenario because the road had a low speed limit, and the child was visible over 100 m ahead. If the speed limit were 80 km/hr, or the child was only visible 50 m ahead, TD1 would have scored much lower (4/10, for example), and the same with ID1.

Reaction time 2812: can be extracted from the time that the child was noticed in the peripheral vision to when the foot stopped depressing the accelerator (pressure released, so pedal starts retreating to its normal non-depressed state). This time was 1250 ms for ID1 and 1540 ms TD1, that is, TD1 was 23% slower compared to ID1. Pegging ID1 at 9/10 (that is, assuming ID1 is at the 90 percentile of the population for this component), TD1 scores 7/10. This is a linear reduction of 23%, but in critical cases, can be chosen to be quadratic—for example, if the speed limits were 80 km/hr, and the speeds of ID1 and TD1 were also 80 km/hr.

Sensori-Motor skills 2812c: can be derived from the time TSMS, which is the time from when the ROI-child was first completed to the time when the foot first released pressure from the accelerator pedal (that is, when the pedal starts retreating to its normal 0 position). This value can be incorporated into a quadratic (for example, the quadratic: $y=[a*(TSMS^2)]+[b*(TSMS)]+c$, where y is a unit-less number representing sensori-motor skill level, and a, b, c are constants), or a linear equation, or used raw. If raw numbers used for scaling, both ID1 and TD1 were 200 ms in the initial case, and 250 ms after forming ROI-child-adult. Pegging ID1 at 9/10, TD1 would also score 9/10.

Speed of association 2812b: is the time between when the child first appeared in the peripheral vision of TD1 to the start-time of the saccade to the child, which in this case is the saccadic latency. This represents the speed of association between the concept of a child close to edge of the road and the concept of the child being unaccompanied and therefore potentially darting into the road. ID1's time was 125 ms, while TD1's 140 ms. Pegging ID1 at 90 percentile, TD1 is given a score of 8/10 (about 12 percent lesser than ID1).

Conduct module (2813), hynotization 2813f: There was obviously no hynotization since the eyes had been saccading to various features in the changing scenery, and like ID1, TD1 scores 10/10.

Irritability 2813e was not initially noted because honking or swearing by TD1 at what appears as poor parenting was not picked up by a microphone. However, after confirmation that the child was indeed accompanied by an adult, TD1 pushed down hard on the accelerator, causing TD1 to change speed from 5 to 36 km/hr in 3 seconds, compared to ID1's 12 to 36 km/hr in 5 seconds. This acceleration profile close to the vicinity of the child before crossing the child indicates that TD1 was probably annoyed and angry that the situation occurred and had caused him to slow down unnecessarily. In comparison, ID1 was not easily provoked or impatient. Dangerous driving around a child causes TD1 to score 2/10, compared to ID1's of 9/10, which is computed partly based on a safe stopping distance at the driven speeds.

Impulsiveness (2813d): When the ROI-child indicated an unaccompanied child, neither TD1 nor ID1 slammed on the brakes, but slowed down gradually (the deceleration profile of TD1 being poor compared to ID1 is another matter, and not related to impulsiveness). Both ID1 and TD1 continued looking for an adult without slamming the brakes even after the initial ROI-child indicated lack of adult. Pegging ID1 at 9/10, TD1 also scores 9/10.

Frustration (2813c): was not exhibited since TD1 remained calm and slowed down gradually, while checking the road ahead as well as the ROI-child and approaching cautiously, and the same was the case with ID1. However, there were not enough features and actions to score frustration in this scenario, and therefore neither of them receive a score.

Emotional functioning (2813b): TD1's grip-force and contact area pattern on the steering wheel, as well as the braking pattern, showed reduced emotional functioning as compared to ID1. Pegging ID1 at 9/10, TD1 is given a score of 6/10 because he did not exhibit expected thought and behavior.

Behavior (2813a): From the braking, hand grip and contact area patterns, TD1's conscious response appears adequate compared to ID1 when the child was first noticed. This was also true after the accompanying adult was confirmed to be holding the child's hand, since at both times their response was to change speeds and control the steering wheel better. TD1's conscious response to the situation was what is normally expected—as opposed to being reckless or indifferent by not examining the scene closely or not slowing down. The subconscious response of saccading and forming ROI-child, ROI-child-adult is also considered normal, as also is hovering over the brake pedal. Like ID1, TD1 scores 9/10.

The seventeen Intellect Module (2810) components can be evaluated for this scenario.

Hyper vigilance 2810q: Although both ID1 an TD1 saw the child on a bicycle on the right side of the road in their peripheral vision, neither of them formed an ROI around it. Their reaction was proportional and measured since the child was not an object that was deemed problematic. However, their reaction to the child on the left side of the road, although having similarities in form, was quantitatively different. After the completion of ROI-child and consequent deduction of an unaccompanied child, ID1's ESCAF and EPO values are more gradual than TD1's, as also was the slowing down of ID1's vehicle. ID1 had a proportional and measured arousal and sensitivity to what was determined to be an unaccompanied child. Compared to ID1, TD1's ESCAF and EPO values, as also the slowing down, were excessive and unnecessarily heightened. This caused TD1 slow down excessively, and produce an overall inefficient and less-safe driving profile that reflects hypervigilance. Setting ID1's score at 9/10, TD1 is given a score of 6/10.

Sensitization 2810*p*: It can be seen from the ESCAF and EPO values, as well the speed profile (that varies as the car gets closer to the child) that TD1 was being over-cautious. He reduced the speed to 5 km/hr at 30 meters from the child, even though the child was 1.5 meters from the road. TD1 has probably previously encountered a situation where an unaccompanied child was a couple of meters from the road's edge and started walking towards the road, which might have startled TD1. Having been sensitized, he is now being very cautious, compared to ID1. The latter is scored 5/10, reflecting the possibility that ID1 has not previously encountered an unaccompanied child by the edge of the road. TD1 appears to have experienced this, possibly due to having a much more varied and longer driving experience. TD1 scores 8/10, compared to ID1's 5/10.

Habituation 2810*o*: consider the factors on the road that both ID1 and TD1 ignored: On the right side of the road, there appeared a child on a bicycle, and lady with a dog on a leash. Both the child and the lady (and dog) are far away from the road. ID1 and TD1 have been exposed to this kind of stimuli numerous times before and know there is not much danger associated with it, and have learned to ignore it (and not study it further). That is, both have been habituated. Without habituation, drivers would attempt to analyze each stimuli, handicapping the process of driving, making it inefficient (for example: slowing down) and unsafe for themselves as well as for others. Both ID1 and TD1 score 9/10 for this component.

Cognitive inhibition 2810*n*: There is another child riding a bike on the right side of the road, but neither ID1 nor TD1 have established an ROI around this child, indicating the tuning out of the visual information about this child. There are also other stimuli by the side of the road, but most of them have been tuned out. Both ID1 and TD1 have been saccading between the road ahead and the ROI-child, the road ahead being very relevant to the current task of driving the car. Both ID1 and TD1 score 9/10 for this component.

Anticipation 2810*m*: From saccadic information as well as ESCAF and EPO values, it is clear that both TD1 and ID1 anticipate that the unaccompanied child could dart into the road, and took countermeasures. They did not anticipate this happening with the child on the bicycle. Both ID1 and TD1 score 9/10 for this component.

Flexibility 2810L: Both ID1 and TD1 are faced with competing visual cues, including the child on the bike, the lady walking the dog, and vehicles ahead on the road. However, as soon as the unaccompanied child is seen on the left side of the road, resources were reconfigured to analyze this situation closely. There is a competing demand to keep an eye out on the road ahead while maintaining the ROI-child, which both ID1 and TD1 are able to do. Both ID1 and TD1 score 9/10 for this component.

Planning 2810*k*: TD1's goal is to avoid hitting the child while traversing this part of the road safely and efficiently. After detecting the child in the peripheral vision, such a plan is created: first check out what danger levels are present (is an adult accompanying and in control of the child), and then change speed depending on the outcome of the checking. The associated activities required are to create an ROI-child, release accelerator, apply brakes, increase grip and contact area on the steering wheel to have better control of the vehicle, all the while checking the road ahead. After confirmation that the child is accompanied, the associated activities change to releasing brakes, applying acceleration, reducing grip and contact area on the steering wheel. The plan and general approach to executing this plan is the same for ID1. However, compared to TD1, ID1 planned it better: the slowing of his car was much closer to the child, and the speed slowed down to was much higher. The associated actions of ID1 confirm that this was actually the plan. ID1 is scored 9/10 for this component, while TD1 scores 6/10.

Risk Evaluation 2810*j*: Both drivers had different choices regarding slowing down profiles. From EPO and ESCAF values and speed profiles, it can be seen that TD1's evaluation of risk was poorer than ID1's. TD1 slowed down to 5 km/hr at 30 m from the child, which is a crawling speed given the distance to the child. ID1's speed was 15 km/hr at 30 m from the child. For risk evaluation, ID1 is scored at 9/10, while TD1 scores 6/10.

Resolving 2810*i*: Both ID1 and TD1 set out to resolve the question of whether the child is unaccompanied and therefore poses a danger, and find out correctly when at 30 m from the child. The process included slowing down, gripping the steering better, being ready to depress the brake completely, and making a determination when closer to the child. ID1 is scored 9/10, and so is TD1.

Learning 2810*h*: The potential learning occurring here is that adults accompanying children can be hidden behind other structures. Both ID1 and TD1 have now been exposed to this situation. To find out if learning has occurred, the same scenario is presented again. If TD1 this time around does not drop his speed to 5 km/hr at 30 m from the child, and instead mimics ID1's braking profile, then we can conclude that TD1 has accomplished learning the second time around. Learning is not scored for this segment of the road for TD1. However, in very long segments or paths, such scenarios can repeat themselves more than once, and scoring for learning can be carried out then.

Insight 2810*g*: Both sides of the road have a child. However, ID1 and TD1 understand the inner nature of this situation: the child on the left is very young and probably unaccompanied by an adult, and could possibly dart into the road. The child on the right is well-balanced while riding a bicycle in a straight line, and appears feature-wise older. He is not expected to do anything unusual or dangerous. The younger the child, the greater the danger. Since ID1 and TD1 had this insight, they foveated on the child's features (as part of ROI-child). Both ID1 and TD1 score 9/10 for this Instrac component.

Perception 2810*f*: Sensory stimuli received by TD1 includes images of the road ahead. The visual information (along with vestibular information) detects speed and its changes, features on the road and by the sides of the road. The children on the right and left side of the road, as well as the lady with the dog, appeared as peripheral visual stimuli to the drivers. These stimuli were recognized and correctly interpreted, which is indicated by the fact that only the child on the left had an ROI set up, which feature also happens to be the one that is potentially problem-causing. Since both ID1 and TD1 recognized and correctly interpreted visual stimuli, they both score 9/10 on this segment.

Decisioning 2810e: Upon peripherally noticing the child on the left, TD1 decided to use visual information to solve the problem of not knowing the status of this young child, and therefore the danger involved. There were several options, including stopping the car until the danger passes, coming to a complete stop 10 m from the child, turning around and taking another route, honking so that if an adult is nearby, they would grab the child away from the road's edge, moving to the right-most side of the narrow road. TD1's strategy was to slow down right after confirmation through an ROI-child that the child was unaccompanied or not. This strategy and the response was similar to ID1. However, ID1's implementation was better, and lead to better outcome: faster and safer traversing through the road. ID1 scored 9/10 for this component, while TD1 scored 6/10. The strategy used by TD1 and the different outcomes are not spelled out as inner vocalizations within TD1—these are split-second mental decisions and conclusions.

Reasoning 2810d: The drivers used thought to identify that the child on the left could constitute a danger, while the child on the right does not. ROI-child was formed to evaluate this danger. In Decisioning 2810e discussed above, several possible outcomes were identified, the problem being the maintaining safety by not hitting the child. The drivers used thought to decide on a solution to the problem, which was to slow down and approach cautiously to make the situation clearer. Since the reasoning of both ID1 and TD1 was similar (although the actions following that vary), both score 9/10 for this component.

Judgment 2810c: For both drivers, the initial opinion from the peripheral vision was that there is a child on the side of the road. The evaluation (after forming the ROI-child) was that the child might or might not be accompanied by an adult, followed by, at 30 m, the conclusion that an adult was indeed present. The opinion, evaluation and conclusion was based on visual information, and can be roughly deduced from eye movement, ESCAF and EPO data. Both ID1 and TD1 have the same judgment of the situation, and both score 9/10 for this component.

Thinking 2810b: As a driver traverses this portion of the road, he is mentally processing information from the road ahead. Reducing the concept of a young unaccompanied child to represent danger using the logic that the child could dart into the road, and imagining the subsequent consequences, the drivers address the problem by slowing down, and approaching cautiously to confirm if the child is indeed unaccompanied. All this data is obtainable (and quantifiable) using eye movement, ESCAF and EPO data. Since both ID1 and TD1 performed these functions (albeit with different efficiencies, speed and safety levels), both score 9/10 for this component.

Cognition 2810a: Both drivers sensed the child on the left in their peripheral vision. Their understanding was that this child is very young, and possibly unaccompanied. Using thought, and based on their past experience about gaining a deeper understanding of any situation, they decide to slow down and approach the child cautiously. Eventually, they gain an understanding of the situation (at 30 m from the child). Following this, they also have gained the knowledge that adults can be hidden behind objects, and that children are not unaccompanied in every instance. Cognitively, both ID and TD1 have performed similarly, and have correctly understood the situation. They also have possibly gained knowledge, although this can be confirmed if an identical situation occurs again, and the ESCAF and EPO profiles change such that the transition through this segment of the road is faster. Scoring ID1 at 9/10, TD1 is also scored 9/10.

If a driver suddenly starts looking at the rearview and/or sideview mirrors, then he probably expects to slow down, or stop soon, or switch lanes, or make a turn. Not all of this was considered when Instrac components were discussed above. This was done to keep parameters to a minimum to make the evaluation and discussion shorter and easier.

In an embodiment, driving is divided into two modes. The first mode involves routine driving in a lawful, safe, responsive, defensive, skillful, and knowledgeable manner, and with good conduct and in a good state of driving. In this mode, a subject operating a vehicle does not encounter outside events. However, the subject is still operating the vehicle, and routine aspects of driving will still apply, like driving safely and following the law, and which are called non-events. A list of such aspects of this first mode (non-events) is shown in FIG. 27. In an embodiment, non-events are identified using the scheme of FIG. 26a. In another embodiment, non-events are identified by humans, and in another embodiment, by artificial intelligence programs (AI), and in another embodiment, assisted by databases, all of which can be aided by associated maps and/or data from environmental sensors 2200 (including 2210: outside environment sensors; 2230: vehicle sensors; 2250: human sensors).

The second mode is when a non-routine circumstance occurs. In this mode, drivers detect outside events (henceforth referred to simply as "events") and react appropriately. Such outside events were discussed previously at, for example, FIG. 25 and FIG. 26a, and include outside events related to: danger, children, efficiency, courtesy, special occasions, weather, new traffic situations, unclear situations, being startled, unexpected objects, unexpected actions of others, sudden actions of others, comfort levels, environment, and legal aspects. In an embodiment, outside events are detected using the scheme of FIG. 26B. In other embodiments, outside events are identified by humans, AI, or assisted by databases, all of which can be aided by associated maps and data from environmental sensors 2200 (including 2210: outside environment sensors; 2230: vehicle sensors; 2250: human sensors).

In an embodiment, the first and second modes of driving (events and non-events) can be analyzed and scored. This evaluation can be done by humans or software. Humans can be programmers, local area experts or evaluators who are contributing to writing or developing training software for an AV, or can be expert drivers (EDs) or non-EDs, or those who have been trained to perform such evaluations. Humans can be a single human or a group of humans. The latter can be co-located, or be a group of people not located in proximity, for example, by crowd-sourcing over the internet.

Vehicles can be real (physical) vehicles (real vehicles: RWs) or virtual vehicles (VVs), both of which can also be driven remotely, for example, over the internet. VVs can have the controls, steering, brake and accelerator pedals, and other operational gear as in a real physical vehicle or as in car racing gaming systems or virtual reality (VR) systems. The path can be displayed on a screen, while the rearview and sideview mirrors show appropriately synchronized images. The mirrors can alternatively be on-screen mirrors. The setup can be similar to VR or car racing systems. In an embodiment, the VV system can be a head-mounted system.

Evaluation by software can be carried out using schemes having a database of stored driving scenarios and responses and reactions, or by using an AI system. Software evaluation can also be carried out using other software systems that run autonomous vehicles, or software that runs a VV, or simulation software, and comparing the various driving scenarios and responses and reactions that occur with stored or expected responses and reactions. This, in essence, is autonomous vehicle software evaluation using another piece of software. For example, AV software evaluation software (that is, software used to evaluate other software) mandated or recommended by an administrative agency can be used to evaluate the responses and reactions of a vehicle (RW or VW) driven by a manufacturer's latest software update. Evaluation can be performed in real-time, or the driving recorded and played back for evaluation, or transmitted on-demand (for example, over the internet).

Subjects operating a vehicle can be humans or software systems. These humans or software systems can be on-board the vehicle (in the case of a real vehicle), or operate it remotely (in the case of real or virtual vehicles). Software can include autonomous vehicle software (that is, software that runs an autonomous vehicle), or software that runs a virtual vehicle, or simulation software.

Vehicle operation can be undertaken under various conditions. Conditions can include one or a combination of: time of the day, day of the week, official working day, national holiday, primary schools working day, school summer holidays, national festival days, regional festival days, special events (like ball games, concerts, exhibitions), unexpected celebrations, first rains (slick or slippery roads), minor rain, heavy downpour, fog, condensation, snow, blizzards, low visibility, light levels, traffic levels, pedestrian levels, pedestrian crossings, intersections, merge lanes, levels of children or elderly on road, traffic patterns (smooth flow, bumper to bumper, stop and go), road quality (speed breakers, potholes, surfacing, rumblers), number of lanes, lane widths, divided/undivided road, law enforcement, road gradients, frequently stopping vehicles on road (buses, cabs, garbage pickups), road construction, obstacles on road, lane changes, road locations (extremely crowded city road, central business district, minor congested city road, large town road, small town road, rural road, semi-rural road, highways, divided highways, suburban roads, interstate expressways, and a host of other intermediate types). Conditions also includes the type of vehicle being used for traversing the segment: size, speed, weight, type (passenger, commuter, law-enforcement, emergency, wheels/axles, maintenance) and the vehicle-type mix on the segment being traversed. One or more of these factors can go into a conditions array. For convenience, this array is referred to as just 'conditions'.

Evaluating the quality of a subject operating a vehicle helps in determining and ranking subjects. This can be for very specific instances. For example, multiple subjects operating the same brand and model of vehicle in the same segment of the same path under the same conditions. This evaluation can also be of a more generic nature, with various permutations and combinations of conditions and vehicle types. AVs can be trained to improve their autonomous capabilities by mimicking EDs, who can be chosen from a population of drivers who have been evaluated and ranked. Evaluation can be preformed for one or both of events and non-events.

In an embodiment, EDs drive vehicles (VVs or RWs) around different paths and under different conditions, while data from sensors 2200 (2210, 2230, 2250) is captured and stored. Sensors include video cameras for recording inside the car (eyes of the driver) and outside the car. This saved data from sensors 2210 and 2230 (and not 2250) is made available on-demand for human candidate subjects, for example, over the internet. The driving of these candidates is evaluated against EDs, helping to recruit more drivers as EDs. Such recruitment drives can help scale up the pool of EDs for various paths. This large pool can then drive RWs to help capture more data about the performance of EDs along a particular path, and help AV software mimic such behaviors. Such recruitment can also help provide EDs to drive VVs on paths that have no EDs, and their behaviors mimicked by AV software. Recruiting EDs by evaluation using VVs eliminates issues related to driving risks, hardware costs for equipping vehicles, and the ability to scale up by using EDs from other geographical regions. It also provides the same path driven in the same conditions, which allows for a fair comparison between candidates. Having a large group of EDs in a particular path will help even out extreme reactions, eliminate outliers, while reinforcing desired reactions and capturing missed reactions. When there is a requirement for a seed ED (i.e., there are no EDs), a human or current-model AV can be employed to drive a RW around a path to capture sensor data, and this data provided to several humans for test-driving, which can lead to identifying EDs for that path.

The driving qualities of subjects can be stored in a database, including events and/or non-events. After identification of one or more EDs from amongst the subjects in the database, the response of non-EDs can be compared with EDs. The responses of the EDs can be stored in a separate database, which can be used as, or tested against as, a benchmark for other subjects.

Figure 29A:
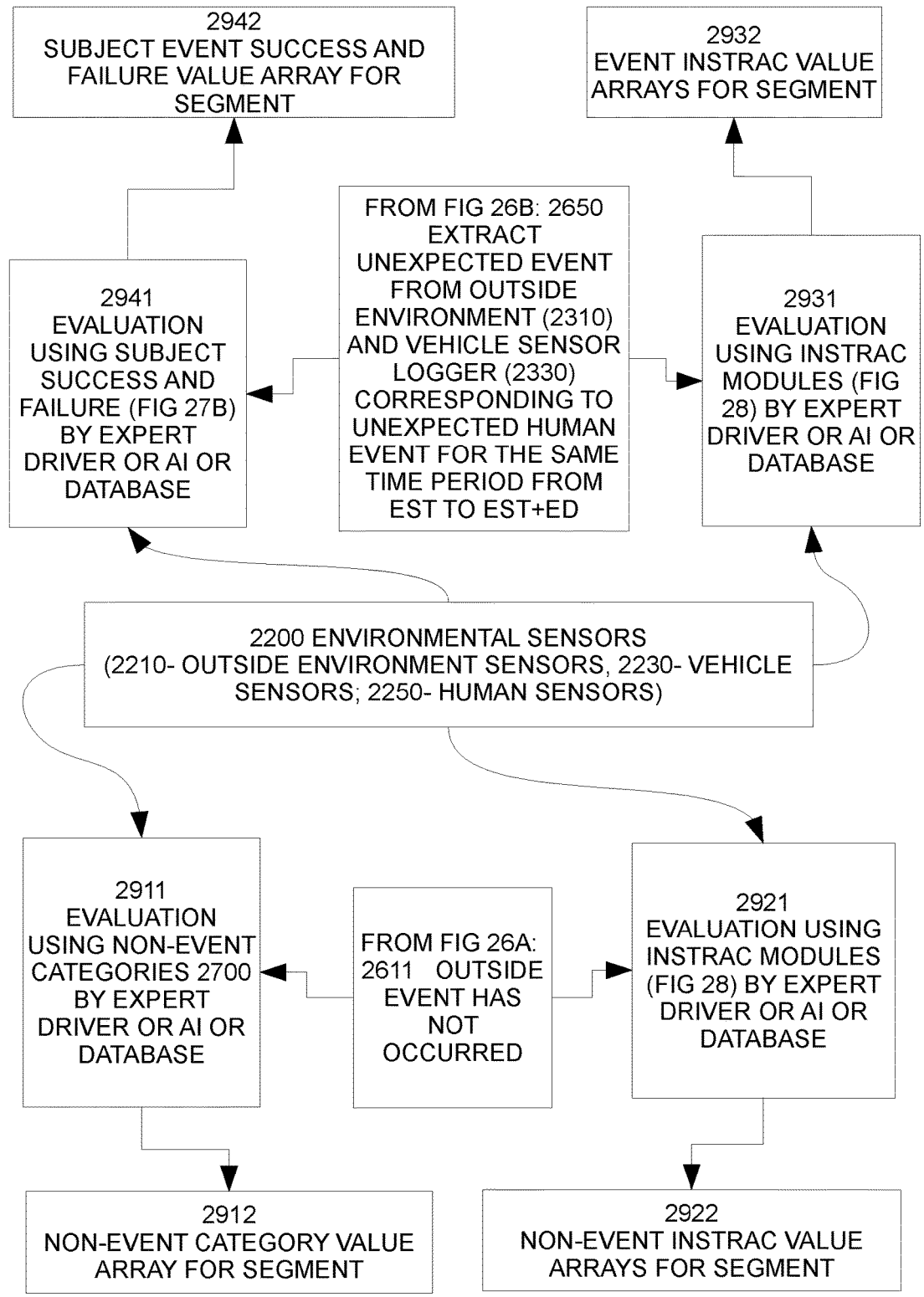
FIG. 29a shows a first scheme for obtaining event and non-event value arrays for a segment.
Figure 29B:
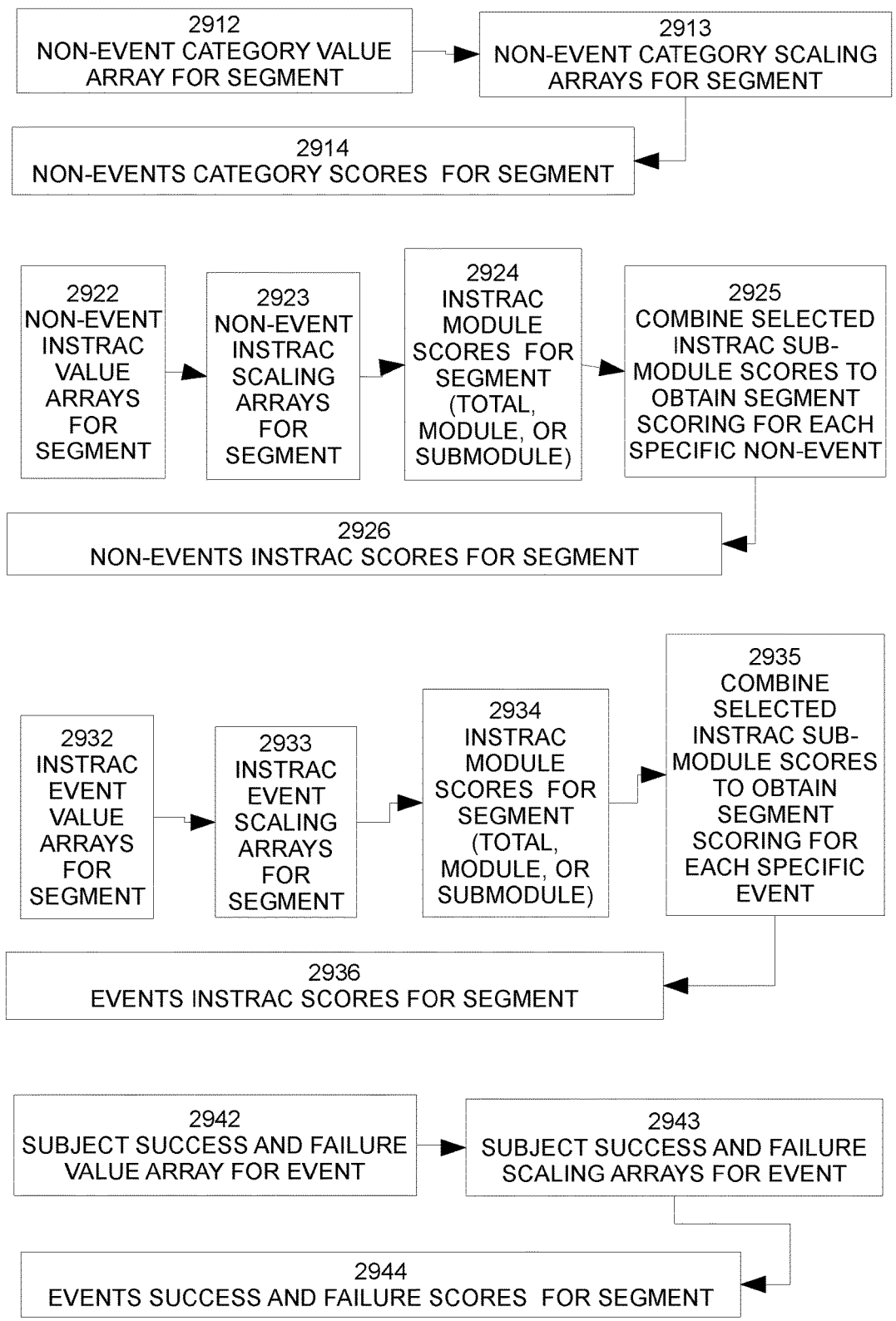
FIG. 29b shows a scheme to arrive at event and non-event scores for a segment using values from FIG. 29a or FIG. 29a1.

FIG. 29a and FIG. 29b show a scheme for the evaluation and scoring of a subject's driving on a segment of a path, accounting for both events and non-events. The schemes of FIG. 26a and FIG. 26b are used to make the determination that an outside event has or has not occurred. FIG. 29a relates to obtaining event value arrays for a segment using data based on FIG. 27b (subject success and failure), FIG. 28 (Instrac modules), and non-event value arrays using FIG. 27 (non-event categories 2700) and FIG. 28 (Instrac modules). FIG. 29b relates to the further processing data from FIG. 29a (and also from FIG. 29a1, discussed later) to provide non-event and event scores for segment after scaling.

The subject operates a vehicle (RV or VV) on a segment of a path. This vehicle has the controls, steering, brake and accelerator pedals as in a RW car, or as in car racing gaming systems or virtual reality (VR) systems. VV paths can be displayed on a screen, while the rearview and sideview mirrors show appropriately synchronized images. The mirrors can alternatively be on-screen mirrors. The setup can be similar to VR or car racing systems. In an embodiment, the VV system can be a head-mounted system. Evaluation can be performed in real-time, or the driving recorded and played back for evaluation, or transmitted in real-time. Evaluation can be performed by a human, including an ED, by using a database of stored driving parameters, by using an AI system, or by crowd-sourcing to a group of people not necessarily located in proximity. The latter can be done over the internet. The subject operating the vehicle can be humans, or autonomous vehicle software based systems (that is, software that runs an autonomous vehicle).

The scheme of FIG. 29a has inputs from 2611 of FIGS. 26a and 2650 from FIG. 26b. If an outside event has not occurred (as in FIG. 26a: 2611), evaluation and scoring of an individual subject's driving on a segment of a path can be performed by one or both of two different methods: using non-event categories 2700, or, using Instrac modules of FIG. 28b. Data from environmental sensors (2200) for the time period [T−ΔT] to T can be evaluated using non-event categories 2700 by passing the values to block 2911, wherein the evaluation is done by EDs, automated systems (database aided), or an AI system. The non-event category value array for the segment is passed on to 2912, while the non-event Instrac value array for the segment is passed on to 2922.

In FIG. 29*a*, if an outside event has occurred (as in FIG. 26*b*: 2650), evaluation and scoring of an individual subject's driving on a segment of a path can be performed in one or both of: using subject success and failure of FIG. 27*b*, or, using Instrac modules of FIG. 28*b*. For outside events evaluation using subject success and failure of FIG. 27*b*, data from environmental sensors (2220) for the time period EST to [EST+EP] is evaluated at 2941 by EDs, automated system (database aided), or an AI system to arrive at a score in the form of an array at 2942. The array is passed to 2943, which contains success and failure scaling array for the segment, and is used to scale the values that come from 2942. The scaled scores for the segment for this period (EST to [EST+EP]) from 2943 are passed to 2944, where the scaled scores for the subject's success and failure on the segment are available. For outside events evaluation using Instrac modules of FIG. 28*b*, data from environmental sensors (2220) for the time period EST to [EST+EP] is evaluated at 2931 by EDs, automated system (database aided), or an AI system to arrive at a score in the form of an array at 2932. The array is passed to 2933, which contains an Instrac scaling array for the segment, and is used to scale the values that come from 2932. The scaled scores for the segment for this period (EST to [EST+EP]) from 2933 are passed to 2934, which calculates Instrac scores as a total, or for each module, or each sub-module, or a combination. Each specific event can have a combination of Instrac modules or sub-modules contributing to the event. This can be user (the person/software/AI conducting the evaluation) defined at any point during the evaluation of the segment or path or condition, or can be universal. Using such a combination can also result in the categorization of the event (as in FIG. 25: categorization of signature, or as can be user-defined), apart from the evaluation.

In FIG. 29*b*, array 2912 is then passed to 2913, which contains non-event category scaling arrays and is used to scale the values that come from 2912. The scaled non-event category scores for the segment for this period ([T−ΔT] to T) from 2913 are passed to 2914.

In FIG. 29*b*, the final modules (2914, 2926, 2936, 2944) are in the plural: events and non-events, indicating that multiple loops have been completed to capture all the ΔTs or EPs in the segment. These final modules will have multiple arrays corresponding to multiple ΔTs or EPs in the segment. In the case of FIG. 29*a*1, ΔT and EP are not used, but the path segment can have zero to multiple events, and zero to multiple time-segments or distance segments, and the final modules (2914, 2926, 2936, 2944) will have corresponding multiple arrays.

Since a segment can have multiple ΔTs or EPs in it (corresponding to multiple events and/or non-events), the process of FIG. 29*a* and FIG. 29*b* is repeated until the segment is completed. In the case of FIG. 29*a*1, since each path segment can have multiple events and/or non-events, the time-segment or distance-segment is repeated until the segment is completed.

FIG. 29*a*1 shows an embodiment in which the determination of whether events and non-events (that is, end of an event, with no other event starting immediately after this end) have occurred is made by one of humans, AI, or aided by databases, or a combination, all of which can be aided by associated maps and/or data from environmental sensors 2200 (including 2210: outside environment sensors; 2230: vehicle sensors; 2250: human sensors). This embodiment does not use the detection mechanism of FIG. 26*a* or FIG. 26*b*, and is distinct from the embodiment of FIG. 29*a*. Human(s) make determinations based on their driving and life experiences, and need not necessarily be EDs. If needed, the human(s) can also be provided with instructions, training or guidelines as to what can constitute such events and non-events. Similarly, an AI system can be trained to make such determinations. Databases of previous events and non-events can also be used in this determination. Such databases or AI system aid a computer based program that also has inputs from environmental sensors 2200. It will be evident that various combinations of these three (humans, AI, databases) can also be used to make the determinations. FIG. 29*b* is common to both FIG. 29*a* and FIG. 29*a*1.

In this disclosure, when the scheme of FIG. 29*a*1 is used, the road being traversed is divided into discrete time-segments or distance-segments. Scoring of subjects for each time or distance-segment is carried out in the case of non-events. In the case of events, scoring is for the event and not for the time or distance segment. Data from environmental sensors (2200) is being continuously passed to 2911, while the human, AI or database system make a determination if an outside event has occurred and is still continuing, and when this event ends and is followed by another event or non-event. Data provided by the environmental sensors (2200) includes: speed profile of the vehicle, road facing camera video, video of the driver's eyes/head, braking data, turn-indicators, visibility etc. When humans are performing the determinations and evaluations, time-segments or distance-segments can be chosen to be high, for example, 1-10 seconds, or even in the minutes range for driving on monotonous roads. However, if a pause or time-stretch (slow playback) feature is available, then this need not be the case.

In an embodiment, scoring of an individual subject's driving on a segment of a path for non-events (after determination in 2611 of FIG. 26*a*) is carried out using Instrac modules of FIG. 28*b*. Data from environmental sensors (2220) for the time period [T−ΔT] to T is evaluated at 2921 by EDs, automated system (database aided), or an AI system to arrive at a score in the form of an array at 2922. The array is passed to 2923, which contains non-event Instrac scaling array, which is used to scale the values that come from 2922. The scaled non-event category scores for the segment for this period ([T−ΔT] to T) from 2923 are passed to 2924, where the scores are fit into each sub-module of Instrac—allowing evaluation based on sub-module score, module score, or total score, or any combination thereof.

Figure 30A:
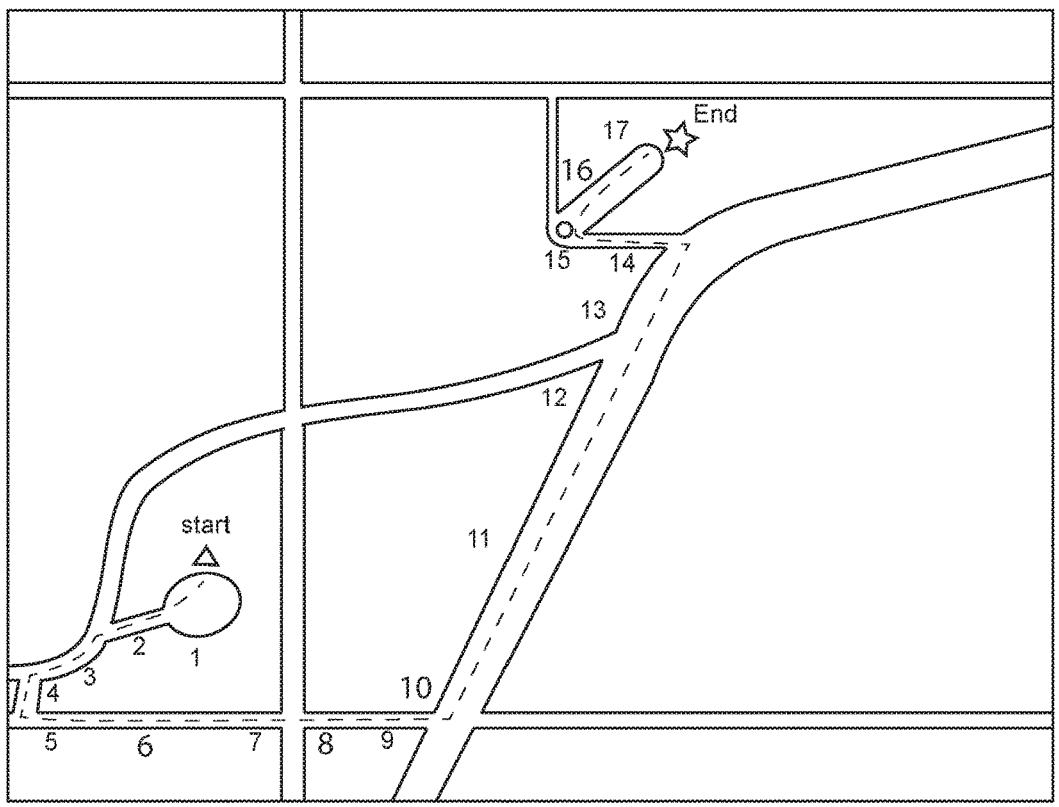
FIGS. 30a, 30b show sample paths broken down into segments.
Figure 30B:
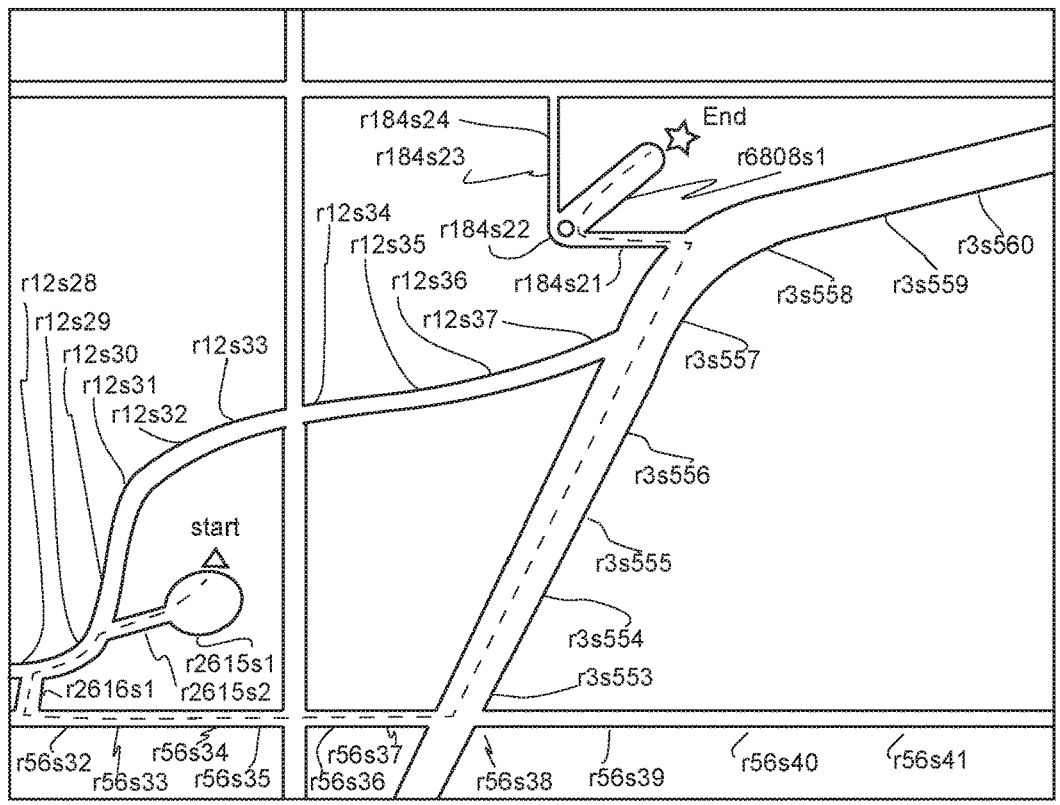

FIG. 30*a* and FIG. 30*b* show sample paths with multiple segments within them, and illustrate one of the many methods to break down a path into segments. The path starts at point marked with a triangle and "Start", and ends at the point marked with a star and "End". There are several possible routes a subject can take get from start to end. FIG. 30*a* shows one such path, with segments numbered sequentially from 1 to 17. The segment numbering is specific to this particular path between these two specific points. The path is defined as P1[SG1, SG2, . . . SG17].

FIG. 30*b* shows the same path as in FIG. 30*a*, but with a different scheme for segment numbering. Here, roads are broken down into segments. For example, r12s33 refers to the segment 33 of road 12. The path shown by a dotted line is P1[r2615s1, r2615s2, r12s29, s9r2616s1, r56s32, r56s33, r56s34, r56s35, r56s36, r56s37, r3s553, r3s554, r3s555, r3s556, r3s557, r184s21, r184s22, r6808s1], which is the same path (and therefore consists of the same segments)

shown in FIG. 30a. There are several more alternate paths (not shown in FIG. 30b) to get between "Start" and "End", an example being: P2[r2615s1, r2615s2, r12s30, r12s31, r12s32, r12s33, r12s34, r12s35, r12s36, r12s37, r3s557, r184s21, r184s22, r6808s1]. Opposite directions of a segment in a road can, if necessary, be named differently. For example, the portion r2765s55 can have two segments going in opposite directions: r2765s55ne and r2765s55sw, "ne" standing for north-east, "sw" standing for south-west. These two segments can have different scaling factors and other characteristics, and so can multiple lanes in the same direction.

FIG. 30c shows data arrays used to score and rank subjects. Operators of vehicles are referred to as subjects, and can be human or AV operating software. A path is made up of one or more segments. There can be one or more Subjects. Vehicles can be operated under different conditions. Path 1 of the Path and Segment array (3000) has one or more segments, which are denoted: Path 1, Segment 1; Path 1, Segment 2; and so on, until Path 1, Segment SGN. Similarly, Subject Array (3025) has one or more subjects denoted: Subject 1, Subject 2, and so on, until Subject SN. Condition Array (3050) has one or more conditions denoted: Condition 1, Condition 2, and so on, until Condition CN.

FIG. 30d shows scaling factors associated with the arrays of FIG. 30c. Subjects are scored according to the paths driven and conditions under which driven. Scores are computed by taking scaling factors into account. Each segment of each path has an associated scaling factor, and so do each subject and each condition under which the vehicle is being operated. These scaling factors can be chosen by the subject operating the vehicle, or by the software (AV software operating the vehicle or AI). They can also be chosen by other humans, for example, programmers or local area experts who are contributing to writing or developing training software for an AV. Scaling can also be automatically determined and applied when using a swarm of subjects, or one or more EDs. Scaling factors can be dynamic in the sense that they can be dynamically auto-tuned, or change with the time of day and day of week (for example, to account for working days, school holidays). Scaling factors can be extracted from software tracking a vehicle's operation, for example, in conjunction with other factors like weather and special events.

Assigning of scaling factors can be performed automatically by the vehicle's software depending on its current or historical experiences, or the current or historical experiences of its cohort. Cohort vehicles are those plying in the same or similar geographical region, or under the same or similar conditions, or the same or similar types of vehicles.

As an example, consider a path from the suburban home of a subject to his place of work in the central business district (CBD). The path has several segments, including: segment from the house to the minor road that connects to the major road in that suburb, segment from the minor to the major road, segment from this major road to highway that connects to the city, exit road segment connecting the particular part of the CBD with the highway, and so on. These segments can be broken down into smaller segments or combined into larger segments. Segments can be of any size, for example, a 25 meter stretch before a pedestrian crossing, a 50 m stretch between two other roads, or a 100 m stretch before a traffic light, or several kilometers in the case of some highways in the Australian outback. One road can be subdivided into multiple segments depending on traffic patterns, width of road, divided/undivided portions, multi-lane portions, inside suburb or inside city, school zone, pedestrian crossing zone etc. These small segments will be traversed in different modes (including different speed or speed profiles) because of their sizes, legal speed limits, presence of schools, day of the week, quality of road, weather, roundabouts, time of the day etc.

Although the segment scaling factor has been assigned a single value above, it can also be an array. This array can hold several values. For example, consider segment SG23 of path 8: SGN23PN8 and its scaling factor SF(SGN23PN8)= [RT=16, SL=60, TD=18.35, DW=2, DN=288, SV=33, STL=4, OL=12, SSH=3, SSV=1], where RT is the type of road (4 lane undivided road in this case), SL is speed limit, TD is time of day, DW is day of week, DN is day number (1 to 365), SV is segment visibility level (ability to have a clear view of the road ahead), STL is segment traffic level, OL is obstruction level (obstructions on road that impede driving-including speed bumps, potholes, road surface quality), SSH is segment safety human (likelihood of humans entering the road at unauthorized points), SSV is segment safety vehicles (likelihood of vehicles, including bicycles, entering the road at unauthorized points).

Figure 31:
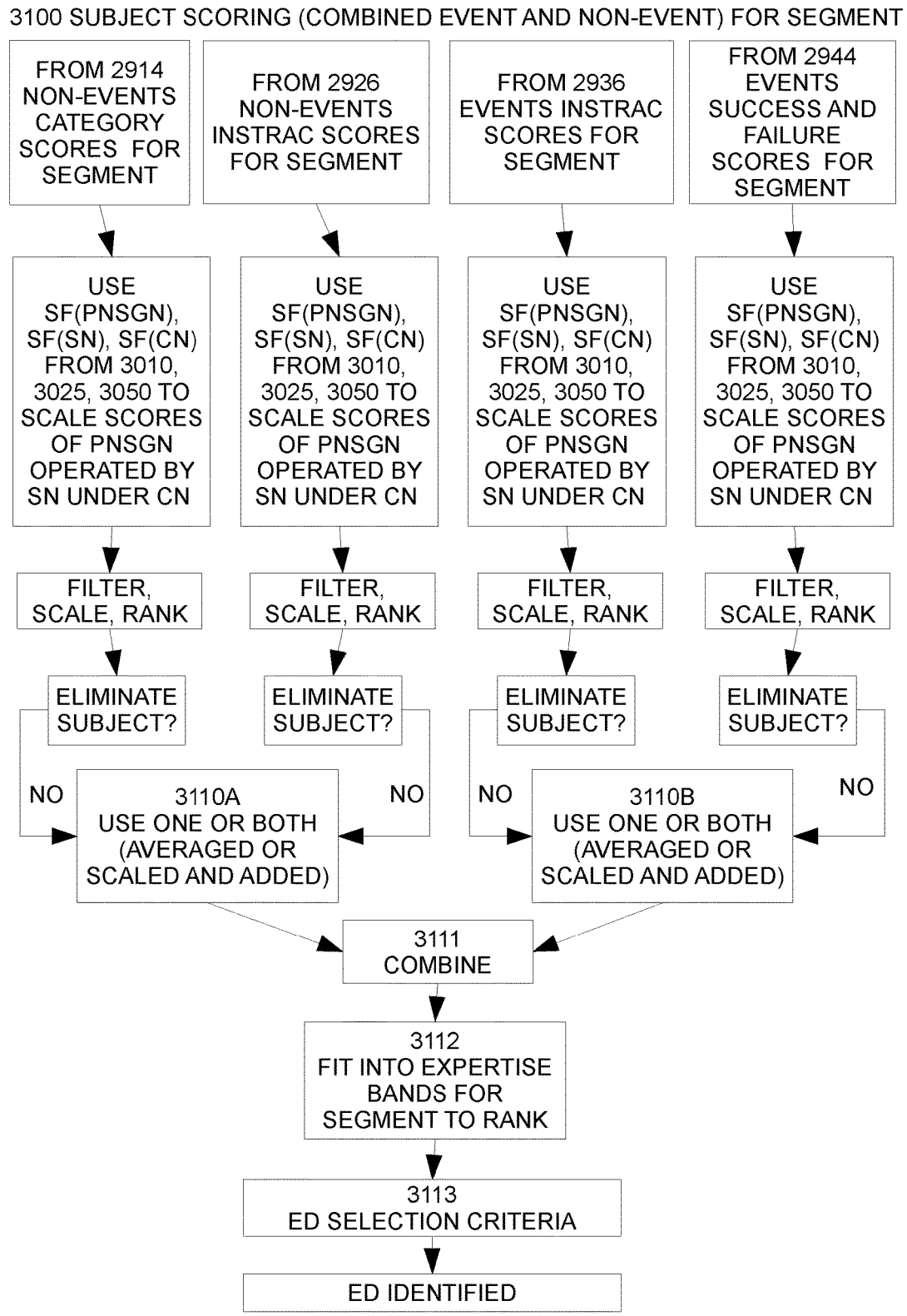
FIG. 31 shows a scheme to score a subject operating a vehicle on a segment of a path under a specific condition.

FIG. 31 shows a scheme to score a subject (from 3025: SN) operating a vehicle on a segment of a path (from 3000: PNSGN) under a specific condition (from 3050: CN), which filters, scales and ranks scores to identify EDs for this segment under this condition. Scores from 2914, 2926, 2936, 2944 for a particular subject (from 3025: SN) operating a vehicle on a particular segment of a particular path (from 3000: PNSGN) under a particular condition (from 3050: CN) are scaled using SF(PNSGN), SF(SN), SF(CN) from 3010a, 3025a, 3050a. It should be noted that either one or both from each of 2914, 2926 (non-events) and 2936, 2944 (events) can be used for ED identification.

A decision is made to eliminate the subject if the subject is under-performing compared to his peer group or a threshold score. For example, if the driver has caused a severe accident causing loss of life, or has very poor attention, or is very distracted, then he is eliminated. The threshold can be hard-coded, or set by the scoring system dynamically, or set by the user/administrator, this setting being based on criteria being fulfilled. For example, subjects scoring in the lowest 10% can be eliminated, or only the top quartile can be retained, and the rest eliminated. This can also be done in real-time and automatically, without the need for a human to input the value. The threshold can vary from segment to segment, and can also be changed to accommodate specific situations (like a pile-up due to snow, black-ice, special events like a ballgame taking place in the vicinity). The threshold can vary between a practice mode to test out and become familiar with the VR system, and an operating mode of the VR system, or intermediate modes, including modes where threshold changes after a few trial runs.

FIG. 31 also incorporates filters that can be applied to eliminate, promote or re-order the subject in a rank. The filters can be arrays. As an example, the array can consist of driver responses to school-zones and children on the road. Consider the case of a school-zone with a speed-limit of 40 km/hour. Some drivers might stay at 39 km/hour, some drive at 41 km/hour. It might not be desirable to eliminate the driver going at 41 km/hour, although he has to be penalized. The penalization can be an array consisting of excess speed over limit and corresponding penalization values. However, if the same driver took much longer to slow down than the average of his cohort when an unaccompanied child was at the edge of the road, this behavior combined with being slightly over the speed limit in a school zone might indicate a general disregard for child-safety. The two factors (a list of excess speeds, and a list of speeds close to the child) can be stored in a look-up table, or a linear or non-linear formula can be used to arrive at a penalization factor or value. In other instances, the filter can include promotion arrays, where specific actions in a particular segment are appreciated more than in other segments. For example, the same penalization scenario can be set as a promotion array when subjects have responded appropriately to events. For the same category of events, this promotion array values can vary from one segment to another, for example, higher promotion values in crowded single lane roads compared to multi-lane roads in suburbs. In the case of non-events, filters can be applied to eliminate, promote or re-order the subject in a rank. For example, a particular manufacturer of a AV training system might decide to classify a subject with poor State 2704 (<−5 on all portions) while traversing multiple segments as a non-ideal candidate, and therefore be eliminated. Another manufacturer developing AV training systems for AVs specialized for desert driving (as in Arizona or the Australian outback) might decide to promote drivers who are lawful 2701 (>+5 on at least 90% of measured segments), but reduce dependence on other non-event categories unless any of them are very low (<−5, for example) by ignoring them from the ranking scheme for most segments other than predetermined or critical ones (like segments passing close to towns). In another example, an AV training package developer concentrating on congested city driving can give more weightage to knowledge (2708), skill (2706) and safety (2702), while reducing weightage for lawfulness (2701), responsiveness (2703), state (2704), defensive (2705) and conduct (2707).

If the subject is not eliminated, then at 3110*a* and 3110*b*, the scaled scores for each pair of non-events (2914, 2926) and events (2936, 2944) are used separately or in combination with the other in the pair. They can be averaged, or scaled and added if used as a combination, at 3110*a* and 3110*b*. It is to be noted that all these scores are arrays. The scores are then filtered and scaled if necessary, before being combined. Such a scaling can be used to adjust relative weightage in the total score computation, this scaling having a value of between 0 to 1. For example, if non-events are not being used in score computation, then a zero scaling factor can be used, or a factor of 0.25 can be used for reducing the weightage of non-events. At 3112, this score is then compared to the other scores of a population for this same segment, fitting it into the band of scares to see the rank in the population. At 3113, the score is compared to a threshold. If the score is high enough to cross this threshold for determining if the subject is an expert driver for this segment, then an expert driver has been identified at 3114. The threshold can be selected by a human, or can be assigned automatically. For example, the threshold can be set as being scores above 90% of the population in the segment. It can also be set to be dependent on the population. For example, if the population in the segment is below 100, the threshold can be set such that everyone exceeds the threshold. In another variation, the threshold can be set so that the subject crosses it as long as there are no other failures (in other segments). It can also be set so that a running average of scores for all past segments is used as a threshold.

Figure 32:
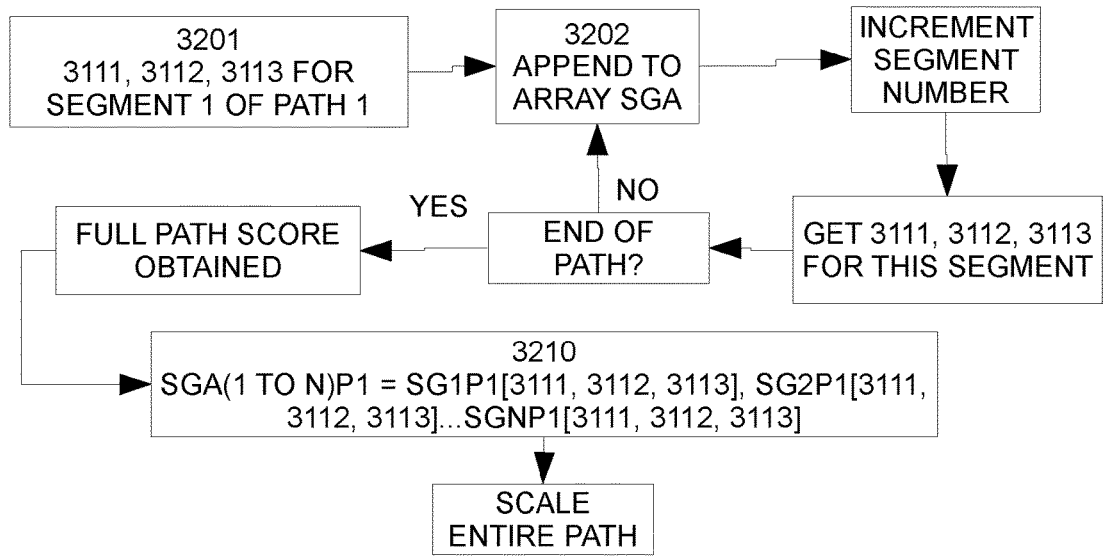
FIG. 32 shows a scheme to use segment data to obtain the total score for an entire path.

FIG. 32 shows a scheme to use the data (event as well as non-event) acquired for individual segments in a path to obtain the total scores for the entire path. The path is traversed by the same subject and under the same conditions for each segment. Scores from 3111, 3112, 3113 are used for this purpose. At 3201, the subject traverses segment 1 in path 1. Scorers 3111 from FIG. 31 corresponding to this segment, as well as the ranking 3112 for this segment and ED selection criteria 3113, are accumulated in an array SGA at 3202. This is continued until all the segments in the path are traversed, as in 3210. Array SGA will then hold values SG1P1[3111, 3112, 3113], SG2P1[3111, 3112, 3113], to SGN, PN[3111, 3112, 3113], wherein each set [3111, 3112, 3113] corresponds to each segment. When the scores for the entire path are required as a single score, individual raw 3111 scores can be added. To obtain average ranking for all the segments in the path, ranks from 3112 can be added and averaged by the number of segments in the path. Similarly, to obtain raw ED cutoff scores, each 3113 can be added, and division by the number of segments will provide the average ED cutoff score for this path. Alternate methods of computing path scores, ranks and cutoffs from individual segment scores can include obtaining root mean square values, median values, using just a single or range of maximum value(s) or minimum value(s), or using other statistical methods. Array SGA can be scaled if necessary.

Figure 33:
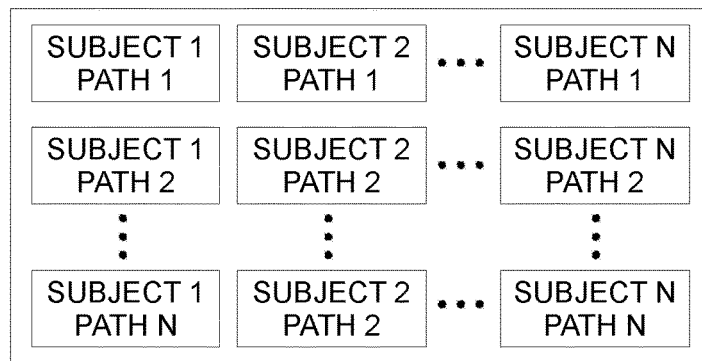
FIG. 33 shows an array that stores scores of multiple subjects on multiple paths under the same conditions.

FIG. 33 shows an array that stores the scores of multiple subjects on multiple paths under the same conditions. While FIG. 32 relates to the same subject traversing the segments in a path under the same conditions, FIG. 33 is a super-set of FIG. 32. There are a multiplicity of subjects and paths in FIG. 33, wherein each subject traverses each path. Since these paths can have different relative difficulties, importance or criticality, they can each be scaled when necessary. When the scores for the multiple paths traversed by the same subject are required as a single score, individual path scores (as obtained in FIG. 32) can be added. To obtain average ranking for all the paths, ranks for each path (obtained from FIG. 32) can be added and averaged by the number of paths. Similarly, to obtain averaged ED cutoff scores for all the paths, ED cutoff scores for all the paths can be averaged. Alternate methods of computing scores for multiple paths, ranks and cutoffs from individual paths scores can include obtaining root mean square values, median values, using just a single or a range of maximum value(s) or minimum value(s), or using other statistical methods. The end result of FIG. 33 is a multi-dimensional array of multi-path, multi-subject scores, ED cutoff scores and ranking.

Figure 34:
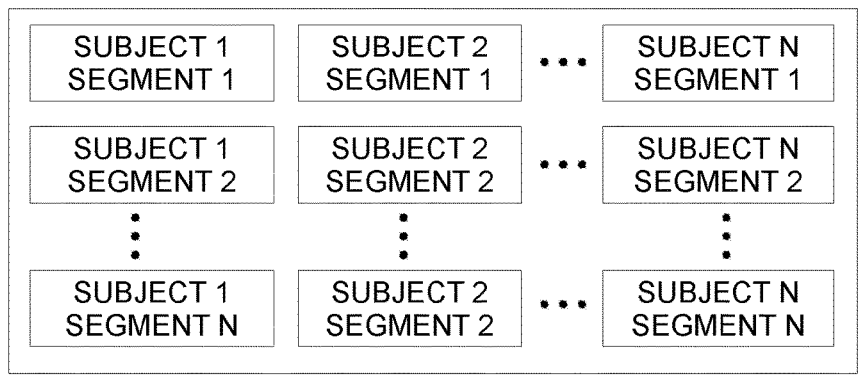
FIG. 34 shows a subset of FIG. 33 with only segment values.

FIG. 34 is a subset of FIG. 33. In FIG. 34, instead of storing path values, only segment values are stored. Path information is not necessary to create this array.

Figure 35:
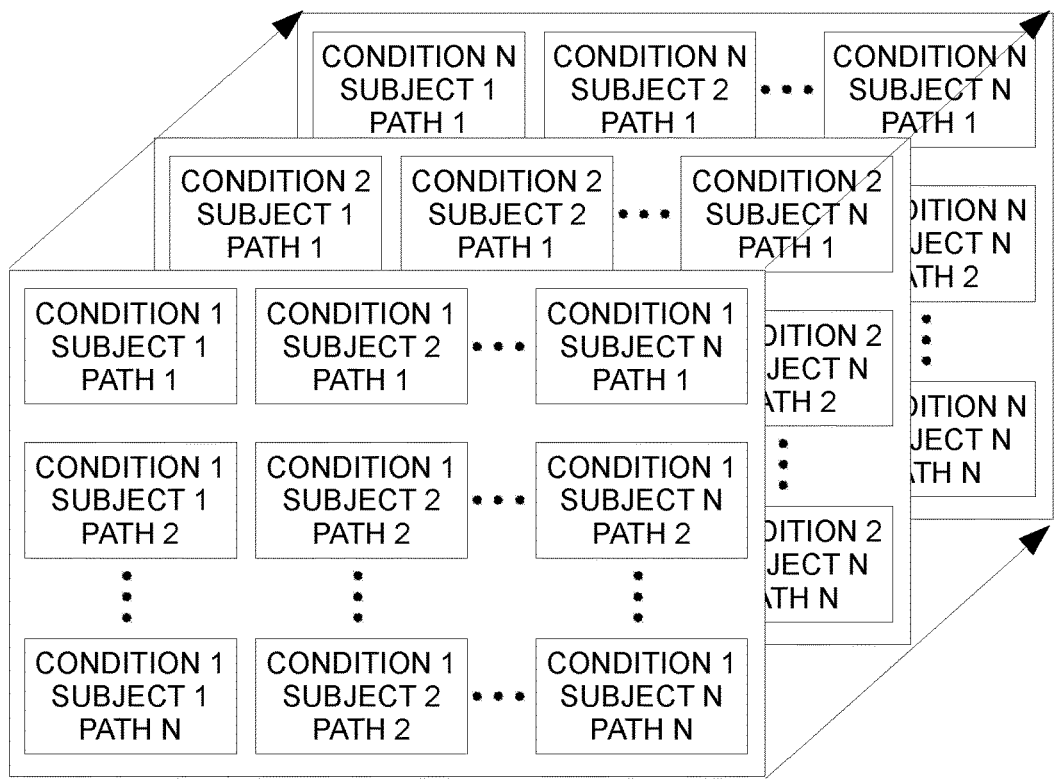
FIG. 35 shows a super-set of FIG. 33 with different conditions for all segments.

FIG. 35 is a super-set of FIG. 33. In FIG. 33, the conditions for all segments of all paths were either unchanged or not recorded. Consider two identical vehicles being operated in proximity (side by side or behind one another) along the same segment. The conditions are almost identical for both the vehicles. If the vehicles are operated at different times, the conditions might naturally be different for each—different traffic pattern, different visibility, different pedestrian patterns, and so on. If conditions are to be accounted for, and given at least some weightage, then these conditions need to be incorporated into the arrays of FIG. 33. This is shown in FIG. 35 as a multi-Subject, multi-Path, multi-Condition 3-D array containing the subject number, path number, condition number, and scaled scores, ranks, ED cutoffs for each of the combination [S1, P1, C1] to [SN, PN, CN]. Similar to the case in FIG. 32, methods of computing scores, ranks and cutoffs across multiple paths with constant conditions, or multiple paths with varying conditions, can include obtaining mean values, root mean square values, median values, using just a single or range of maximum value(s) or minimum value(s), or using other statistical methods.

Figure 36:
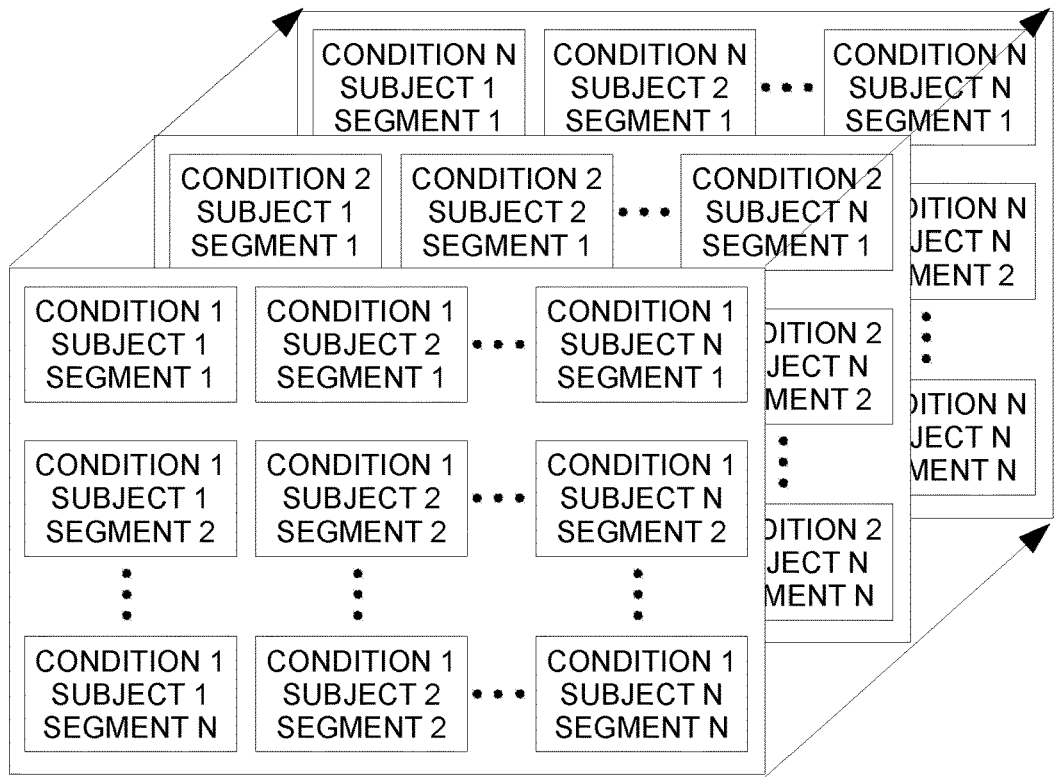
FIG. 36 shows a subset of FIG. 35 with only segment values.

FIG. 36 is a subset of FIG. 35. In FIG. 36, instead of storing path values, only segment values are stored. Path information is not necessary to create this array. Segments are uniquely identified, and can therefore exist without a corresponding path number. That is, no two segments, irrespective of which path they are in, have the same segment number.

In an embodiment, virtual worlds (VW) are provided as segments and paths. VWs are software generated, and therefore different from recordings of real-world traversed paths, as obtained from, for example, recordings by a road-facing smartphone or dash/roof mounted camera (called Camera Worlds—CWs) that can be played back for humans or AV software to traverse. These VWs can be traversed by virtual vehicles (VV) operated by humans or by AV software. In the case of VVs being operated on VWs, paths can be traversed at a fraction of the time compared to: (a) humans or AV software operating real vehicles (RV) in real worlds (RWs), or (b) humans operating VVs in RWs or VWs. This allows AV software to be tested over millions of miles in a very short time, for example, in a few days. This speeding up can be done, for example, by speeding up the CPU clock frequencies of the VW, VV and AV software, or by parallel processing, or by distributed processing, or by skipping non-events, or by skipping segments with only non-events, or by skipping segments/paths with very few non-events compared to events, or by concentrating on segments where the average events scores of a population is very low, or by using the average subject failure scoring (2801) of a population in a segment/path, or by using the average subject success scoring (2802) of a population a segment/path, or by a combination of any of the preceding. The foregoing can also be used for speeding up traversal in the case of RVs operated by AV software or humans, or human operated VVs—without processing adjustments (clock frequencies, parallel/distributed processing).

Arrays of FIG. 33, FIG. 34, FIG. 35, FIG. 36 can be put to use in a variety of others ways. For instance, they can be used to test newly developed AV software. In an embodiment, before the release of a particular brand or version/revision of AV software to the general populace, AVs are required to pass driving tests on several paths under different conditions. The paths are centered around a geographical region. For example, the path can be centered around a small region, and include paths in the central business district (CBD), inner city neighborhoods, outer suburbs, semi-rural areas beyond that, and rural areas beyond that, followed by areas without settlements or that are very sparsely populated. EDs are selected from the same geographical regions, or regions that are similar in terms of traffic laws, infrastructure, demographics, population, and patterns of driving. EDs of CBD may not necessarily be EDs of sparsely populated areas. Each segment of a path can have a different ED. In order to train an AV that has the best performance in every segment of every path, segment specific EDs are utilized. The responses and driving patterns of the AV is compared to that of the EDs, and required improvements or changes are are made to the AV software. This is done in several stages before releasing the new AV software driven vehicle on public roads. Pre-alpha, alpha, and beta releases are first tested. This is followed by release candidate testing in multiple cities, and then single city release for the general public, followed by national release.

An embodiment of release stages follows. However, it should be noted that there can be other variations to how AV software is released. In the pre-alpha stage, the AV software is modified and adapted to drive VVs in VWs. Many of the traditional sensors like LIDAR, radar and ultrasonic will not be of use in this mode. The AV software as well as EDs are scored to finally arrive at the matrices of FIG. 35 or FIG. 36. Pass/fail criteria are set for each segment for the AV software, as well as a total score criteria. The AV software can be tweaked, trained, or re-written to mimic EDs in segments where it failed. This process is then repeated in the alpha stage (in multiple iterations if necessary), where a VV is operated in a CW. This is followed by operating RVs in RWs during the beta stage, where LIDAR, radar and other sensors (that were not used in VVs/VWs/CWs) can be used. The beta stage can be in non-public test areas to begin with, and then later transitioned to public roads. After the beta stage tweaking, release candidates are tested in multiple cities, and then single city release for the general public, followed by national release. To avoid modifications and adaptions of AV software to run VVs or VWs or CWs, or if there is a need to test all sensors (including LIDAR and radar) from the very beginning, then pre-alpha and alpha stages can be discarded with. During all the prior-mentioned stages, hardware adjustments can also be made to change or enhance performance. For example, an instruction can be added to increase the scanning cone angle of LIDARs to detect features on sidewalks that are not captured due to obstructions, where these features appear only when the vehicle is very close to the feature. As another example, an instruction to zoom-in video cameras to capture the faces of what appear to be children, so that software extraction of age ranges can be carried out, as well as analysis of whether the child is accompanied (by slight zooming out to see if an adult is in control of the child).

In an embodiment, preset standards can be stored as a regulatory ED in the arrays of FIG. 32, FIG. 33, FIG. 34, or FIG. 35. These standards are government or regulatory/standards agency benchmarks. Newly released AV software (or the tweaked versions) or even existing AV software can then be tested against the driving of the regulatory ED. This can be done using RVs or VVs on VW, CW or RW segments and paths as needed.

In an embodiment, preset standards can be stored as a safety ED in the arrays of FIG. 32, FIG. 33, FIG. 34, or FIG. 35. These safety values, benchmarks or behaviors are government or industry minimum, ignoring which can potentially cause accidents. When AVs approach these values, alerts can be issued to the occupants of the vehicles, and a central/nodal agency can also be notified. Safety mechanisms can be installed in AVs so that exceeding these values can cause the vehicles to be automatically slowed and parked at a safe point, awaiting arrival of emergency or law enforcement personnel, or relief vehicles.

In an embodiment, ESCAF, EPO and EMD of vehicle operators (particularly those of EDs) while they traverse segments/paths using RVs in RWs, or VVs in CWs or VWs under various conditions are stored as arrays into the Subject arrays of FIG. 33, 34, 35, 36, as also are event signatures (2501-2515). This data can be used in a variety of ways. For instance, ESCAF, EPO and EPD of new human drivers can be captured and compared in real-time. Corrective feedback (for example, in the form of a voice "watch out on the left and be prepared to stop if necessary", "you did not look at the sideview mirror before entering this lane", "you looked at the sideview mirror but did not check your blind spot before entering this lane", "looks like you did not notice the speed limit sign on the left", "you appear distracted by events on the sidewalk") can be given to the new driver when there are major deviations from that of EDs for any geolocation range. Motivational and congratulatory messages can also be provided. In another embodiment, this system can be used to provide alert messages to experienced drivers. Example messages can include: "road ahead requires careful scanning for pedestrians", "better to switch to the right lane now", "bicyclists can appear suddenly on this stretch", "watch out for ambulances over the next 200 meters", "kangaroos usually along this road at this time", "don't get startled by the large dog rushing in towards the fence on the left", "school zone, kids might dart into the road for the next 300 meters at this time". Messages can be based on a variety of factor, including averages of 2501-2515 of several drivers, or only of the top 10% of EDs.

From the preceding discussion, it can be seen that the AV training system and method, as well as the driver scoring and ED identification system and method can be used in any situation where a human is operating any type of vehicle, be it a land vehicle, air vehicle, space vehicle or water vehicle—as long as the vehicle has controls that are actuated by human limbs, and vision and/or sound is part of the sensing mechanisms for this closed loop control.

FIG. 37 shows an example of how an ED identification scheme can be used by a company to develop a platform to facilitate improving autonomous vehicle software. Human candidates wanting to participate can sign up online with the company, and download an app onto their phone from an app store. There are five categories in this app: C1, C2, C3, C4, C5. The app can be used in conjunction with virtual vehicles (VV), real vehicles (RV), real world (RW) paths, camera world (CW) paths, and virtual world (VW) paths. FIG. 37 shows a table listing the categories, and for each category: the types of vehicles that can be driven, type of eye movement sensor used, presence or absence of aural and foot and hand sensors. Eye movement sensors can be smartphone cameras ('P') or dedicated cameras ('C') mounted facing the eye of the subject. The vehicles can further be augmented with aural ('?' means optional), foot and hand sensors depending on the category. All real vehicles have road-facing cameras to capture the video of the path as it is traversed. Many of these categories will help eliminate those with anatomical or physiological defects (for example: Parkinson's disease, nystagmus etc that affect saccades or saccadic intrusions) and those who are under the influence of substances (like alcohol, medication).

In C1, which is a very basic level, candidates are required to have a smartphone with a front (selfie) and rear facing camera, GPS, and microphone, or a VR system with at least one camera to capture eye movements, or a computer with a monitor and a camera. There are no foot or hand sensors in this category. The camera (of the phone or VR system or desktop/laptop computer) serves as the eye movement sensor (2251). Optionally, the camera's microphone(s) can be used as an aural sensor (2254). The phone is positioned on a stand similar to 1201*b* in FIG. 12*a*, with its screen facing the driver. The screen has illuminator patterns 1207*b*, 1207*c* as in FIG. 12*f*, or external LEDs can be used in addition to or instead of illuminator patterns. The GPS of the phone is always on. The app allows calibration of the eye movement tracker, hand sensors and foot sensors (calibration of these has been described previously), which can be at startup or anytime after. The app starts gathering data from sensor set 2200 when the candidate starts driving (for example: by detecting changing GPS coordinates that corresponds to driving, or the starting of the engine, or a manual input, or using the phone's IMU). Camera(s) capture the driver's eye movements, which are stored along with the GPS data and timestamps. This stored data is uploaded onto a central server of the company whenever there is an internet connection available (or as setup by the driver on the phone's preferences). Multiple such paths are uploaded over the course of time (days, weeks or months). This data on the central server is served to trained evaluators, EDs, AI systems or databases for ranking the driver for each segment of each path according the schemes of FIG. 29*a*, FIG. 29*b*, FIG. 31. An elimination might occur if the driver is underperforming compared to the peer group or a threshold score/condition has been reached, for example, a severe accident causing loss of life, or very poor attention. Such an elimination has previously been discussed. In another elimination criterion, segments that do not have a minimum number of drivers (for example, at least 100 drivers) can be discarded. Some of these segments traversed (by the same driver, as well as other drivers) will naturally be under varying conditions, and some naturally under similar conditions. This data can be stored in a multi-path array as in FIG. 35. This data can also be stored as individual segments (instead of paths) as in FIG. 36, which also includes condition data.

C1 candidates can also be those who passed a test path with multiple segments, wherein the vehicle is a virtual vehicle (VV). The controls can be a combination of one or more of: a keyboard, mouse, gaming controllers, or a smartphone equipped with gyroscopes. The VV can also be a smartphone, with the phone's screen displaying the path, and the phone also acting as a controller, including using its gyroscopes and soft and hard buttons. The VV can also be a virtual reality (VR) system (head mounted, computer monitor based, or projected onto a screen).

C2 candidates can be C1 candidates who do well at C1 and are then promoted to C2. Alternatively, C2 candidates can also be recruited directly into this category without having to go through C1. C2 candidates operate VVs in CWs or VWs, and are provided with either hand sensors (as in FIG. 9*a*-FIG. 9*e*) or foot sensors (as in FIG. 10-FIG. 10*h*), or both. The VV can also be a smartphone, with the phone's screen displaying the path, with the phone also acting as a controller, including using its gyroscopes and soft and hard buttons. The VV can also be a virtual reality system (head mounted, computer monitor based, or projected onto a screen). As in C1, data for segments and paths, along with condition data, can be stored in a multi-path array as in FIG. 35. This data can also be stored as individual segments (instead of paths) as in FIG. 36, which also includes condition data. Aural sensors are optional in C2.

C3 candidates can be C2 candidates who do well at C2 and are then promoted to C3. Alternatively, C3 candidates can also be recruited directly into this category without having to go through C2 or C1. C3 candidates operate RVs in RWs, and are not provided with aural, hand or foot sensors. As in C2, data for segments and paths, along with condition data, can be stored in a multi-path array as in FIG. 35. This data can also be stored as individual segments (instead of paths) as in FIG. 36, which also includes condition data.

C4 is a higher category than C3, where a RV is driven in a RW, with the vehicle fitted with aural, foot and hand sensors. The smartphone camera(s) are used. C4 candidates are C3 candidates who do well at C3 and are then promoted. As in C3, data for segments and paths, along with condition data, can be stored in a multi-path array as in FIG. 35. This data can also be stored as individual segments (instead of paths) as in FIG. 36, which also includes condition data.

C5 is the last category in this particular series. Candidates operate a RV in a RW, with the vehicle fitted with aural, foot and hand sensors, where the camera can be a smartphone's camera(s) or standalone camera(s) or a combination. C5 candidates are C4 candidates who do well at C4. Alternatively, they can be recruited directly into this category from C3. As in C4, data for segments and paths, along with condition data, can be stored in a multi-path array as in FIG. 35. This data can also be stored as individual segments (instead of paths) as in FIG. 36, which also includes condition data.

In an embodiment, after the app is downloaded onto a smartphone, candidates register in C1, and work their way up to C5. In C1, no additional sensors (apart from the user's smartphone) are required. Since vehicles are VV operated in CW or VW, there is no possibility of real-life accidents or endangerment of life. The scoring scheme FIG. 32 is used to score candidates after they traverse a path (see text accompanying FIG. 32 for details). Multiple candidates are scored on multiple paths (as in FIG. 35) and EDs obtained for the array of FIG. 35. If thoroughness is required, then candidates are expected to traverse paths under different conditions and an array as in FIG. 35 or FIG. 36 is obtained. Cutoff scores are established for progression from one category to the next. For example, candidates who score above a C1 cutoff are allowed to progress to C2, and those who score above a C2 cutoff progress to C3, and so on. C3, C4 and C5 candidates continue gathering data while they go about their daily lives, or they can be specially tasked to complete certain number of hours or kilometers or paths. They can also be asked to traverse specific paths, or specific types of paths, under varying conditions. As sufficient data is being gathered, EDs can be established for segments and paths. EDs can also be established for geographical regions. Once EDs have been identified, AVs can be trained to improve their autonomous capabilities by mimicking these EDs. These improvements can be based on a single or a group of EDs. When a group is used, their responses can be averaged whenever needed (and possible with the type of data). Alternatively, a statistical method (incorporating standard deviations, mean, mode, average, or RMS values) can be applied to the responses and used to train AVs.

If there is a need to reduce storage space on a smartphone, driver facing camera video can be discarded. Instead, eye movement data can be appended to the road facing video frames. It can also be saved as a separate file with appropriate time stamps.

In an embodiment, a real-time camera feed of a vehicle is live transmitted over the internet with a connection having low lag. The vehicle is semi-autonomous, with a human sitting in the passenger or driver side seat and ready to take over controls when required. Normal functioning of the vehicle is autonomous using onboard software. A group of remote C5 drivers above an ED cutoff receive the live transmission, with the data being displayed on one or two monitors. At certain points during the traversal of the vehicle in a segment/path, the human in the vehicle lets the remote drivers drive the vehicle, with the autonomous software running and its instructions, actions and reactions being stored, but not in control of the vehicle anymore. The human in the car still has the ability to take over control if need be. Averaged values of the remote drivers, including turning and speed control (with appropriate filters to protect against malicious, illegal or dangerous actions), are transmitted on the low-lag connection to the vehicle to control it, with the human driver in the vehicle ready to take over control whenever required. The actions directed by the group are recorded onboard the vehicle. The autonomous vehicle software's control is compared to the group's control. Modifications are made to portions of the AV software that did not perform as well as the group. In an alternate embodiment, a single C5 driver can be used instead of a group.

Roads that are already mapped in a way suitable for AV use are currently a small fraction of roads that humans drive on. EDs can be selected from C4 and C5 to perform road mapping using cars equipped with appropriate gear, including high-res front and side facing cameras. ED selection criteria for this purpose can be restricted to those regularly traversing the same segments that need to be mapped, and scoring high on some non-events like lawfulness (2701), skills (2706) and knowledge (2708). Geolocation and timestamps of frequent occurrences of the same type of outside events encountered by drivers during mapping can also be stored in the map file, so that the newly mapped roads come per-equipped with training pointers for new drivers as well as new AV software requiring customization for that particular geographical area. Highest ranking EDs (selected from the array of FIG. 36) can be used as benchmarks for such mapped regions. Such benchmarks can be used to train AV software, or used to rank human drivers in all categories (C1-05) participating in a development platform as appearing in FIG. 37 and accompanying text.

The invention claimed is:

1. A system comprising: at least one imaging device configured to acquire images of at least one eye of a human subject operating a vehicle, a processing unit configured to process the acquired images to extract eye data from said images to form training data, the eye data corresponding to movement of the at least one eye and associated with at least one of: saccades, glissades, square-wave jerks, smooth pursuits, wherein the training data is used to train vehicles to become partially or fully autonomous or to improve their autonomous functioning, wherein the vehicle having a brake pedal and an accelerator pedal controlled by a foot of the human, and a wall behind these pedals, the training data further comprising foot data relating to: distance of the foot from the brake pedal, distance of the foot from the accelerator pedal, distance of the brake pedal from the wall behind it, and distance of the accelerator pedal from the wall behind it.

2. The system of claim 1, wherein the eye data additionally corresponds to the position of the at least one eye associated with at least one of: fixations, tremors, drift, microsaccades.

3. The system of claim 1, the training data further comprising hand data relating at least one of: the grip force or the contact area of at least one hand of the human on the steering wheel of the vehicle.

4. The system of claim 1, the training data further comprising aural data.

* * * * *